(12) United States Patent
Pfahl et al.

(10) Patent No.: US 7,153,875 B2
(45) Date of Patent: Dec. 26, 2006

(54) HETEROCYCLIC DERIVATIVES FOR THE TREATMENT OF CANCER AND OTHER PROLIFERATIVE DISEASES

(75) Inventors: Magnus Pfahl, Solana Beach, CA (US); Catherine Tachdjian, San Diego, CA (US); Hussien A. Al-Shamma, Encinitas, CA (US); Andrea Fanjul, San Diego, CA (US); David P.M. Pleynet, San Diego, CA (US); Lyle W. Spruce, Chula Vista, CA (US); Torsten R. Wiemann, Cardiff by the Sea, CA (US); Jason B. Ibarra, Imperial Beach, CA (US)

(73) Assignee: Incyte San Diego, Wilmington, DE (US)

( * ) Notice: Subject to any disclaimer, the term of this patent is extended or adjusted under 35 U.S.C. 154(b) by 0 days.

(21) Appl. No.: 10/094,142

(22) Filed: Mar. 7, 2002

(65) Prior Publication Data

US 2002/0143182 A1    Oct. 3, 2002

Related U.S. Application Data

(60) Provisional application No. 60/274,751, filed on Mar. 7, 2001.

(51) Int. Cl.
C07D 401/06 (2006.01)
A61K 31/44 (2006.01)

(52) U.S. Cl. .................................... 514/342; 546/269.7
(58) Field of Classification Search ............. 546/269.7, 546/270.4, 274.1, 274.4, 14; 514/341, 342
See application file for complete search history.

(56) References Cited

U.S. PATENT DOCUMENTS

| | | | |
|---|---|---|---|
| 4,051,842 A | 10/1977 | Hazel et al. | |
| 4,140,122 A | 2/1979 | Kühl et al. | |
| 4,383,529 A | 5/1983 | Webster | |
| 4,668,506 A | 5/1987 | Bawa | |
| 4,713,244 A | 12/1987 | Bawa et al. | |
| 4,788,063 A | 11/1988 | Fisher et al. | |
| 4,931,279 A | 6/1990 | Bawa et al. | |
| 4,948,900 A * | 8/1990 | Iijima et al. | 548/183 |
| 4,971,996 A | 11/1990 | Shiraishi et al. | |
| 5,223,522 A | 6/1993 | Clark et al. | |
| 5,330,998 A | 7/1994 | Clark et al. | |
| 5,512,689 A | 4/1996 | Quallich | |
| 5,523,314 A | 6/1996 | Bue-Valleskey et al. | |
| 5,650,444 A | 7/1997 | Cagiano et al. | |
| 5,691,376 A | 11/1997 | Cagiano et al. | |
| 5,780,676 A | 7/1998 | Boehm et al. | |
| 5,972,986 A | 10/1999 | Seibert et al. | |
| 6,127,415 A | 10/2000 | Pfahl et al. | |
| 6,262,044 B1 | 7/2001 | Møller et al. | |
| 6,515,003 B1 | 2/2003 | Pfahl et al. | |
| 6,765,013 B1 | 7/2004 | Pfahl et al. | |
| 6,927,228 B1 | 8/2005 | Bernardon et al. | |
| 2003/0083357 A1 | 5/2003 | Pfahl et al. | |
| 2003/0105333 A1 | 6/2003 | Pfahl et al. | |
| 2003/0144329 A1 | 7/2003 | Pfahl et al. | |
| 2003/0153606 A1 | 8/2003 | Pfahl et al. | |
| 2003/0216432 A1 | 11/2003 | Pfahl et al. | |
| 2004/0034004 A1 | 2/2004 | Pfahl et al. | |
| 2004/0097566 A1 | 5/2004 | Pfahl et al. | |

FOREIGN PATENT DOCUMENTS

| | | |
|---|---|---|
| EP | 0 212 617 | 3/1987 |
| EP | 0 304 493 | 3/1989 |
| EP | 0 343 643 | 11/1989 |
| EP | 1 048 659 | 11/2000 |
| EP | 1 142 885 | 10/2001 |
| JP | 55 038359 | 3/1980 |
| WO | WO 93/21146 | 10/1993 |
| WO | WO 94/12880 | 6/1994 |
| WO | WO 97/00249 | 1/1997 |
| WO | WO 97/03682 | 2/1997 |
| WO | WO 97/27191 | 7/1997 |
| WO | WO 99/09965 | 3/1999 |
| WO | WO 99/24415 | 5/1999 |

(Continued)

OTHER PUBLICATIONS

Strandtmann et al. , J. Med. Chem. (1967), 10(6);1063-1065.*

(Continued)

*Primary Examiner*—Zinna N. Davis
(74) *Attorney, Agent, or Firm*—Needle & Rosenberg, P.C.

(57) ABSTRACT

The invention relates to certain heterocyclic compounds useful for the treatment of cancer and other diseases, having the Formula (I):

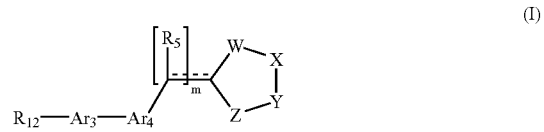

wherein:
(a) m is an integer 0 or 1;
(b) $R_{12}$ is an alkyl, a substituted alkyl, a cycloalkyl, a substituted cycloalkyl, a heterocyclic, a substituted heterocyclic, a heteroaryl, a substituted heteroaryl, an aryl or a substituted aryl residue;
(c) $Ar_3$ is an aryl, a substituted aryl, a heteroaryl or a substituted heteroaryl residue;
(d) $Ar_4$ is an aryl, a substituted aryl, a heteroaryl or a substituted heteroaryl residue;
(e) $R_5$ is hydrogen, hydroxy, alkyl or substituted alkyl;
(f) ----- represents a bond present or absent; and
(g) W, X, Y and Z are independently or together —C(O)—, C(S), S, O, or NH;
or a pharmaceutically acceptable salt thereof.

9 Claims, 17 Drawing Sheets

FOREIGN PATENT DOCUMENTS

| | | |
|---|---|---|
| WO | WO 99/58127 | 11/1999 |
| WO | WO 00/10573 | 3/2000 |
| WO | WO 00/18748 | 4/2000 |
| WO | WO 00/32598 | 6/2000 |
| WO | WO 00/63196 | 10/2000 |
| WO | WO 00/66167 | 11/2000 |
| WO | WO 01/16122 | 3/2001 |
| WO | WO 01/16123 | 3/2001 |
| WO | WO 01/36402 | 5/2001 |
| WO | WO 02/12210 | 2/2002 |
| WO | WO 02/071827 | 9/2002 |
| WO | WO 02/072009 | 9/2002 |
| WO | WO 02/072543 | 9/2002 |
| WO | WO 02/080935 A1 | 10/2002 |
| WO | WO 2004/113331 | * 12/2004 |

OTHER PUBLICATIONS

Sof'ina et al. Experimental Evaluation of Antitumor Drugs in the USA and USSR and Clinical Correlations. NCI Monograph 55. NIH Publication No. 80-1933 (1980).*

Singh et al. Indian Drugs (1985), 22(10) : 519-23.*

Alley et al., "Feasibility of Drug Screening with Panels of Human Tumor Cell Lines Using a Microculture Tetrazolium Assay," *Cancer Res.* 48:589-601 (1988).

Amin et al., "Nitric Oxide Synthase and Cyclooxygenases: Distribution, Regulation, and Intervention in Arthritis," *Nitric pin. Rheumatol*, 11(3):202-209 (1999).

Aranyos et al., "Novel Electron-Rich Bulky Phospine Ligands Facilitate the Palladium-Catalyzed Preparation of Diaryl Ethers," *J. Am. Chem. Soc.* 121:4369-4378 (1999).

Baraldi et al., "Exhaled Nitric Oxide Concentrations During Treatment of Wheezing Exacerbation in Infants and Young Children," *Am. J. Respir. Crit. Care Med.*, 159 (4 Pt. 1):1284-1288 (1999).

Beilstein Registry No. 29-30, 1975, Compound Registry No. 1120438.

Beilstein Registry No. 52, 1978, Compound Registry No. 4939128.

Black, "Simple Synthesis of 1-Azaadamantan-4-one," *Synthesis* 829-830 (1981).

Bradisher et al., "Aromatic Cyclodehydration XXIV. Cyclization of Derivatives of (2-biphenylly)pyruvic Acid," *J. Org. Chem.*, 15(2) 374-376 (1950).

Bredt et al., "Isolation of Nitric Oxide Synthetase, a Calmodulin-Requiring Enzyme," *Proc. Natl. Acad. Sci.* 87:682-685 (1990).

Brennan et al., "Inhibitory Effect of TNFα Antibodies on Synovial Cell Interleukin-1 Production in Rheumatoid Arthritis," *Lancet*, 2:244-247 (1989).

Chan et al., "New N- and O-Arylations with Phenyloboronic Acids and Curpric Acetate," *Tetrahedron Letters* 39:2933-2936 (1998).

Charpentier et al., "Synthesis, Structure—Affinity Relationships, and Biological Activities of Ligands Binding to Retinoic Acid Receptor Subtypes," *J. Med. Chem.* 38:4993-5006 (1995).

Choi et al., "Similarity of Colorectal Cancer in Crohn's Disease and Ulcerative Colitis: Implications for Carcinogenesis and Prevention," *Gut*, 35:950-954 (1994).

Cobb et al., "N-(2-Benzoylphenyl)-L-tyrosine PPARγ Agonists. 3. Structure-Activity Relationship and Optimization of the N-Aryl Substituent," *J. Med. Chem.* 41:5055-5069 (1998).

Darses et al., "Palladium-Catalyzed Cross-Coupling Reactions of Arenediazonium Tetrafluoroborates with Aryl- and Alkenylboronic Acids," *Bull. Soc. Chem. Fr.*, 133:1095-1102 (1996).

Ebisawa et al., "Novel Thiazolidinedione Derivatives with Retinoid Synergistic Activity," *Biol. Pharma. Bull.*, 21(5):547-549 (1998).

Evans et al., "Synthesis of Diaryl Ethers through the Cooper-Promoted Arylation of Phenols with Arylboronic Acids. An Expedient Synthesis of Thyroxine," *Tetrahedron Letters* 39:2937-2940 (1998).

Farahat et al., "Cytokine Epression in Synovial Membranes of Patients with Rheumatoid Arthritis and Osteoarthritis," *Ann. Rheum. Dis.*, 52: 870-875 (1993).

Ferrell, "Tripping the Switch Fantastic: How A Protein Kinase Cascade Can Convert Graded Inputs into Switch-Like Outputs," *TIBS*, 21:460-466 (1996).

Firooznia et al., "Enantioselective Synthesis of 4-Substituted Phenylalanines By Cross-Coupling Reactions," *Tetrahedron Letters*, 40:213-216 (1999).

Förstermann et al., "Induced RAW 264.7 Macrophages Express Soluble and Particulate Nitric Oxide Synthase: Inhibition By Transforming Growth Factor-β," *Eur. J. Pharm.*, 225:161-165 (1992).

Fukuto et al., "Inhibition of Constitutive and Inducible Nitric Oxide Synthase: Potential Selective Inhibition," *Annu. Rev. Pharmacol. Toxicol.* 35:165-194 (1995).

Gahtan et al., "Inflammatory Pathogenesis in Alzheimer's Disease: Biological Mechanisms and Cognitive Sequeli," *Neurosci: Biobehav*, 23:615-633 (1999).

Glauser et al., "Pathogenesis and Potential Strategies for Prevention and Treatment of Septic Shock: An Update," *Clin. Infect Dis.* 18 (Suppl. 2):S205-216 (1994).

Haddach et al., "A New Method for the Synthesis of Ketones: The Palladium-Catalyzed Corss-Coupling of Acid Chlorides with Arylboronic Acids," *Tetrahedron Letters* 40:3109-3112 (1999).

Harris et al., "Localization of a Pioglitazone Response Element in the Adipocyte Fatty Acid-Binding Protein Gene," *Mol. Pharmacol.* 45:439-445 (1994).

Hudlicky, "Oxidations in Organic Chemistry," ACS Monograph 186:114-127 (1990).

Hudlicky, "Oxidations in Organic Chemistry," ACS Monograph 186:133-149 (1990).

Indolese, "Suzuki-Type Coupling of Chloroarenes with Arylboronic Acids Catalysed by Nickel Complexes," *Tetrahedron Letters*, 38:3513-3516 (1997).

Ishiyama et al., "Palladium(0)-Catalyzed Cross-Coupling Reaction of Alkoxydiboron with Haloarenes: A Direct Procedure for Arylboronic Esters," *J. Org. Chem.*, 60:7508-7510 (1995).

Ishiyama et al., "Palladium-Catalyzed Carboonylative Cross-Coupling Reaction of Arylboronic Acids with Aryl Electrophiles: Synthesis of Biaryl Ketones," *J. Org. Chem.*, 63:4726-4731 (1998).

Ishiyama et al. "Synthesis of Arylboronates via the Palladium(0)-Catalyzed Cross-Coupling Reaction of Tetra(alkoxo)diborons with Aryl Triflates," *Tetrahedron Letters*, 38:3447-3450 (1997).

Ishiyama et al. "Synthesis of Unsymmetrical Biaryl Ketones via Palladium-Catalyzed Carbonylative Cross Coupling Reaction of Arylboronic Acids with Iodoarenes," *Tetrahedron Letters*, 34:7595-7598 (1993).

Jung et al., "New Efficient Method for the Total Synthesis of (S,S)-Isodityrosine from Natural Amino Acids," *J. Org. Chem.* 64:2976-2977 (1999).

Kamidawa et al., "Palladium-Catalyzed Amination of Aryl Bromides Utilizing Arene-Chromium Complexes as Ligands," *J. Org. Chem.* 63:8407-8410 (1998).

Kawai et al., "Enhancement of Rat Urinary Bladder Tumorigenesis by Lipopolysaccharide-induced inflammation," *Cancer Res.* 53:5172-5175 (1993).

Kriegler et al., "A Novel Form of TNF/Cachectin is a Cell Surface Cytotoxic Transmembrane Protein: Ramifications for the Complex Physiology of TNF," *Cell*, 53:45-53 (1988).

Kyriakis et al., "Sounding the Alarm: Protein Kinase Cascades Activated by Stress and Inflammation," *J. Biol Chem.*, 271:24313-24316 (1996).

Littke and Fu, "A Convenient and General Method for Pd-Catalyzed Suzuki Cross-Couplings of Aryl Chlorides and Arylboronic Acids," *Angew. Chem. Int. Ed.*, 37:3387-3388 (1998).

Manickam et al., "New Parts for a Construction Set of Bifunctional Oligo(het)arylene Building Blocks for Modular Chemistry," *Synthesis*, 3:442-446 (2000).

McCann et al., "The Nitric Oxide Hypothesis of Aging," *Exp. Gerontol*, 33(7-8):813-826 (1998).

McCann, "The Nitric Oxide Hypothesis of Brain Aging," *Exp. Gerontol*. 32:431-440 (1997).

Miyaura et al., "Palladium-Catalyzed Cross-Coupling Reactions of Organoboron Compounds," *Chem. Rev.* 95:2457-2483 (1995).

Molina et al., "the Role of Nitric Oxide in Neurodegeneration—Potential for Pharmacological Intervention," *Drugs & Aging*, 12(4):251-259 (1998).

Moroz et al., "The Ullmann Ether Condensation," *Russ. Chem. Rev.* 43:679-689 (1974).

Oliff, "The Role of Tumor Necrosis Factor (Cachectin) in Cachexia," *Cell*, 54:141-142 (1988).

Paradisi, "Arene Substitution via Nucleophilic Addition to Electron Deficient Arenes," *Comprehensive Organic Synthesis* 4:423-450 (1991).

Petrov et al., "The Arbuzov Rearrangement with Participation of Halogenoacetylenes as a Method of Synthesis of Ethynylphosphonates and other Organo-phosphorus Compounds," *Russ. Chem. Rev.* 52:1030-1035 (1983).

Pohlman et al., "An Endothelial Cell Surface Factor(s) Induced in Vitro By Lipopolysaccharide, Interleukin 1, and Tumor Necrosis Factor-$\alpha$ Increases Neutrophil Adherence By A CDw18-Dependent Mechanism," *J. Immunol*, 136: 4548-4553 (1986).

Pollock et al., "Purification and Characterization of Particulate Endothelium-derived Relaxing Factor Synthase from Cultured and Native Bovine Aortic Endothelial Cells," *Proc. Nat. Acad. Sci.*, 88:10480-10484 (1991).

Pujol-Borrell et al., "HLA Class II Induction In Human Islet Cells By Interferon-$\gamma$ Plus Tumour Necrosis Factor or Lymphotoxin," *Nature*, 326:304-306 (1987).

Rosin et al., "Inflammation, Chromosomal Instability, and Cancer: The Schistosomiasis Model" *Cancer Res.*, 54(7 Suppl):1929s-1933s (1994).

Sanders, "Asthma, Viruses, and Nitric Oxide," *Proc. Soc. Exp. Biol. Med.*, 220(3):123-132 (1999).

Schandendorf et al., "Retinoic Acid Receptor Selective Retinoids Exert Antiproliferative Effects on Human Melanoma Cell Growth In Vitro, " *International Journal of Oncology* 5:1325-1331 (1994).

Shao et al., "p53 Independent $G_0/G_1$ Arrest and Apoptosis Induced by a Novel Retinoid in Human Breast Cancer Cells," *Oncogene* 11:493-504 (1995).

Smith et al., "The Active Form of Tumor Necrosis Factor Is A Trimer," *J. Biol. Chem.*, 262:6951-6954 (1987).

Spruce et al., "Heteroarotinoids. Synthesis, Characterization, and Biological Activity in Terms of an Assessment of these Systems to Inhibit the Induction of Ornithine Decorboxylase Activity and to Induce Terminal Differentiation of HL-60 Cells," *J. Med. Chem.* 30:1474-1482 (1987).

Stanforth, "Catalytic Cross-Coupling Reactions in Biaryl Synthesis," *Tetrahedron*, 54:263-303 (1998).

Stirling et al., "Increase In Exhaled Nitric Oxide Levels in patients With Difficult Asthma and Correlation With Symptoms and Disease Severity Despite Treatment With Oral and Inhaled Corticosteroids," *Thorax*, 53(12):1030-1034 (1998).

Strieter et al., "Endothelial Cell Gene Expression of a Neutrophil Chemotactic Factor by TNF-$\alpha$, LPS, and IL-1$\beta$," *Science*, 243:1467-1469 (1989).

Suzuki, "New Synthetic Transformations Via Organoboron Compounds," *Pure & Applied Chem.*, 66:213-222 (1994).

Teboul et al., "Thiazolidinediones and Fatty Acids Convert Myogenic Cells Into Adipose-like Cells," *J. Biol. Chem.* 270:28183-28187 (1995).

Thorns et al., "nNOS Expressing Neurons in the Entorhinal Cortex and Hippocampus Are Affected in Patients With Alzheimer's Disease," *Exp. Neurol*, 150:14-20 (1998).

Tietze et al., "The Knoevenagel Reaction," *Comprehensive Organic Synthesis*, 2:341-394, (1991).

Tracey et al., "Anti-Cachectin/TNF Monoclonal Antibodies Prevent Septic Shock During Lethal Bacteraemia," *Nature*, 330:662-664 (1987).

Tracey et al., "Tumor Necrosis Factor: A Pleiotropic Cytokine and Therapuetic Target," *Ann. Rev. Med.* 45:491-503 (1994).

Uysal et al. "Protection From Obesity-induced Insulin Resistance in Mice Lacking TNF-$\alpha$ Function," *Nature* 389:610-614 (1997).

Wadsworth, "Synthetic Applications of Phosphoryl-Stabilized Anions," *Organic Reactions* 25:73-253 (1977).

Watanabe et al., "Synthesis of Sterically Hindered Biaryls via the Palladium-Catalyzed Cross-Coupling Reaction of Arylboronic Acids or Their Esters With Haloarenes," *Synlett*, 207-210 (1992).

Weiberth et al., "Copper(I)-Activated Addition of Grignard Reagents to Nitriles. Synthesis of Ketimines, Ketones, and Amines," *J. Org. Chem.* 52:3901-3904 (1987).

Willson et al., "The Structure-Activity Relationship Between Peroxisome Proliferator-Activated Receptor $\gamma$ Agonism and the Antihyperglycemic Activity of Thiazolidinediones," *J. Med. Chem.*, 39:665-668 (1996).

Wolfe et al., "Scope and Limitations of the Pd/BINAP-Catalyzed Amination of Aryl Bromides," *J. Org. Chem.* 65:1144-1157 (2000).

Wolfe et al., "Simple, Efficient Catalyst System for the Palladium-Catalyzed Amination of Aryl Chlorides, Bromides and Triflates," *J. Org. Chem.* 65:1158-1174 (2000).

Yun et al., "Neurobiology of Nitric Oxide," *Crit. Rev. Neurobiol.* 10:291-316 (1996).

Zack et al., "Synthesis of 3-Mercapto-2(5H)-Furanones via Reaction of Dilithio-2,4-Thiazolidinedione With $\alpha$-Halo Ketones," *Tetrahedron Letters*, 34 (17):2719-2722 (1993).

Barclay et al., "ortho-Diquaternary aromatic compounds. III. Synthesis and reactions of polyalkyltetralones and derivatives," *Canadian Journal of Chemistry*, 48(17):2763-2775 (1970).

Cacchi et al., "Palladium-Catalyzed Triethylammonium Formate Reduction of Aryl Triflates. A Selective Method for the deoxygenation of phenols," *Tetrahedron Letters*, 27(45):5541-5544 (1986).

Faul et al., "Synthesis of Novel Retinoid X Receptor-Selective Retinoids," *J. Org. Che.*, 66:5772-5782 (2001).

Iwatsuka et al., "General Survey of Diabetic Features of Yellow KK Mice," *Endocrinol. Japon.* 17:23-35 (1970).

Xiong et al., "Human D-Type Cyclin," *Cell*, 65:691-699 (1991).

Gray et al., "Practical Methylation of Aryl Halides by Suzuki-Miyaura Coupling," *Tetrahedron Letters*, 41:6237-6240 (2000).

Louie et al., "Palladium-Catalyzed Amination of Aryl Triflates and Importance of Triflate Addition Rate," *J. Org. Chem.*, 62:1268-1273 (1997).

Oram, "Molecular Basic of Cholesterol Homeostasis: Lessons from Tangier Disease and ABCA1," *Trends in Molecular Medicines*, 8(4):168-173 (2002).

Ross "Atherosclerosis—An Inflammatory Disease," *New England Journal of Medicine*, 340(2):115-126 (Jan. 1999).

Rust et al. "Tangier disease is caused by mutations in the gene encoding ATP-binding cassette transporter 1," *Nature Genetics*, 22:352-355 (Aug. 1999).

Serfaty-Lacrosniere et al., "Homozygous Tangier disease and cardiovascular disease," *Atherosclerosis*, 107:85-98 (1994).

Sparrow et al., "A Potent Synthetic LXR Agonist is More Effective than Cholesterol Loading at Inducing ABCA1 mRNA and Stimulating Cholesterol Efflux," *Journal of Biological Chemistry*, 277(12):10021-10027 (2002).

Thompson et al., "Effect of carcinogen dose and age at administration on induction of mammary carcinogenesis by 1-methyl-1-nitrosourea," *Carginogenesis*, 13(9):1535-1539 (1992).

Walter et al., "The High Density Lipoprotein—and Apolipoprotein A-1-Induced Mobilization of Cellular Cholesterol is Impaired in Fibroblasts from Tangier Disease Subjects," *Biochemical and Biophysical Research Communications*, 205(1):850-856 (1994).

Zack et al., "Synthesis and Antihyperglycemic Activity of Novel 5-(naphthalenylsufonyl)-2,4-thiazolidinediones," *J.Med. Chem.*, 33:1418-1423 (1990).

Blondet et al., "Convenient Synthesis of 6-Methyl, 8-Methyl and 6,8-Dimethyl Derivatives of 5-Hydroxy-1,2,3,4-Tetrahydro-2-Quinolinone," *Organic Preparation and Procedures Int.*, 25(2):223-228 (1993).

Cantello et al., "A Versatile Route to 2-Arylmethyl1-1,2-oxadiazolidine-3,5-diones via Regiospecific Alkyl-ation of 1,2,4-Oxadiazolidine-3,5-dione," *Sym;ett*, 263-264 (1997).

Cantello et al., "The Synthesis of BRL 49653—A Novel and Potent Antihyperglycaemic Agent," *Biorganic & Medicinal Chemistry Letters*, 4:1181-1184 (1994).

Chang et al., "The Upjohn Colony of Kka^y Mice: A Model for Obese Type II Diabetes," *Elsevier Science Publishers B.V., Biomedical Division, Diabetes*, pp. 466-470 (1986).

Coleman "Diabetes-Obesity Syndromes in Mice," *Diabetes*, 31(1):1-6 (Apr. 1982).

Dawson et al., "Conformational Effects on Retinoid Receptor Selectivity. 2. Effects of Retinoid Bridging Group on retinoid X Receptor Activity and Selectivity," *J. Med. Chemistry*, 38:3368-3383 (1995).

Dawson et al., "The Synthetic Chemistry of Retinoids," *Biology, Chemistry, and Medicine*, 2nd Edition, Raven Press, Ltd., New York (1994).

Gown, et al., "Human Atherosclerosis—II. Immunocytochemical Analysis of the Cellular Composition of human Atherosclerotic Lesions," *Am. J. Pathol.*, 125(1):191-207 (1986).

* cited by examiner

HETEROCYCLIC DERIVATIVES FOR THE TREATMENT OF CANCER AND OTHER PROLIFERATIVE DISEASES

RELATED APPLICATIONS

This application claims priority to U.S. provisional application Ser. No. 60/274,751, filed Mar. 7, 2001, the disclosure of which application is hereby incorporated in its entirety by this reference.

BACKGROUND OF THE INVENTION

Solid tumors are the leading cause of death attributable to cancers worldwide. Conventional methods of treating cancer include surgical treatments, the administration of chemotherapeutic agents, and recently immune based treatments, which typically involve the administration of an antibody or antibody fragment. Although some encouraging results are being reported with the latter, an effective, life-prolonging treatment or a cure is not yet available for most cancers.

Surgical treatments are generally only successful if the cancer is detected at an early stage, i.e., before the cancer has infiltrated major organs. Chemotherapeutic treatments available today are also of limited usefulness because of their non-selective killing and/or toxicity to most cell types. Also, many tumor cells eventually become resistant against the chemotherapeutic agent, thus requiring treatment of such resistant tumors with new agents. Immune based treatments are also subject to numerous problems including difficulty in targeting antibodies to desired sites, e.g., solid tumors, and host immune reactions to the administered antibody.

The usage of small molecules for the prevention and treatment of cancer has also been reported. Antiestrogens and antiandrogens for the treatment/prevention of breast and prostate cancer, respectively, are excellent examples of a class of small molecule ligands that function via nuclear receptor signaling pathways. Another class of promising small molecule anti-cancer agents appears to be protein kinase inhibitors. Both classes of compounds are heterocyclic molecules in the 300 to 600 molecular weight range. Certain small molecules that are in some ways structurally related to the compounds of the instant invention, and disclosed to be potentially useful in the treatment of certain cancers were disclosed in U.S. patent application Ser. No. 09/655,460 filed Aug. 31, 2000. Certain other small molecules effective for the treatment of diabetes, that are in some ways structurally related to the compounds of the instant invention were disclosed in U.S. patent application Ser. No. 09/652,810 filed Aug. 31, 2000. The disclosures of both the above-described U.S. patent applications are hereby incorporated herein by this reference, for both their chemical structural disclosures, and their teachings of the biological activities of those compounds, and methods for their use as pharmaceutical compositions.

The present invention relates to a series of heterocyclic compounds that show unexpected, potent anti-cancer activity in vitro and in vivo. These compounds are useful in the treatment of diseases of uncontrolled proliferation, such as cancer and precancerous conditions, in mammals. This invention also relates to a method of using such compounds in the treatment of diseases of uncontrolled proliferative diseases in mammals, especially humans, and to pharmaceutical compositions containing compounds disclosed herein.

SUMMARY OF THE INVENTION

The present invention relates to certain substituted heterocycles which are useful in the treatment of diseases related to uncontrolled cellular proliferation, such as cancer or precancerous conditions.

Some disclosed embodiments of the invention relate to compounds of the Formula (I):

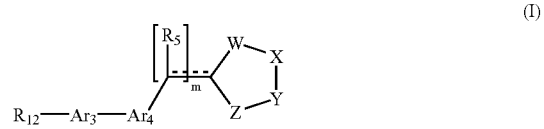

(I)

wherein:
(a) m is an integer 0 or 1;
(b) $R_{12}$ is an alkyl, a substituted alkyl, a cycloalkyl, a substituted cycloalkyl, a heterocyclic, a substituted heterocyclic, a heteroaryl, a substituted heteroaryl, an aryl or a substituted aryl residue;
(c) $Ar_3$ is an aryl, a substituted aryl, a heteroaryl or a substituted heteroaryl residue;
(d) $Ar_4$ is an aryl, a substituted aryl, a heteroaryl or a substituted heteroaryl residue;
(e) $R_5$ is hydrogen, hydroxy, alkyl or substituted alkyl;
(f) ----- represents a bond present or absent; and
(g) W, X, Y and Z are independently or together —C(O)—, C(S), S, O, or NH;

or a pharmaceutically acceptable salt thereof.

In other aspects the invention relates to compounds of the formula:

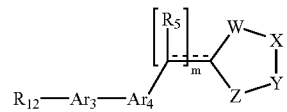

wherein:
(a) $Ar_3$ is an aromatic ring residue having the formula:

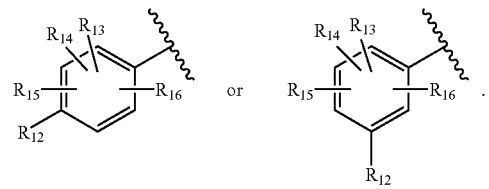

wherein
(i) $R_{12}$ is an alkyl, a substituted alkyl, a cycloalkyl, a substituted cycloalkyl, a heterocyclic, a substituted heterocyclic, a heteroaryl, a substituted a heteroaryl, an aryl, or a substituted aryl residue, and
(ii) $R_{13}$, $R_{14}$, $R_{15}$ and $R_{16}$ are independently or together hydrogen, an alkyl, a substituted alkyl, an alkenyl, a substituted alkenyl, an alkynyl, a substituted alkynyl, a cycloalkyl, a substituted a cycloalkyl, a heterocyclic, a substituted heterocyclic, an alkoxy, a substituted alkoxy, a hydroxyl, an acyl, an amino, a mono-substituted amino, a di-substituted amino, carboxy, a carboalkoxy, a nitrile an alkylcarboxamide, a substituted an alkylcarboxamide, a dialkylcarboxamide, a substituted dialkylcarboxamide, a haloalkoxy, a triorganosilyloxy, a heteroaryl, a substituted heteroaryl, an aryl, or a substituted aryl residue, or two of $R_{13}$, $R_{14}$, $R_{15}$ and $R_{16}$ together with the aromatic ring form an alkylene-dioxy ring, and (b) $Ar_4$ is an unsubstituted aryl, a substituted aryl, a heteroaryl or a substituted heteroaryl residue (c) $R_5$ is hydrogen, hydroxy, alkyl or substituted alkyl;

(d) ----- represents a bond present or absent;

(e) m is the integers 0 or 1; and (f) W, X, Y and Z form a residue of formula:

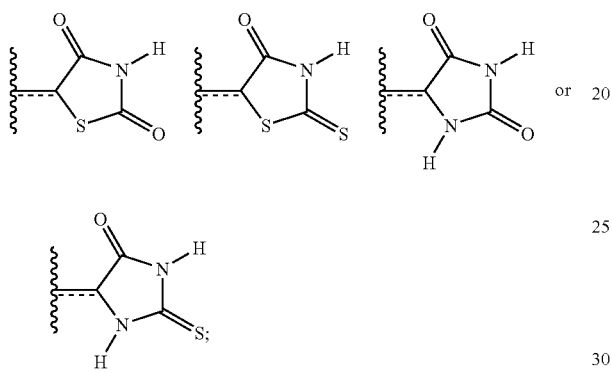

or a pharmaceutically acceptable salt thereof.

In yet other aspects, the invention relates to compounds of the formula:

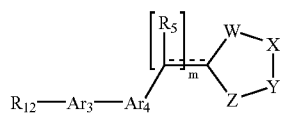

wherein:

(a) $Ar_3$ is an aromatic ring residue having the formula:

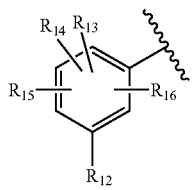

wherein (i) $R_{12}$ is an alkyl, a substituted alkyl, a cycloalkyl, a substituted cycloalkyl, a heterocyclic, a substituted heterocyclic, a heteroaryl, a substituted a heteroaryl, an aryl, or a substituted aryl residue, and (ii) $R_{13}$, $R_{14}$, $R_{15}$ and $R_{16}$ are independently or together hydrogen, an alkyl, a substituted alkyl, an alkenyl, a substituted alkenyl, an alkynyl, a substituted alkynyl, a cycloalkyl, a substituted a cycloalkyl, a heterocyclic, a substituted heterocyclic, an alkoxy, a substituted alkoxy, a hydroxyl, an acyl, an amino, a monosubstituted amino, a di-substituted amino, a carboxy, a carboalkoxy, a nitrile an alkylcarboxamide, a substituted an alkylcarboxamide, a dialkylcarboxamide, a substituted dialkylcarboxamide, a haloalkoxy, a triorganosilyloxy, a heteroaryl, a substituted heteroaryl, an aryl, or a substituted aryl residue, or two of $R_{13}$, $R_{14}$, $R_{15}$ and $R_{16}$ together with the aromatic ring form an alkylene-dioxy ring; and (iii) $Ar_3$ and $R_{12}$ do not together form a substituted or unsubstituted 5,6,7,8-tetrahydro-2-napthyl residue, a substituted or unsubstituted 1,2,3,4-tetrahydro-6-quinolinyl residue, or a substituted or unsubstituted 1,2,3,4-tetrahydro-7-quinoxalinyl residue;

(b) $Ar_4$ is an aryl, a substituted aryl, a heteroaryl, or a substituted heteroaryl residue comprising the structure:

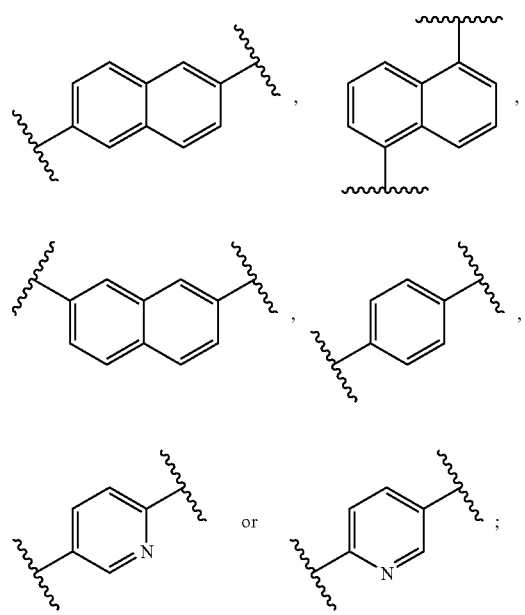

(c) $R_5$ is hydrogen;

(d) ----- represents a bond present or absent;

(e) m is the integer 1; and (f) W, X, Y and Z form a residue of formula:

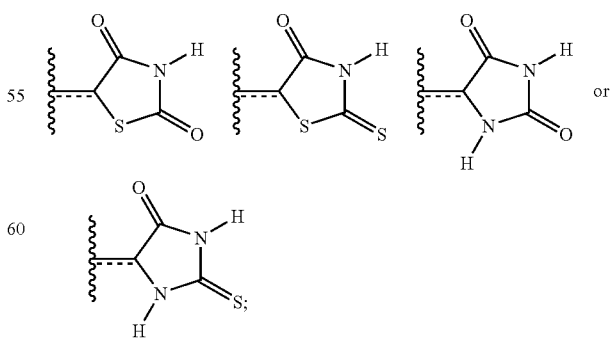

or a pharmaceutically acceptable salt thereof.

Some other disclosed embodiments of the invention relate to compounds having a bridging group "A" between the aromatic rings, of the Formula (II):

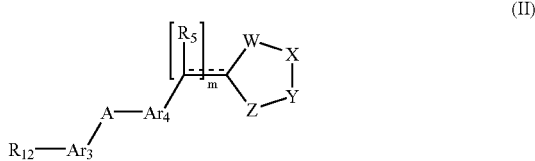

wherein:
(a) m is an integer 0 or 1;
(b) $R_{12}$ is an alkyl, a substituted alkyl, a cycloalkyl, a substituted cycloalkyl, a heterocyclic, a substituted heterocyclic, a heteroaryl, a substituted heteroaryl, an aryl or a substituted aryl residue;
(c) $Ar_3$ comprises an aryl, a substituted aryl, a heteroaryl or a substituted heteroaryl residue,
(d) A is an alkylene, a substituted an alkylene, O, S, NH, N-alkyl, N-substituted alkyl, —C(O)—, carboxamide or an alkylcarboxamide residue,
(e) Ar4 is an aryl, a substituted aryl, a heteroaryl or a substituted heteroaryl residue;
(f) $R_5$ is hydrogen, alkyl or substituted alkyl;
(g) ----- represents a bond present or absent; and
(h) W, X, Y and Z are independently or together —C(O)—, C(S), S, O, or N—H residues;

with the proviso that when $R_{12}$ and $Ar_3$ together are a 3,5,5,8,8-pentamethyl-5,6,7,8-tetrahydro-2-naphthyl or 5,5,8,8-tetramethyl-5,6,7,8-tetrahydro-2-naphthyl residue, $Ar_4$ is an unsubstituted 1,4-benzene residue, and W, X, Y and Z together form a 2,4-thiazolidinedione residue, then A does not comprise a carboxamide residue, an alkylcarboxamide residue, an N-alkyl residue, or a >C═CH2 residue; or a pharmaceutically acceptable salt thereof.

Other embodiments of the invention relate to methods of synthesizing the compounds disclosed herein.

In another aspect, this invention relates to the use of the compounds disclosed herein for treating diseases in mammals and/or humans, especially diseases of cellular proliferation, including cancers.

In still another aspect, this invention relates to a pharmaceutical composition for the treatment of diseases of uncontrolled cellular proliferation and cancers comprising a compound disclosed herein as an admixture with one or more pharmaceutically acceptable excipients.

DETAILED DESCRIPTION

Figure 1:
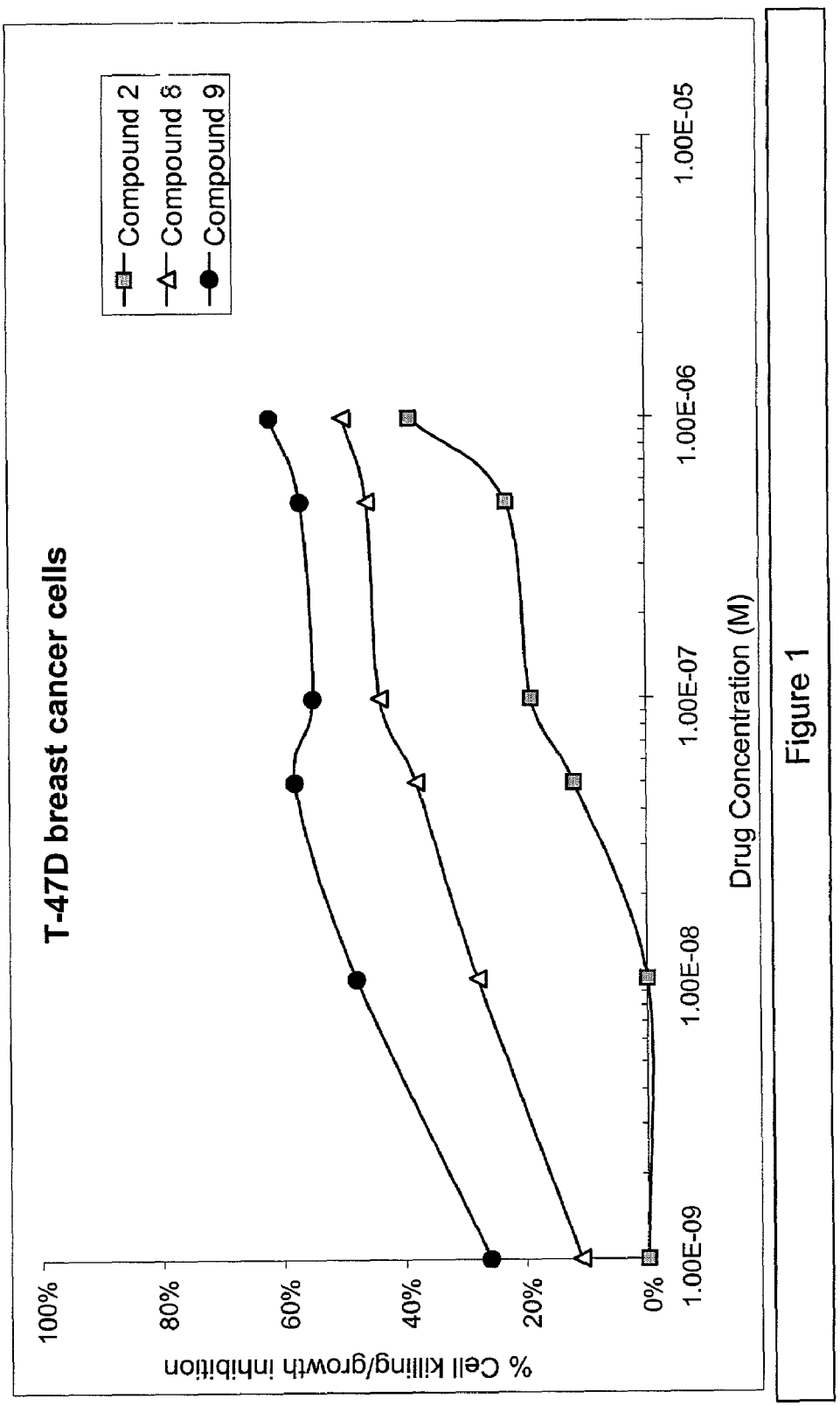
FIG. 1 shows the treatment of breast cancer cells (T47D) with compounds of the invention.

The present invention provides compounds that are useful, for example, to treat diseases of uncontrolled proliferation, for example for the treatment of cancers and precancerous conditions. The present invention may be understood more readily by reference to the following detailed description of preferred embodiments of the invention and the Examples included therein and to the Figures and their previous and following description. It is also to be understood that the terminology used herein is for the purpose of describing particular embodiments only and is not intended to be limiting.

DEFINITIONS

In the specification and Formulae described herein the following terms are hereby defined.

A residue of a chemical species, as used in the specification and concluding claims, refers to a structural fragment of a chemical species, or the moiety that is the resulting product of the chemical species in a particular reaction scheme or subsequent formulation or chemical product, regardless of whether the structural fragment or moiety is actually obtained from the chemical species. Thus, an ethylene glycol residue in a polyester refers to one or more —OCH₂CH₂O— repeat units in the polyester, regardless of whether ethylene glycol is used to prepare the polyester. Similarly, a 2,4-thiazolidinedione residue in a chemical compound refers to one or more -2,4-thiazolidinedione structural fragments or moieties of the compound, regardless of whether the residue was obtained by reacting 2,4-thiazolidinedione to obtain the compound.

It must be noted that, as used in the specification and the appended claims, the singular forms "a", "an" and "the" include plural referents unless the context clearly dictates otherwise. Thus, for example, reference to "an aromatic compound" includes mixtures of aromatic compounds.

Often, ranges are expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The term "alkyl" denotes a hydrocarbon group or residue which is structurally similar to a non-cyclic alkane compound modified by the removal of one hydrogen from the non-cyclic alkane and the substitution therefore of a non-hydrogen group or residue. Alkyls comprise a noncyclic, saturated, straight or branched chain hydrocarbon residue having from 1 to 18 carbons, or preferably 4 to 14 carbons, 5 to 13 carbons, 6 to 10 carbons, 6 to 18 carbons, 6 to 14 carbons, or 6 to 13 carbons. Examples of such alkyl radicals include methyl, ethyl, n-propyl, iso-propyl, n-butyl, sec-butyl, t-butyl, amyl, t-amyl, n-pentyl and the like. Lower alkyls comprise a noncyclic, saturated, straight or branched chain hydrocarbon residue having from 1 to 4 carbon atoms.

The term "substituted alkyl" denotes an alkyl radical analogous to the above definition that is further substituted with one, two, or more additional organic or inorganic substituent groups. Suitable substituent groups include but are not limited to hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkoxy, heteroaryl, substituted heteroaryl, aryl or substituted aryl. When more than one substituent group is present then they may be the same or different. The organic substituent groups may comprise from 1 to 12 carbon atoms, or from 1 to 6 carbon atoms, or from 1 to 4 carbon atoms.

The term "alkenyl" denotes an alkyl radical having 1 to 18 carbons, or preferably 4 to 14 carbons, 5 to 13 carbons, or 6 to 10 carbons further containing a carbon-carbon double bond. Examples of alkenyl radicals include but are not limited to vinyl, allyl, 2-butenyl, 3-butenyl, 2-pentenyl, 4-methyl-penten-2-yl, 3-pentenyl, 4-methyl-penten-3-yl, 4-pentenyl, 2-hexenyl, 3-hexenyl, 4-hexenyl, 5-hexanyl, 2-heptenyl, 3-heptenyl, 4-heptenyl, 5-heptenyl, 6-heptenyl, and like residues. The term "alkenyl" includes dienes and trienes and other polyunsaturated compounds. The alkenyl radical may exist as E or Z stereoisomers or as a mixture of E or Z stereoisomers. When more than one double bond is present, such as a diene or triene, each double bond may independently exist as E or Z stereoisomers or as a mixture of E or Z stereoisomers with respect to other double bond present in the alkenyl radical.

The term "substituted alkenyl" denotes a alkenyl radical of the above definition that is substituted with one, two, or more additional substituent groups from that may include halogen, hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy. When more than one substituent group is present then they may be the same or different. The organic substituent groups may comprise from 1 to 12 carbon atoms, or from 1 to 6 carbon atoms, or from 1 to 4 carbon atoms.

The term "alkynyl" denotes a radical containing a straight or branched chain of having 1 to 18 carbons, or preferably 4 to 14 carbons, 5 to 13 carbons, or 6 to 10 carbons, such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and like residues. The term "alkynyl" includes di- and tri-ynes.

The term "substituted alkynyl" denotes an alkynyl of the above definition that is substituted with one or more organic or inorganic groups, that may include halogen, hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy residues.

The term "cycloalkyl" denotes a hydrocarbon group or residue which is structurally similar to a cyclic alkane compound modified by the removal of one hydrogen from the cyclic alkane and substitution therefore of a non-hydrogen group or residue. Cycloalkyl groups, or residues contain 1 to 18 carbons, or preferably 4 to 14 carbons, 5 to 10 carbons, 5 to 6 carbons, 5 to 18 carbons, or 5 to 14 carbons, such as cyclopropyl, cyclobutyl, cyclopentyl, cyclopenyl, cyclohexyl, cycloheptyl, decahydronapthyl, adamantyl, and like residues.

The term "substituted cycloalkyl" denotes a cycloalkyl as defined above that is further substituted with one, two, or more additional organic or inorganic groups that may include but are not limited to halogen, alkyl, substituted alkyl, hydroxyl, alkoxy, substituted alkoxy, carboxy, carboalkoxy, alkylcarboxamide, substituted alkylcarboxamide, dialkylcarboxamide, substituted dialkylcarboxamide, amino, mono-substituted amino or di-substituted amino. When the cycloalkyl is substituted with more than one substitutent group, they may be the same or different. The organic substituent groups may comprise from 1 to 12 carbon atoms, or from 1 to 6 carbon atoms, or from 1 to 4 carbon atoms.

The term "cycloalkenyl" denotes a cycloalkyl radical further comprising at least one carbon-carbon double bond, including cyclopropenyl, 1-cyclobutenyl, 2-cyclobutenyl, 1-cyclopentenyl, 2-cyclopentenyl, 3-cyclopentenyl, 1-cyclohexyl, 2-cyclohexyl, 3-cyclohexyl, and like radicals.

The term "substituted cycloalkenyl" denotes a cycloalkenyl residues as defined above further substituted with one, two, or more additional substituent groups that may include halogen, alkyl, hydroxyl, alkoxy, substituted alkoxy, haloalkoxy, carboxy, carboalkoxy, alkylcarboxamide, substituted alkylcarboxamide, dialkylcarboxamide, substituted dialkylcarboxamide, amino, mono-substituted amino or di-substituted amino. When the cycloalkenyl is substituted with more than one group, they may be the same or different. The organic substituent groups may comprise from 1 to 12 carbon atoms, or from 1 to 6 carbon atoms, or from 1 to 4 carbon atoms.

The term "alkoxy" as used herein denotes a radical alkyl, defined above, attached directly to a oxygen to form an ether residue. Examples include methoxy, ethoxy, n-propoxy, iso-propoxy, n-butoxy, t-butoxy, iso-butoxy and the like.

The term "substituted alkoxy" denotes a alkoxy radical of the above definition that is substituted with one or more groups, but preferably one or two substituent groups including hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy. When more than one group is present then they may be the same or different. The organic substituent groups may comprise from 1 to 12 carbon atoms, or from 1 to 6 carbon atoms, or from 1 to 4 carbon atoms.

The term "mono-substituted amino" denotes an amino (—NH$_2$) group substituted with one group selected from alkyl, substituted alkyl or arylalkyl wherein the terms have the same definitions found herein.

The term "di-substituted amino" denotes an amino substituted with two radicals that may be same or different selected from aryl, substituted aryl, alkyl, substituted alkyl or arylalkyl wherein the terms have the same definitions found herein. Some examples include dimethylamino, methylethylamino, diethylamino and the like.

The term "haloalkyl" denotes a alkyl radical, defined above, substituted with one or more halogens, preferably fluorine, such as a trifluoromethyl, pentafluoroethyl and the like.

The term "haloalkoxy" denotes a haloalkyl, as defined above, that is directly attached to an oxygen to form a halogenated ether residue, including trifluoromethoxy, pentafluoroethoxy and the like.

The term "acyl" denotes a radical containing 1 to 8 carbons such as formyl, acetyl, propionyl, butanoyl, iso-butanoyl, pentanoyl, hexanoyl, heptanoyl, benzoyl and the like.

The term "acyloxy" denotes a radical containing 1 to 8 carbons of an acyl group defined above directly attached to an oxygen such as acetyloxy, propionyloxy, butanoyloxy, iso-butanoyloxy, benzoyloxy and the like.

The term "aryl" denotes an ring radical containing 6 to 18 carbons, or preferably 6 to 12 carbons, having at least one six-membered aromatic "benzene" residue therein. Examples of such aryl radicals include phenyl and naphthyl. The term "substituted aryl" denotes an aryl ring radical as defined above that is substituted with one or more, or preferably 1, 2, or 3 organic or inorganic substituent groups, which include but are not limited to a halogen, alkyl, substituted alkyl, hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy, aryl, substituted aryl, heteroaryl, heterocyclic ring, substituted heterocyclic ring wherein the terms are defined herein. The organic substituent groups may comprise from 1 to 12 carbon atoms, or from 1 to 6 carbon atoms, or from 1 to 4 carbon atoms.

The term "heteroaryl" denotes an aryl ring radical as defined above, wherein at least one of the carbons, or preferably 1, 2, or 3 carbons of the aryl aromatic ring has been replaced with a heteroatom, which include but are not limited to nitrogen, oxygen, and sulfur atoms. Examples of heteroaryl residues include pyridyl, bipyridyl, furanyl, and thiofuranyl residues. Further examples of heteroaryl residues which may be employed in the chemical structures of the invention include but are not limited to the residues exemplified in the structural drawings shown below. In the structures shown by the drawings, R can be hydrogen, alkyl, substituted alkyl, aryl, substituted aryl, and the like. It is to be understood that the above "heteroaryl" radicals or residues may have one or more organic or inorganic substituent groups, or preferably 1, 2, or 3 such groups, as referred to herein-above for aryl groups, bound to the carbon atoms of the heteroaromatic rings. The organic substituent groups may comprise from 1 to 12 carbon atoms, or from 1 to 6 carbon atoms, or from 1 to 4 carbon atoms.

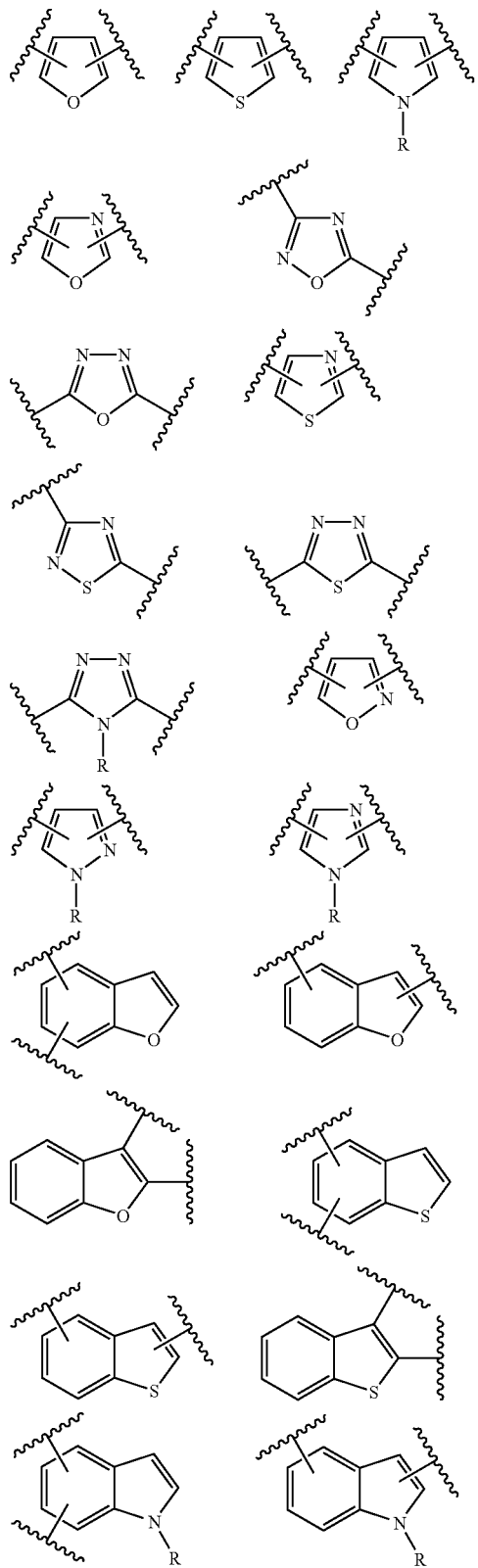

The term "heterocyclic" denotes a non-aromatic cycloalkyl or cycloalkenyl residue as defined above, wherein at least one of the ring carbons, or preferably 1, 2, or 3 carbons of the cycloalkyl or cycloalkenyl ring carbons has been replaced with a heteroatom, which include but are not limited to nitrogen, oxygen, and sulfur atoms. Examples of heterocyclic residues include piperidine, tetrahydrofuranyl, tetrahydrothiophene, and like residues.

The term "substituted heterocyclic" denotes a heterocyclic residue as defined above, that is further substituted with one or more, or preferably 1, 2, or 3 organic or inorganic substituent groups, which include but are not limited to a halogen, alkyl, substituted alkyl, hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy, aryl, substituted aryl, heteroaryl, heterocyclic ring, substituted heterocyclic ring wherein the terms are defined herein. The organic substituent groups may comprise from 1 to 12 carbon atoms, or from 1 to 6 carbon atoms, or from 1 to 4 carbon atoms.

The term "halo" or "halogen" refers to a fluoro, chloro, bromo or iodo group.

The term "thioalkyl" denotes a sulfide radical containing 1 to 8 carbons, linear or branched. Examples include methylsulfide, ethyl sulfide, isopropylsulfide and the like.

The term "thiohaloalkyl" denotes a thioalkyl radical substituted with one or more halogens. Examples include trifluoromethylthio, 1,1-difluoroethylthio, 2,2,2-trifluoroethylthio and the like.

The term "carboalkoxy" refers to an alkyl ester of a carboxylic acid, wherein alkyl has the same definition as found above. Examples include carbomethoxy, carboethoxy, carboisopropoxy and the like.

The term "alkylcarboxamide" denotes a single alkyl group attached to the amine of an amide, wherein alkyl has the same definition as found above. Examples include N-methylcarboxamide, N-ethylcarboxamide, N-(iso-propyl)carboxamide and the like.

The term "substituted alkylcarboxamide" denotes a single "substituted alkyl" group, as defined above, attached to the amine of an amide.

The term "dialkylcarboxamide" denotes two alkyl or arylalkyl groups that are the same or different attached to the amine of an amide, wherein alkyl has the same definition as found above. Examples of a dialkylcarboxamide include N,N-dimethylcarboxamide, N-methyl-N-ethylcarboxamide and the like. The term "substituted dialkylcarboxamide" denotes two alkyl groups attached to the amine of an amide, where one or both groups are a "substituted alkyl", as defined above. It is understood that these groups may be the same or different. Examples include N,N-dibenzylcarboxamide, N-benzyl-N-methylcarboxamide and the like.

The term "alkylamide" denotes an acyl radical attached to an amine or monoalkylamine, wherein the term acyl has the same definition as found above. Examples of "alkylamide" include acetamido, propionamido and the like.

The term "alkylene" as used herein refers to a difunctional saturated branched or unbranched hydrocarbon chain containing from 1 to 36 carbon atoms, and includes, for example, methylene (—CH$_2$—), ethylene (—CH$_2$—CH$_2$—), propylene (—CH$_2$—CH$_2$(CH$_3$)—), 2-methylpropylene [—CH$_2$—CH(CH$_3$)—CH$_2$—], hexylene [—(CH$_2$)$_6$—] and the like. "Lower alkylene" refers to an alkylene group of from 1 to 6, more preferably from 1 to 4, carbon atoms. The term "cycloalkylene" as used herein refers to a cyclic alkylene group, typically a 5- or 6-membered ring.

The term "arylalkyl" defines an alkylene as described above which is substituted with an aryl group that may be substituted or unsubstituted as defined above. Examples of an "arylalkyl" include benzyl, phenethylene and the like.

Compounds

Some disclosed embodiments of the invention relate to certain heterocyclic compounds and compositions derived therefrom having the Formula (I):

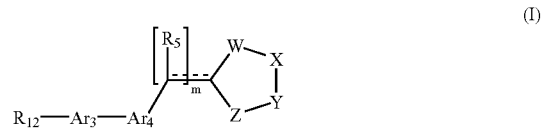

wherein:
(a) m is an integer 0 or 1;
(b) R$_{12}$ is an alkyl or substituted alkyl residue comprising 6 to 18 carbon atoms; or a cycloalkyl, a substituted cycloalkyl, a heterocyclic, a substituted heterocyclic, a heteroaryl, a substituted heteroaryl, an aryl or a substituted aryl residue comprising 5 to 18 carbon atoms;
(c) Ar$_3$ is an aryl, a substituted aryl, a heteroaryl or a substituted heteroaryl residue;
(d) Ar$_4$ is an aryl, a substituted aryl, a heteroaryl or a substituted heteroaryl residue;
(e) R$_5$ is hydrogen, hydroxy, alkyl or substituted alkyl;
(f) ----- represents a bond present or absent; and
(g) W, X, Y and Z are independently or together —C(O)—, C(S), S, O, or NH;

or a pharmaceutically acceptable salt thereof.

The heterocyclic ring comprising W, X, Y and Z residues may independently or together comprise —C(O)—, C(S), S, O, or NH residues, so as to form numerous known or unknown heterocyclic rings. In some embodiments, the W, X, Y and Z residues are selected to form 2,4-thiazolidinedione, 2-thioxo-4-thiazolidinedione, isoxazolidinedione, 2,4-imidazolidinedione or 2-thioxo-4-imidazolidinedione residues, which may be illustrated by the following structural formulae:

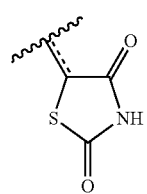

2,4-thiazolidinedione

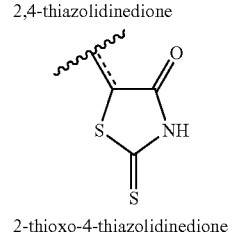

2-thioxo-4-thiazolidinedione

-continued

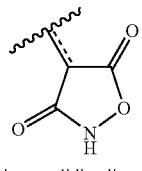
isoxazolidinedione

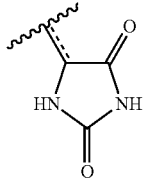
2,4-imidazolidinedione

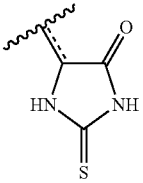
2-thioxo-4-imidazolidinedione

The heterocyclic residues may simultaneously exist in various tautomeric forms. For example, 2,4-thiazolidinedione-containing compounds disclosed herein may exist in the form of tautomers such as those shown immediately below.

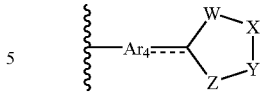

An example of one of the compounds of the invention having such a structural fragment is

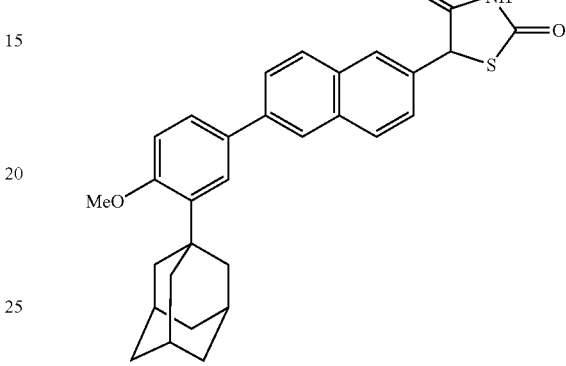

5-[6-(3-[1-Adamantyl]-4-methoxyphenyl)-naphthalen-2-yl]-2,4-thiazolidinedione.

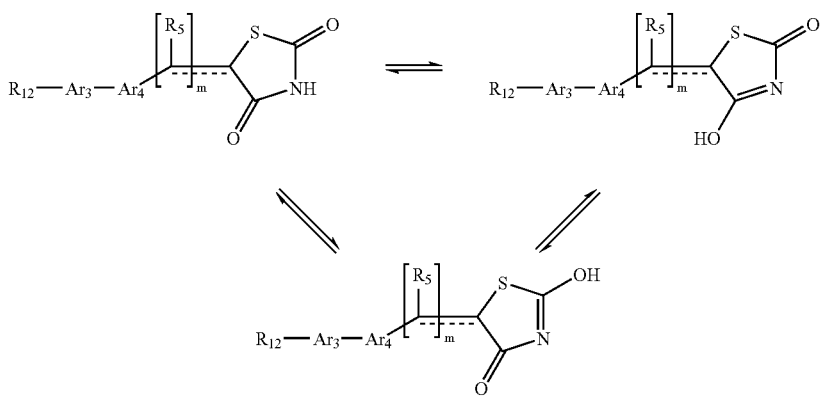

It is understood by those of skill in the art that tautomers may also exist with 2-thioxo-4-thiazolidinedione, 2,4-imidazolidinedione, 2-thioxo-4-imidazolidinedione and isoxazolidinedione containing compounds disclosed herein. For convenience, all of the tautomers may be presented herein by a single formula, but it is understood that all tautomers are within the scope of the invention.

It is also to be understood the that the integer "m" of the chemical formulas of the invention may be either 0 or 1, i.e., the carbon bearing an $R_5$ substituent may either be present or absent. If m is zero, the carbon bearing the $R_5$ substituent is absent, and the carbon of the heterocyclic ring comprising the W, X, Y and Z groups is bonded directly to a ring atom of the $Ar_4$ group, as shown below.

If m is one, the carbon bearing the $R_5$ substituent is present, and the carbon of the heterocyclic ring comprising the W, X, Y and Z groups is bonded to a methylene or methine carbon atom, which is itself bonded to a ring atom of the $Ar_4$ group, as shown below.

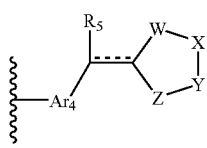

If the carbon bearing the $R_5$ substituent is present, then ----- represents a bond that is either present or absent, i.e., there may be either a single carbon-carbon bond or a double carbon-carbon bond between the methylene or methine carbon bearing the $R_5$ substituent and the heterocyclic residue. If a carbon-carbon double bond is present, the following structural fragment might (for example) result:

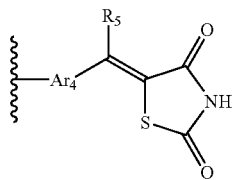

An exemplary compound of the invention possessing such a carbon-carbon double bond is:

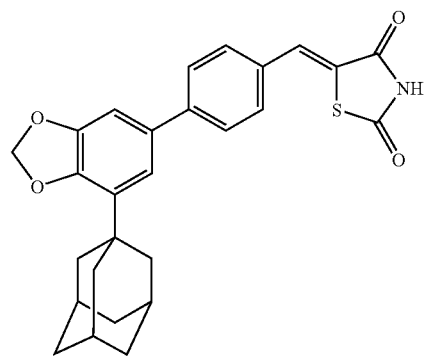

4-[3-(1-Adamantyl)-4,5-methylenedioxyphenyl]-benzylidene-2,4-thiazolidinedione.

Another exemplary compound of the invention possessing such a carbon-carbon double bond is:

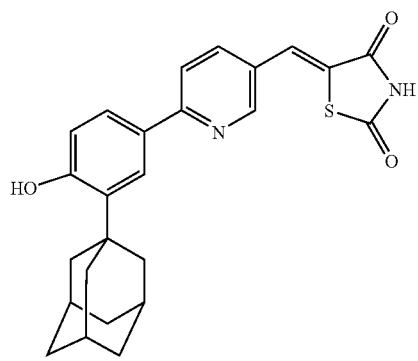

6-[3-(1-Adamantyl)-4-hydroxy-phenyl]-pyridin-3-ylmethylene]-thiazolidine-2,4-dione.

When ----- is present both E and Z configurations are within the scope of the invention. For example, 2,4-thiazolidinedione and 2-thioxo-4-thiazolidinediones of Formula (I) may have the following structures respectively:

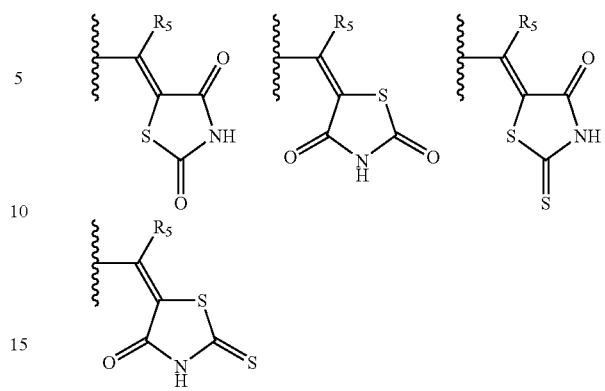

If the relevant carbon-carbon double bond is absent, the corresponding exemplary structural fragment has a carbon-carbon single bond, and a methine carbon having a carbon-hydrogen bond results:

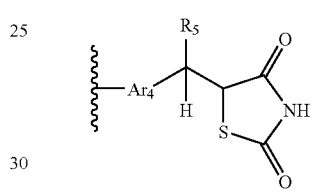

$R_5$ may be hydrogen, hydroxy, alkyl or substituted alkyl. In some preferred embodiments, $R_5$ is hydrogen.

$Ar_4$ is an (at least) divalent organic aromatic radical that may be (1) bonded to $Ar_3$, or a bridging "A" group (as discussed below), and (2) is also bonded to at least one of a methylene or methine carbon, or the heterocyclic ring comprising W, X, Y and Z residues, as discussed above. The divalent $Ar_4$ radical may be bonded to the two other groups in any of the possible combinations of geometric isomers that are available for the particular $Ar_4$ radical specified. In many embodiments, $Ar_4$ comprises at least one aromatic ring, such as an aryl, a substituted aryl, a heteroaryl or a substituted heteroaryl residue, as may be understood by reference to the definitions of these terms included hereinabove.

As indicated by the "substituted" terminology, $Ar_4$ may optionally have one or more, and preferably between one and four organic or inorganic substitutent groups. For example, in some embodiments $Ar_4$ may have the formula:

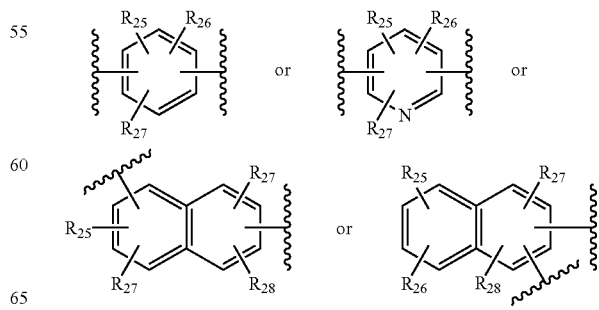

wherein $R_{25}$, $R_{26}$, $R_{27}$ and $R_{28}$ are independently or together hydrogen, an alkyl, a substituted alkyl, an alkenyl, a substituted alkenyl, an alkynyl, a substituted alkynyl, a cycloalkyl, a substituted cycloalkyl, a heterocyclic, a substituted heterocyclic, an alkoxy, a substituted alkoxy, a hydroxyl, an acyl, an amino, a mono-substituted amino, a di-substituted amino, a carboxy, a carboalkoxy, an alkylcarboxamide, a substituted alkylcarboxamide, a dialkylcarboxamide, a substituted dialkylcarboxamide, a haloalkoxy, a heteroaryl, a substituted heteroaryl, an aryl, a substituted aryl; or two adjacent groups together with the aromatic ring form a cycloalkyl, substituted cycloalkyl, cycloalkenyl or substituted cycloalkenyl optionally comprising 1 or 2 heteroatomic residues selected from O, S, NH, N-alkyl and N-substituted alkyl residues. Without wishing to be bound by theory, it is to be understood that the compounds of the invention are believed to bind to the binding pockets of certain receptor proteins as described elsewhere herein, and those binding pockets may in some cases be of limited physical size. Therefore, in many embodiments, $Ar_4$ and the $R_{25}$, $R_{26}$, $R_{27}$ and/or $R_{28}$ organic substituent groups or residues bound thereto are of limited size, so as to together comprise from 3 to 18 carbon atoms, or preferably from 5 to 15 carbon atoms, or from 6 to 12 carbon atoms.

In some embodiments, $Ar_4$ is an aryl, a substituted aryl, a heteroaryl, or a substituted heteroaryl residue comprising a ring structure having one of the below-indicated structural and/or geometrical formulas:

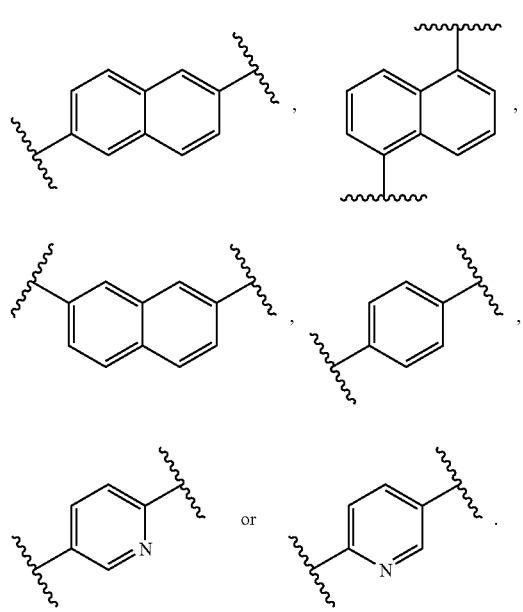

In some embodiments, $Ar_4$ may comprise;

(1) an aryl or substituted aryl residue of the formula;

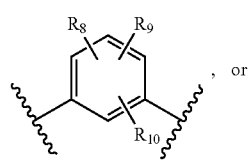, or (2) a heteroaryl or substituted heteroaryl of the formula:

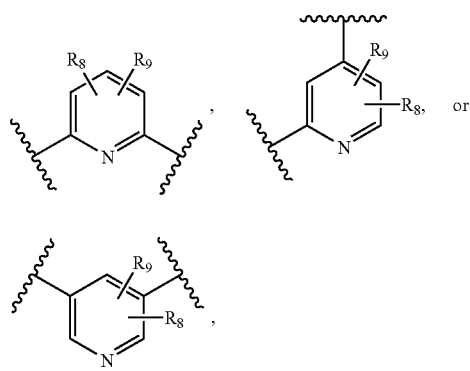

wherein $R_8$ $R_9$ and $R_{10}$ are independently or together hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylamide, alkylsulfonamide, arylsulfonamide, alkylurea, arylurea, alkylcarbamate, arylcarbamate, alkoxy, substituted alkoxy, haloalkoxy, thioalkyl, thiohaloalkyl, carboxy, carboalkoxy, alkylcarboxamide, substituted alkylcarboxamide, dialkylcarboxamide or substituted dialkylcarboxamide.

Nevertheless, in certain other embodiments, $Ar_4$ does not comprise;

(1) an aryl or substituted aryl residue of the formula;

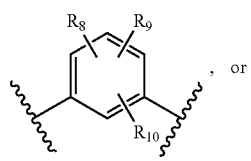, or (2) a heteroaryl or substituted heteroaryl of the formula:

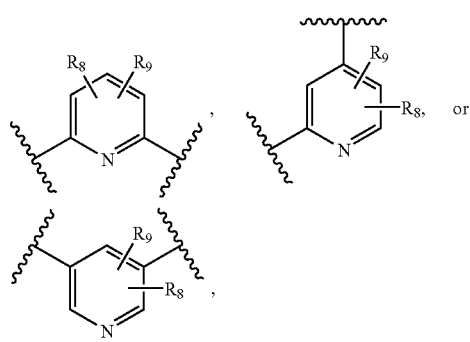

wherein $R_8$, $R_9$ and $R_{10}$ are as defined above.

In the compounds of the invention, $Ar_3$ is an at least divalent organic aromatic radical that is bonded to at least one $R_{12}$ substituent, as well as being bound to either an $Ar_4$ or a bridging "A" group (as discussed and shown below).

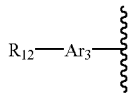

In many embodiments, the $Ar_3$ radical is an aryl, a substituted aryl, a heteroaryl or a substituted heteroaryl residue, and $R_{12}$ is an alkyl, a substituted alkyl, a cycloalkyl, a substituted cycloalkyl, a heterocyclic, a substituted heterocyclic, a heteroaryl, a substituted a heteroaryl, an aryl or a substituted aryl residue. The $R_{12}$ residue and/or any other substituents on the $Ar_3$ residue may be bound in any isomeric or geometric pattern that is chemically stable for the particular $Ar_3$ ring residue selected, relative to any other substituents on the $Ar_3$ ring residue, so long at the isomeric or geometric pattern of substituents does not impair the biological activity of the resulting compounds.

It has been found that the number, geometry, and size of the $R_{12}$ and/or other substituents of the $Ar_3$ ring can have an unexpectedly strong effect on the biological activity of the resulting compounds in general, and on their activity as anti-cancer agents in particular.

Therefore, it in many preferred embodiments, $Ar_3$ is an aromatic ring residue having the formula:

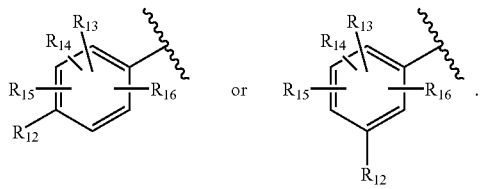

wherein $R_{12}$ is an alkyl, a substituted alkyl, a cycloalkyl, a substituted cycloalkyl, a heterocyclic, a substituted heterocyclic, a heteroaryl, a substituted a heteroaryl, an aryl or a substituted aryl residue. Without wishing to be bound by theory, it is to be understood that the compounds of the invention are believed to bind to the binding pockets of certain receptor proteins as described elsewhere herein, and those binding pockets may in some cases be of limited physical size. Therefore, in many embodiments, $Ar_3$ and the organic substituent groups or residues bound thereto together comprise from 10 to 25 carbon atoms, or preferably from 11 to 20 carbon atoms, or from 12 to 19 carbon atoms.

The "para", or "meta" relationship of the $R_{12}$ substituent bound to the $Ar_3$ ring relative to the $Ar_4$ and/or "A" residues can have a significant effect on the anti-cancer activity of the inventive compounds. In some embodiments, a "meta" relationship of the $R_{12}$ substitutent relative to the $Ar_4$ substitutent is preferred for giving good anti-cancer activity.

Preferably, $Ar_3$ and $R_{12}$ do not together form a substituted or unsubstituted 5,6,7,8-tetrahydro-2-napthyl residue, a substituted or unsubstituted 1,2,3,4-tetrahydro-6-quinolinyl residue, or a substituted or unsubstituted 1,2,3,4-tetrahydro-7-quinoxalinyl residue. Similarly, in some embodiments, $R_{12}$ together with the $Ar_3$ aromatic ring and any additional substituents bonded thereto do not form a cycloalkyl, substituted cycloalkyl, cycloalkenyl or substituted cycloalkenyl residue that may optionally comprise 1 or 2 heteroatoms selected from O, S, NH or N-alkyl.

$Ar_3$ may also optionally have from one to four other organic or inorganic $R_{13}$, $R_{14}$, $R_{15}$ and $R_{16}$ substituent groups, which may be isomerically or geometrically bonded to $Ar_3$ in any chemically stable manner. For example, in some embodiments, $R_{13}$, $R_{14}$, $R_{15}$ and/or $R_{16}$ are independently or together hydrogen, an alkyl, a substituted alkyl, an alkenyl, a substituted alkenyl, an alkynyl, a substituted alkynyl, a cycloalkyl, a substituted a cycloalkyl, a heterocyclic, a substituted heterocyclic, an alkoxy, a substituted alkoxy, a hydroxyl, an acyl, an amino, a mono-substituted amino, a di-substituted amino, carboxy, a carboalkoxy, a nitrile an alkylcarboxamide, a substituted an alkylcarboxamide, a dialkylcarboxamide, a substituted dialkylcarboxamide, a haloalkoxy, a triorganosilyloxy, a heteroaryl, a substituted heteroaryl, an aryl, or a substituted aryl residue.

In certain embodiments, the presence of at least one of the additional $R_{13}$, $R_{14}$, $R_{15}$ and $R_{16}$ substituent groups substitutent group comprising one or more alkoxy, substituted alkoxy, or hydroxyl residues can be beneficial to the biological activity of the compounds, particularly if the oxygen atom is oriented para to the $Ar_4$ ring, and ortho to the $R_{12}$ group as shown below.

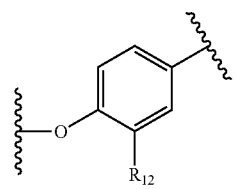

Moreover, in some embodiments the presence of a bridging alkylene-dioxy ring adjacent to the $R_{12}$ group is beneficial, as shown below.

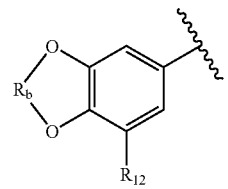

wherein the Rb group is substituted or unsubstituted alkylene group comprising from 1 to 6 carbon atoms.

Examples of $Ar_3$ groups comprising $R_{12}$ groups and oxygen containing substituents include the hydroxy, methoxy, and methylenedioxy substituted $Ar_3$ groups shown below:

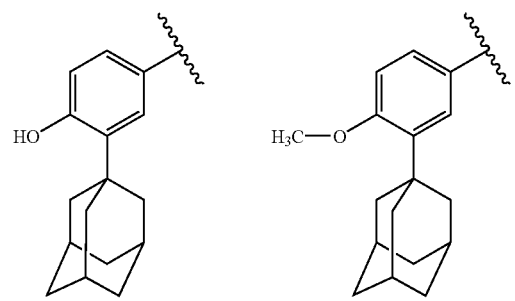

-continued

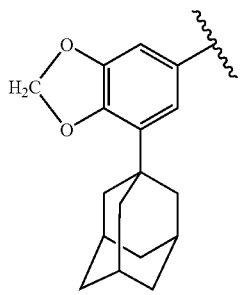

In some embodiments, biological activity of the compounds of the invention may be improved if two adjacent $R_{13}$, $R_{14}$, $R_{15}$ and/or $R_{16}$ substituent groups comprise oxygen atoms bound together by an alkylene or substituted alkylene ring, so as to form an alkylene-dioxy ring attached to the $Ar_3$ ring. An example of such an embodiment would include the following structure:

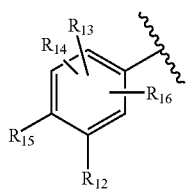

In certain embodiments, $Ar_3$ is an aromatic ring residue having the formula:

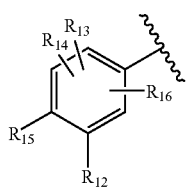

wherein $R_{12}$ and $R_{13}$, $R_{14}$, $R_{15}$ and/or $R_{16}$ are as defined above, with the proviso that $R_{15}$ is not an alkyl, or a substituted alkyl residue, and does not form, together with $R_{12}$, a cyclic aliphatic or aromatic residue. Similarly, in some embodiments, $R_{12}$ and $R_{15}$ together with the $AR_3$ aromatic ring bonded thereto do not form a cycloalkyl, substituted cycloalkyl, cycloalkenyl or substituted cycloalkenyl residue that may optionally comprise 1 or 2 heteroatoms selected from O, S, NH or N-alkyl.

The chemical, physical, and structural properties of the $R_{12}$ substituent have also been found to be of unexpected significance with respect to the anti-cancer activity of the inventive compounds. In particular, although not wishing to be bound by theory, it has been found that relatively bulky (i.e. sterically demanding) and non-polar $R_{12}$ substituents may produce unexpectedly high anti-cancer activity in the resulting heterocyclic compounds. One method to provide a sterically demanding and non-polar $R_{12}$ substituent group, is to provide $R_{12}$ in the form of an alkyl, substituted alkyl, cycloalkyl, substituted cycloalkyl, heterocyclic or substituted heterocyclic ring compound with a selected number of carbon atoms so as to provide desirable steric demands and/or steric bulk, but wherein the substitutent group is not so large as to exclude the compound from the desired binding pockets. Therefore, in some embodiments, the $R_{12}$ group may have from 4 to 25 carbon atoms. Preferably the $R_{12}$ group has from 5 to 20 carbon atoms, or 6 to 18 carbon atoms, or from 6 to 15 carbon atoms, or from 7 to 15 carbon atoms.

Moreover, steric bulk can be provided in the $R_{12}$ substituent group by having the carbon atoms present as branched chains having secondary and/or tertiary carbon atoms, rather than straight chain hydrocarbon compounds that comprise only primary carbon atoms. Therefore, in some preferred embodiments, the $R_{12}$ substituent has the formula

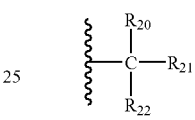

wherein $R_{20}$, $R_{21}$, and $R_{22}$ can be independently selected from hydrogen, alkyl, substituted alkyl, cycloalkyl, substituted cycloalkyl, heterocyclic or substituted heterocyclic ring. Preferably, at least two of the $R_{20}$, $R_{21}$, and $R_{22}$ substituents have carbon atoms bound to the $R_{12}$ carbon atom, and no more than one of $R_{20}$, $R_{21}$, and $R_{22}$ are hydrogen, so as to form at least a secondary $R_{12}$ group. For example, $R_{20}$ and $R_{21}$ may both comprise alkyl groups, while $R_{22}$ is hydrogen. Alternatively, $R_{20}$ and $R_{21}$ may, together with the illustrated carbon atom, form a cycloalkyl, substituted cycloalkyl, heterocyclic or substituted heterocyclic ring, while $R_{22}$ is an independent substituent as defined above. In another embodiment, $R_{20}$ and $R_{21}$ together with the carbon atom may form an aryl, a substituted aryl, a heteroaryl, or a substituted heteroaryl ring, and $R_{22}$ would be absent.

Even more preferably, none of $R_{20}$, $R_{21}$, and $R_{22}$ are hydrogen, and $R_{12}$ therefore comprises a tertiary carbon atom and/or a tertiary group. Nevertheless, in many embodiments, the $R_{12}$ group comprises at least 5 or 6 carbon atoms, and therefore does not comprise butyl or pentyl groups, such as a t-butyl group or a t-amyl group.

In certain preferred embodiments, $R_{12}$ is a phenyl, a 2-pyridyl, a 3-pyridyl, a 4-pyridyl, a 1-alkylcyclohexyl, or an adamantyl residue.

In certain preferred embodiments $R_{12}$ is a 2-pyridyl, a 3-pyridyl, a 4-pyridyl, a 1-methylcyclohexyl, or an adamantyl residue. In certain embodiments $R_{12}$ does not comprise a t-butyl, or a phenyl residue.

Additionally, one or more of $R_a$, $R_b$, and $R_c$ may be a heteroatom such as oxygen, nitrogen, sulfur, phosphorus, or the like, or heteroatomic radical such as alkoxy, mono or di-substituted amino groups and the like. One of skill in the art will also recognize that the secondary or tertiary carbon atom bonded to the $Ar_3$ ring could be replaced with a silicon, nitrogen, phosphorus, or similar heteroatoms.

The bulky $R_{12}$ substituent radical may be a substituted radical of the Formula:

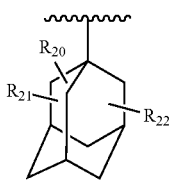

wherein:

$R_{20}$, $R_{21}$ and $R_{22}$ are at any position on the ring radical and are independently hydrogen, halogen, alkyl, hydroxy, carboxyl, alkylcarboxamide or dialkylcarboxamide. In one embodiment $R_{20}$, $R_{21}$ and $R_{22}$ are hydrogen, such that the substituted cycloalkyl is an adamantyl radical of the Formula:

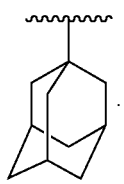

In another embodiment the bulky substituent radical is a substituted adamantyl radical wherein $R_{20}$ is a fluorine. An example is a radical of the formula:

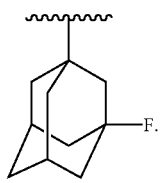

Some embodiments of the invention relate to compounds wherein the bulky substituent radical is a substituted heterocyclic radical of the formula:

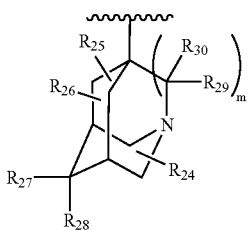

wherein:

m is 0 or 1;

$R_{24}$, $R_{25}$ and $R_{26}$ can be attached to any carbon on the substituted heterocyclic radical except for the carbons bearing $R_{27}$ and $R_{28}$ or $R_{29}$ and $R_{30}$ and are independently hydrogen, halogen, alkyl, hydroxy, carboxyl, alkylcarboxamide or dialkylcarboxamide;

$R_{27}$ and $R_{28}$ are independently hydrogen, halogen, or hydroxy; or $R_{27}$ and $R_{28}$ together form a carbonyl radical;

$R_{29}$ and $R_{30}$ are independently hydrogen; or $R_{29}$ and $R_{30}$ together form a carbonyl radical.

In one embodiment the bulky substituent radical is a substituted heterocyclic radical wherein m is 0; $R_{24}$, $R_{25}$ and $R_{26}$ are hydrogen; $R_{27}$ and $R_{28}$ are each hydrogen or $R_{27}$ and $R_{28}$ together form a carbonyl radical of the following formulae:

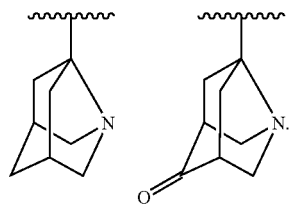

In one embodiment, the bulky substituent radical is a substituted heterocyclic radical wherein m is 1, $R_{24}$ and $R_{25}$ are independently an alkyl, $R_{26}$ is hydrogen and $R_{27}$ and $R_{28}$ are each a hydrogen or $R_{27}$ and $R_{28}$ together form a carbonyl of the following formulae:

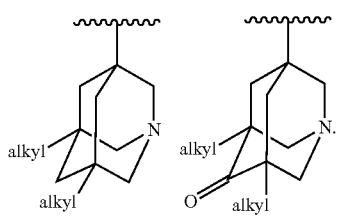

In one embodiment, the bulky substituent radical is a substituted heterocyclic radical wherein m is 1; $R_{24}$, $R_{25}$ and $R_{26}$ are hydrogen; $R_{27}$ and $R_{28}$ are hydrogen or $R_{27}$ and $R_{28}$; and $R_{29}$ and $R_{30}$ together form a carbonyl of the following formulae:

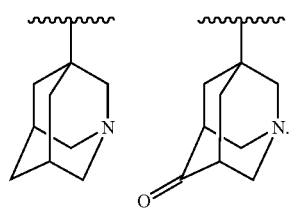

Figure 12:
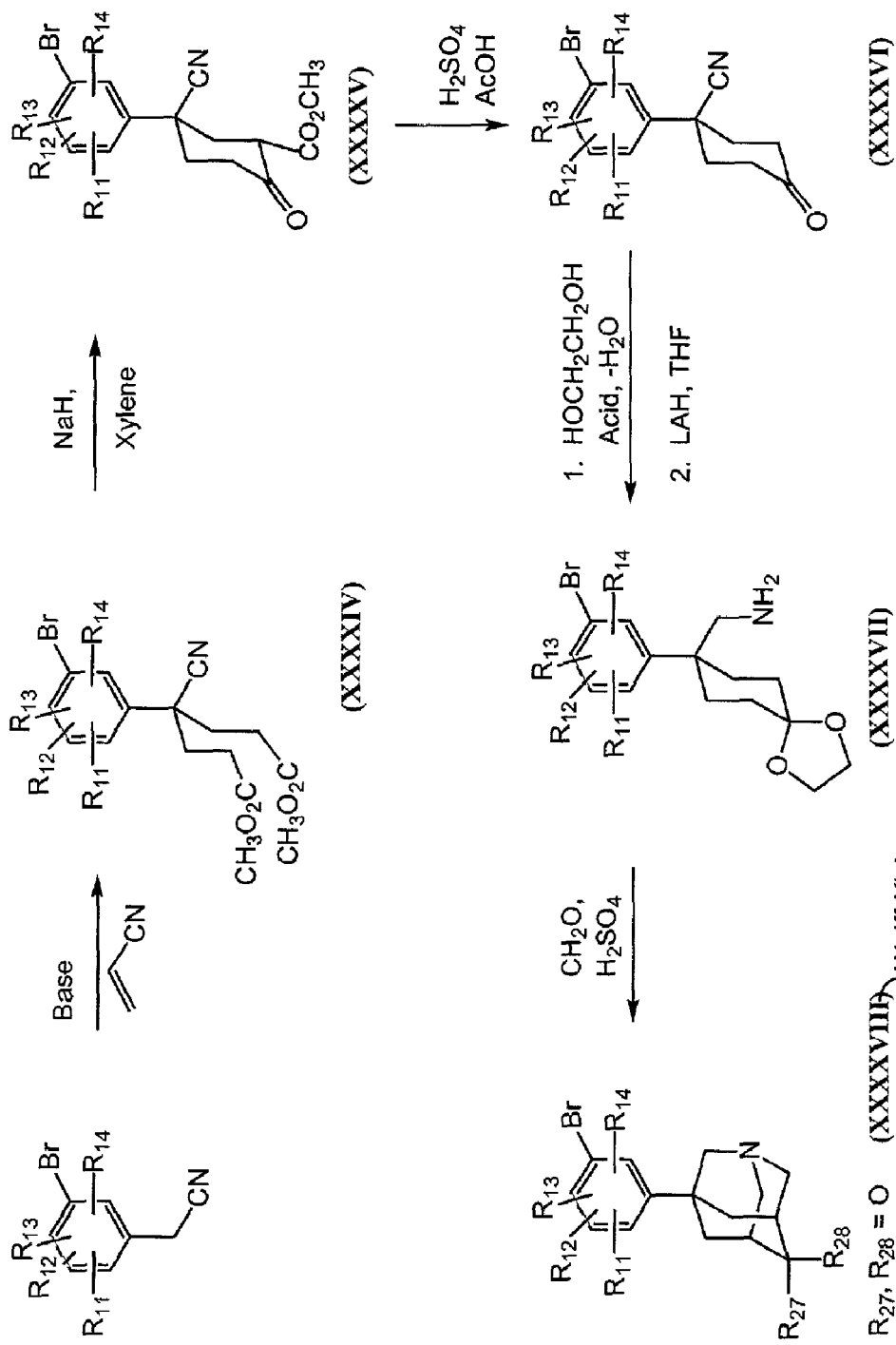
FIG. 12 shows methods for preparing intermediates suitable for preparation of compounds containing heterocyclic adamantyl derivatives.
Figure 13:
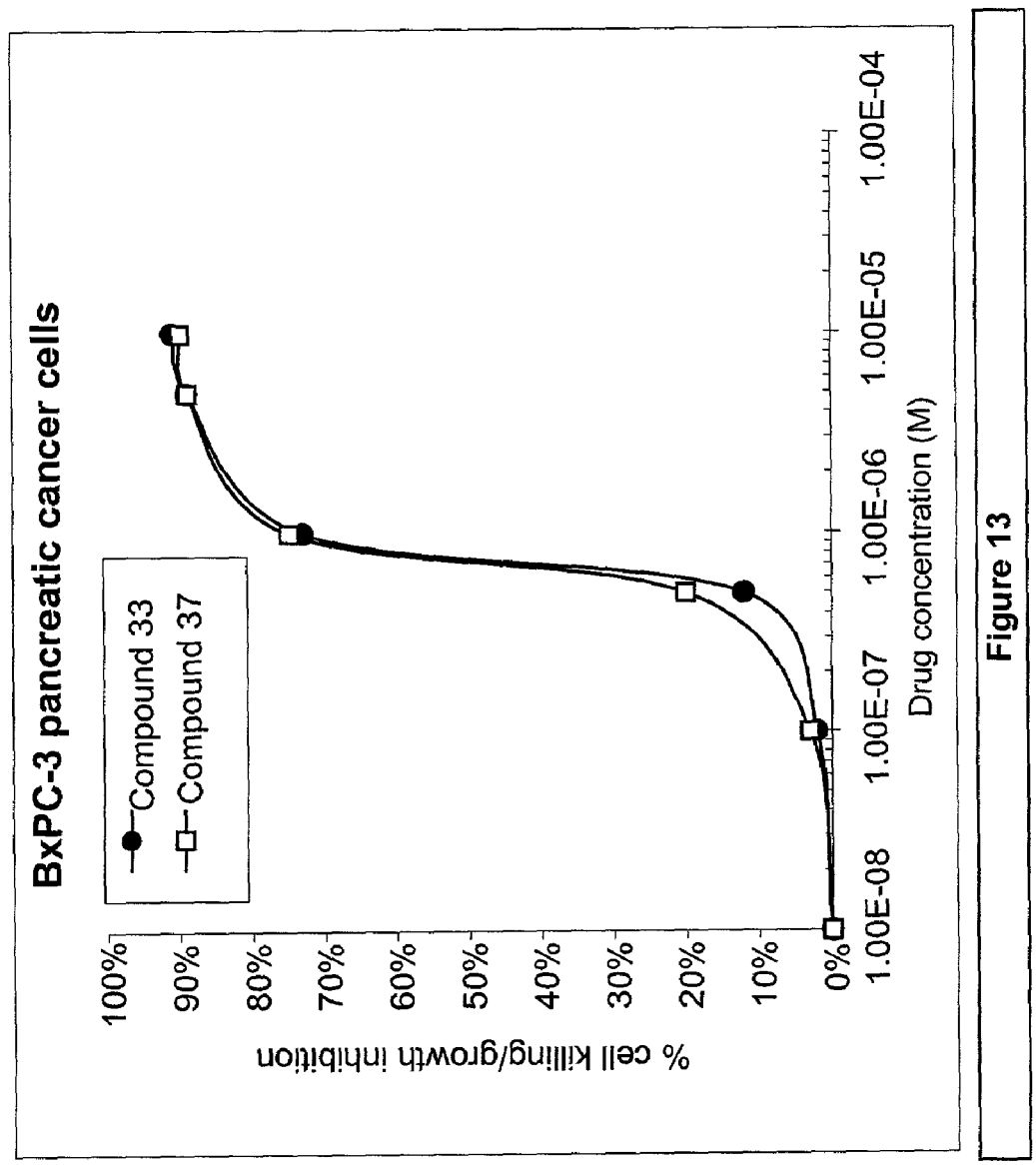
FIG. 13 shows the treatment of pancreatic cancer cells (BxPC-3) with compounds of the invention.
Figure 14:
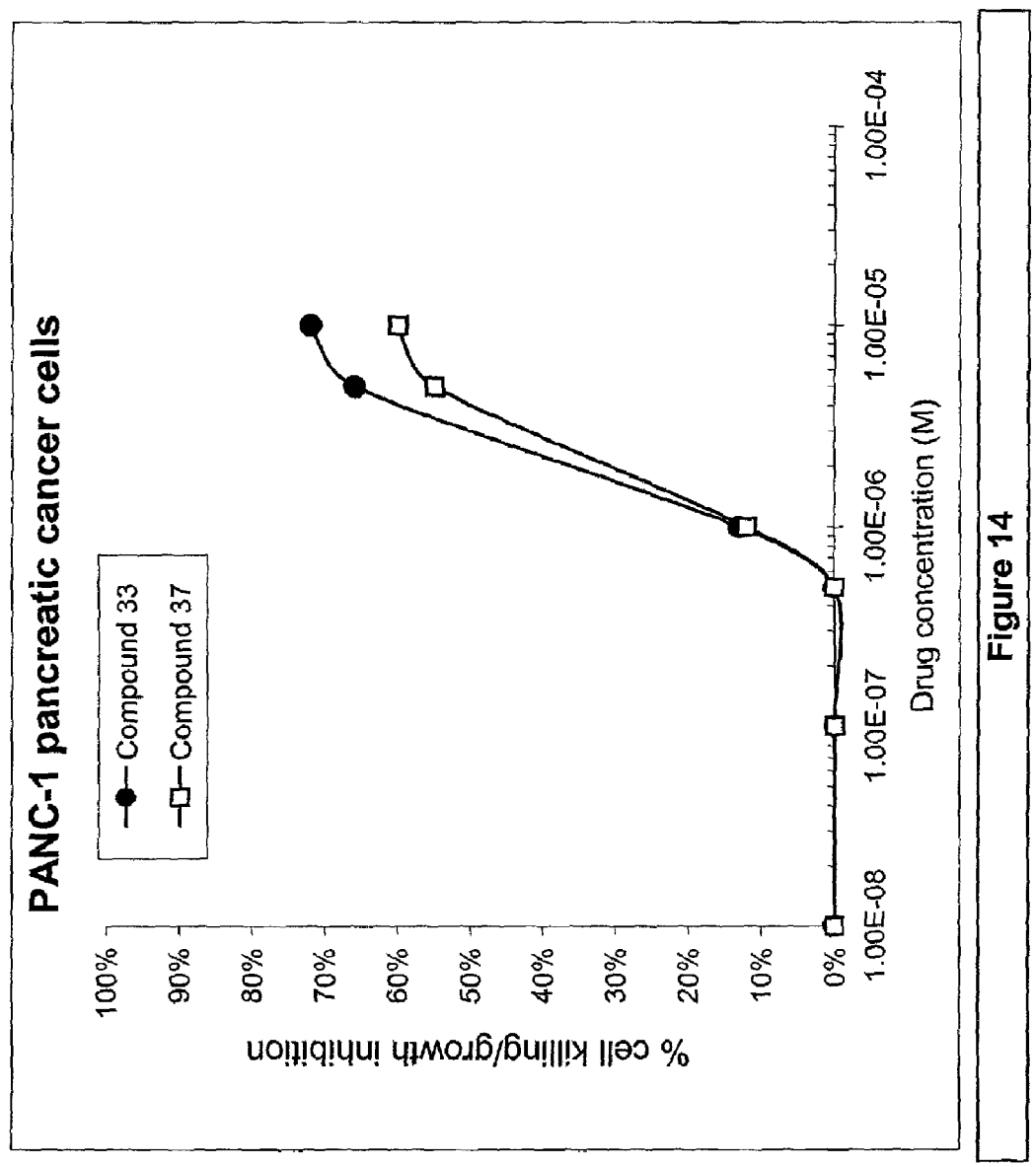
FIG. 14 shows the treatment of pancreatic cancer cells (PANC-1) with compounds of the invention.
Figure 15:
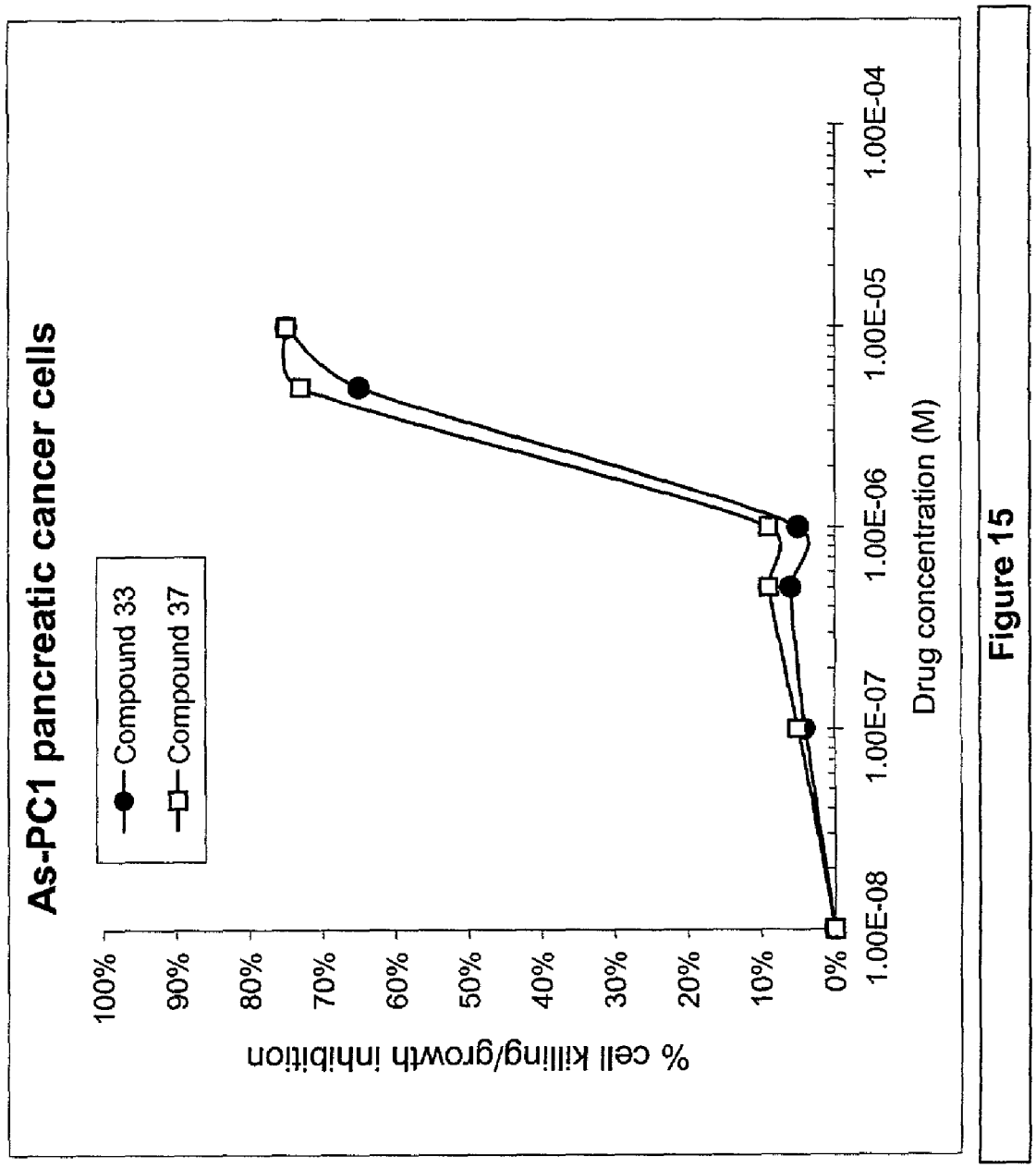
FIG. 15 shows the treatment of pancreatic cancer cells (As-PC1) with compounds of the invention.
Figure 16:
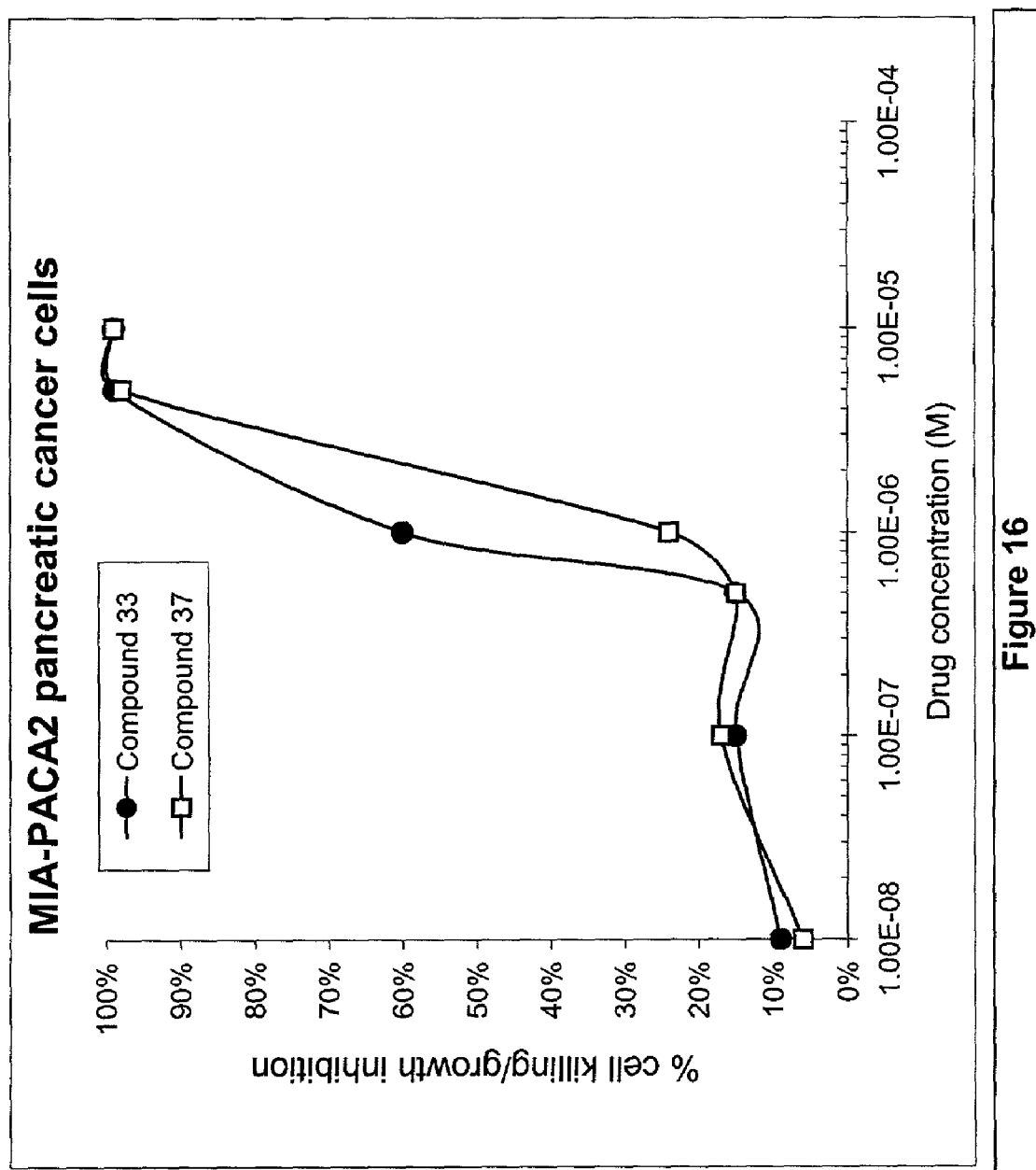
FIG. 16 shows the treatment of pancreatic cancer cells (MIA-PACA2) with the compounds of the invention.
Figure 17:
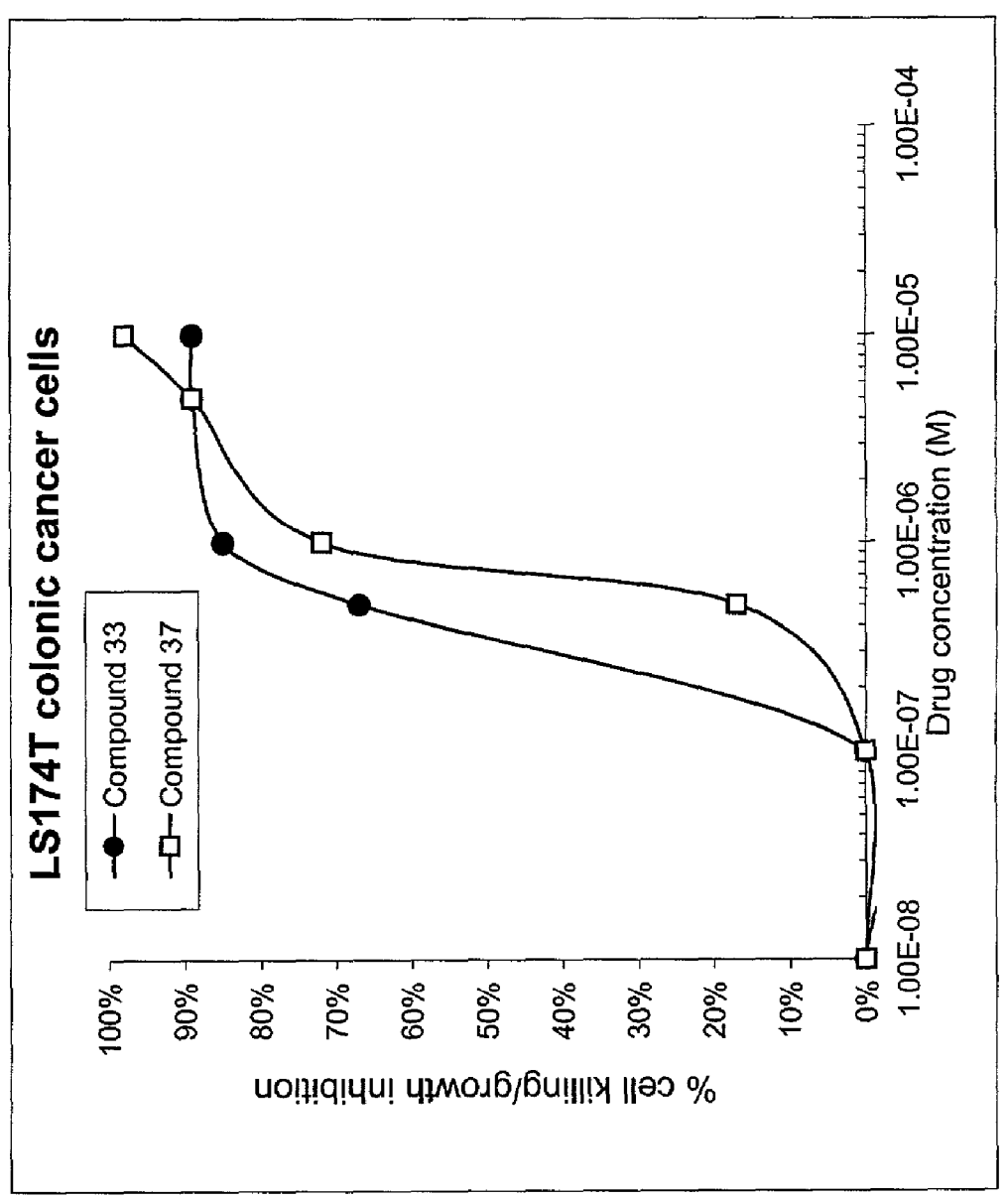
FIG. 17 shows the treatment of colonic cancer cells (LS174T) with compounds of the invention.

FIG. 12 discloses methods for preparing residues of the above formulas attached to precursors of the $Ar_3$ rings of the compounds of the invention.

Some other disclosed embodiments of the invention relate to compounds similar to the above-described compounds, wherein a bridging "A" group is inserted between the $Ar_3$ and $Ar_4$ groups, to give a compound of the Formula (II):

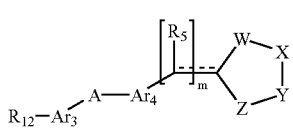

(II)

wherein:

(a) m is an integer 0 or 1;
(b) $R_{12}$ is an alkyl, a substituted alkyl, a cycloalkyl, a substituted cycloalkyl, a heterocyclic, a substituted heterocyclic, a heteroaryl, a substituted heteroaryl, an aryl or a substituted aryl residue;
(c) $Ar_3$ comprises an aryl, a substituted aryl, a heteroaryl or a substituted heteroaryl residue,
(d) A is an alkylene, a substituted an alkylene, O, S, NH, N-alkyl, N-substituted alkyl, —C(O)—, carboxamide or an alkylcarboxamide residue,
(e) $Ar_4$ is an aryl, a substituted aryl, a heteroaryl or a substituted heteroaryl residue;
(f) $R_5$ is hydrogen, alkyl or substituted alkyl;
(g) ----- represents a bond present or absent; and
(h) W, X, Y and Z are independently or together —C(O)—, C(S), S, O, or N—H residues;

with the proviso that when $R_{12}$ and $Ar_3$ together are a 3,5,5,8,8-pentamethyl-5,6,7,8-tetrahydro-2-naphthyl or 5,5,8,8-tetramethyl-5,6,7,8-tetrahydro-2-naphthyl residue, $Ar_4$ is an unsubstituted 1,4-benzene residue, and W, X, Y and Z together form a 2,4-thiazolidinedione residue, then A does not comprise a carboxamide residue, an alkylcarboxamide residue, an N-alkyl residue, or a >C═CH2 residue;

or a pharmaceutically acceptable salt thereof.

With the exception of the bridging "A" group, whose structure is described above, the structures of the other radicals and/or residues of the compounds of Formula (II) are generally similar and/or co-extensive to those of Formula (I), described hereinabove, and hence the description of the alternatives for those radicals and/or residues will not be repeated.

The compounds disclosed herein may also include salts of the compounds, such as salts with cations, in order to form a pharmaceutically acceptable salt. Cations with which the compounds of the invention may form pharmaceutically acceptable salts include alkali metals, such as sodium or potassium; alkaline earth metals, such as calcium; and trivalent metals, such as aluminum. The only constraint with respect to the selection of the cation is that it should not unacceptably increase the toxicity. Due to the tautomerism described above for the compounds, mono-, di- or tri-salts may be possible depending on the corresponding alkali metal. Also, one or more compounds disclosed herein may include salts formed by reaction of a nitrogen contained within the compound, such as an amine, aniline, substituted aniline, pyridyl and the like, with an acid, such as HCl, carboxylic acid and the like. Therefore, all possible salt forms in relationship to the tautomers and a salt formed from the reaction between a nitrogen and acid are within the scope of the invention.

The present invention provides, but is not limited to, the specific compounds set forth in the Examples as well as those set forth below, and a pharmaceutically acceptable salt thereof:

4-[3-(1-adamantyl)-4,5-methylenedioxyphenyl]-benzylidene-2,4-thiazolidinedione,
6-[3-(1-adamantyl)-4,5-methylenedioxyphenyl]-naphthalen-2-yl-methylene-2,4-thiazolidinedione,
4-[3-(2-methoxyphenyl)-4,5-methylenedioxyphenyl]-benzylidene-2,4-thiazolidinedione,
4-[3-(1-adamantyl)-4-methoxyphenyl]-benzylidene-2,4-thiazolidinedione,
4-[3-(1-adamantyl)-4-hydroxyphenyl]benzylidene-2,4-thiazolidinedione,
6-[3-(1-adamantyl)-4-methoxyphenyl]-naphthalen-2-yl-methylene-2,4-thiazolidinedione,
6-[3-(1-adamantyl)-4-methoxyphenyl]-naphthalen-2-yl-methyl-2,4-thiazolidinedione,
4-[3-(1-adamantyl)-4-methoxymethoxyphenyl]-benzylidene-2,4-thiazolidinedione,
6-[3-(1-adamantyl)-4-(t-butyldimethylsilyloxy)phenyl]-benzylidene-2,4-thiazolidinedione,
6-(3-phenyl-4-methoxyphenyl)-naphthalen-2-yl-methylene-2,4-thiazolidinedione,
6-[3-(t-butyl)-4-methoxyphenyl]-naphthalen-2-yl-methylene-2,4-thiazolidinedione,
6-[3-(1-adamantyl)-4-hydroxyphenyl]-naphthalen-2-yl-methyl-2,4-thiazolidinedione,
5-[3-(1-adamantyl)-4-methoxyphenyl]-naphthalen-1-yl-methylene-2,4-thiazolidinedione,
6-[5-(3,3-dimethyl-2,3-dihydrobenzofuryl)]-naphthalen-2-yl-methylene-2,4-thiazolidinedione,
6-[3-(1-methylcyclohexyl)-4-methoxyphenyl]-naphthalen-2-yl-methylene-2,4-thiazolidinedione,
5-[6-(3-[1-adamantyl]-4-methoxyphenyl)-naphthalen-2-yl]-2,4-thiazolidinedione,
5-[6-(3-[1-adamantyl]-4-hydroxyphenyl)-naphthalen-2-yl]-2,4-thiazolidinedione,
6-[3-(3-pyridyl)-4,5-methylenedioxyphenyl]-naphthalen-2-yl-methylene-2,4-thiazolidinedione,
6-[3-(4-pyridyl)-4,5-methylenedioxyphenyl]-naphthalen-2-yl-methylene-2,4-thiazolidinedione,
6-[3-(3-pyridyl)-4,5-methylenedioxyphenyl]-naphthalen-2-yl-methyl-2,4-thiazolidinedione,
6-[3-(4-pyridyl)-4,5-methylenedioxyphenyl]-naphthalen-2-yl-methyl-2,4-thiazolidinedione,
6-[3-(1-adamantyl)-4-hydroxyphenyl]-naphthalen-2-yl-methylene-2,4-thiazolidinedione,
6-[3-(t-butyl)-4-hydroxyphenyl]-naphthalen-2-yl-methylene-2,4-thiazolidinedione,
6-[3-(1-adamantyl)-4,5-methylenedioxyphenyl]-naphthalen-2-yl-methyl-2,4-thiazolidinedione,
4-[3-(1-adamantyl)-4,5-methylenedioxyphenyl]-benzylidene-2-thioxo-4-thiazolidinone,
4-[3-(1-adamantyl)-4-methoxyphenyl]-benzylidene-2-thioxo-4-thiazolidinedione,
6-(3-phenyl-4-methoxyphenyl)-naphthalen-2-yl-methylene-2-thioxo-4-thiazolidinone,
6-[3-(t-butyl)-4-methoxyphenyl]-naphthalen-2-yl-methylene-2-thioxo-4-thiazolidinone,
5-[3-(1-adamantyl)-4-methoxyphenyl]-naphthalen-1-yl-methylene-2-thioxo-4-thiazolidinone,
6-[5-(3,3-dimethyl-2,3-dihydrobenzofuryl)]-naphthalen-2-yl-methylene-2-thioxo-4-thiazolidinone,
6-[3-(1-methylcyclohexyl)-4-methoxyphenyl]-naphthalen-2-yl-methylene-2-thioxo-4-thiazolidinone,
6-[3-(1-adamantyl)-4,5-methylenedioxyphenyl]-naphthalen-2-yl-methyl-2-thioxo-4-thiazolidinone,
5-[6-(3-[1-adamantyl]-4-methoxyphenyl)-naphthalen-2-yl]-2,4-thiazolidinedione,
5-[6-(3-[1-adamantyl]-4-hydroxyphenyl)-naphthalen-2-yl]-2,4-thiazolidinedione, and
5-[6-(3-[1-adamantyl]-4-hydroxyphenyl)-naphthalen-2-yl]-2,4-thiazolidinedione.

The present invention does not include a compound of the formula:

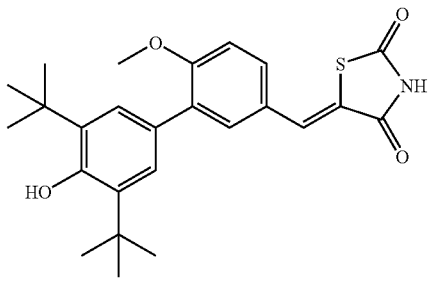

Figure 5:
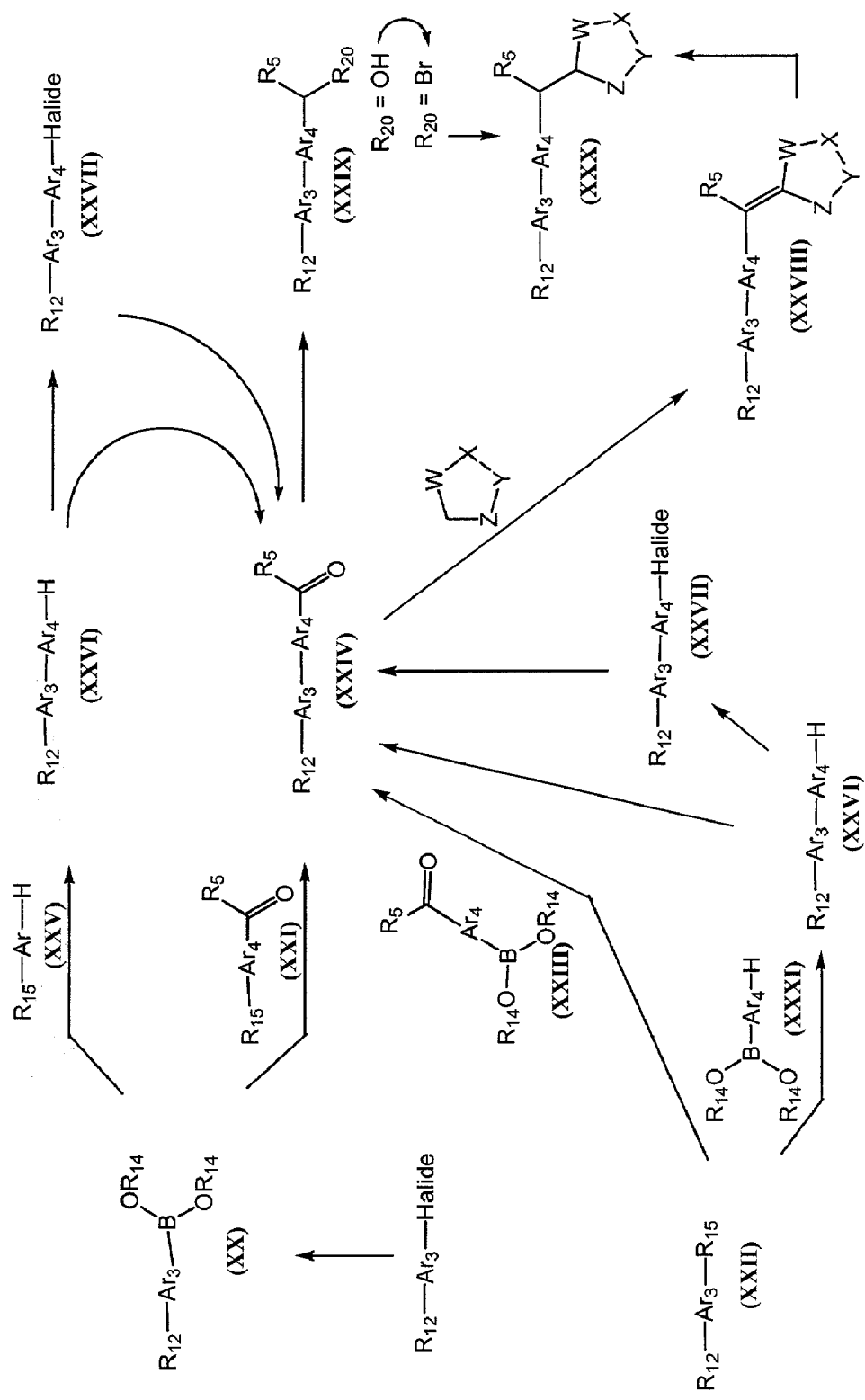
FIG. 5 shows examples of methods for the synthesis of certain coupled biaryl compounds disclosed herein.

3-(3,5, -Di-t-butyl-4-hydroxyphenyl)-4-methoxy-benzylidene-2,4-thiazolidinedione Making the Compounds of the Invention Various synthetic methods may be employed in the production of the compounds disclosed herein. A representative set of synthetic pathways is shown in FIG. 5. One method, for example, includes coupling a boronic acid of Formula (XX), $R_{14}$=H, with a carbonyl-containing aryl bromide of Formula (XXI), $R_{15}$=Br, to give biaryl (XXIV) that is substituted with a carbonyl group, such as a formyl group (i.e., $R_5$=H). Alternatively, boronic acid (XX) may be coupled with aryl bromide (XXV), $R_{15}$=Br, to give biaryl (XXVI) that is subsequently formylated using techniques known in the art, such as the Vilsmeier or the Vilsmeier-Haack reaction, the Gatterman reaction, the Duff reaction, the Reimer-Tiemann reaction or a like reaction. Coupling reactions such as that described for the formation of Biaryl (XXIV) and (XXVI) may also be conducted using boronic esters, such as where $R_{14}$ together with the boron from a pinacol borate ester (formation of pinacol esters: Ishiyama, T., et al., *J. Org. Chem.* 1995, 60, 7508–7510, Ishiyama, T., et al., *Tetrahedron Letters* 1997, 38, 3447–3450; coupling pinacol esters: Firooznia, F. et al., *Tetrahedron Letters* 1999, 40, 213–216, Manickam, G. et al., *Synthesis* 2000, 442–446; all four citations incorporated herein by reference). In addition, $R_{15}$ may also be I, Cl or triflate (derived from a phenol).

Biaryl (XXVI) may also be acylated, for example by the Friedel-Crafts Acylation reaction (using an acid chloride) or the like to give biaryl (XXIV) where $R_5$ is not hydrogen. Alternatively, in a two step manner, biaryl (XXVI) is formylated by first performing a halogenation step to give biaryl (XXVII), such as a bromination, followed by a halogen-metal exchange reaction using an alkyl lithium and reaction with DMF or equivalent known in the art to give biaryl (XXIV) where $R_5$ is H. The carbonyl group of biaryl (XXIV) may subsequently be condensed with a heterocycle possessing an active methylene moiety, such as 2,4-thiazolidinedione, 2-thioxo-4-thiazolidinedione, isoxazolidinedione, 2,4-imidazolidinedione or 2-thioxo-4-imidazolidinedione to give benzylidene (XXVIII). The carbonyl group of biaryl (XXIV) may also be reduced, such as with sodium borohydride, diisobutyl aluminum hydride, or the like, to give benzyl alcohol (XXIX, $R_{20}$=OH) and converted to benzyl bromide (XXIX, $R_{20}$=Br) with HBr or some other method known in the art, such as PPh₃/CBr₄ or converted to another leaving group, such as, for example, mesylate or iodide. Benzyl bromide (XXIX, $R_{20}$=Br) or like compound is allowed to react with the anion(s) of 2,4-thiazolidinedione to give biaryl [(XXX), where: W=—C(O)—, X=—NH—, Y=—C(O)— and Z=—S—]. Similarly, anions of other heterocycles disclosed herein may be used. Alternative, biaryl [(XXX), where: W=—C(O)—, X=—NH—, Y=—C (O)— and Z=—S—] may be prepared by a reduction of benzylidene [(XXVIII), where: W=—C(O)—, X=—NH—, Y=—C(O)— and Z=—S—] using methods known in the art, such as hydrogenation in the presence of Pd/C, Mg/MeOH, LiBH₄ in THF/pyridine and the like.

In an alternative manner, the coupling may take place between aryl (XXII), such as where $R_{15}$=Br, and boronic acid (XXIII, $R_{14}$=H or alkyl) to give the above mention biaryl (XXIV). Also aryl (XXII) may be coupled with boronic acid (XXXI) to give biaryl (XXVI). Employing the same strategy as described above biaryl (XXVI) may be converted to biaryl (XXIV).

In some embodiments of the invention provide a process for the preparation of a compound of the Formula (XV):

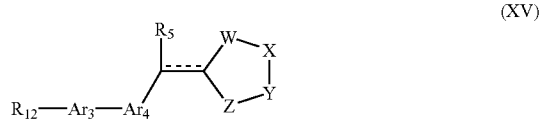

(XV)

wherein:

(a) Ar₃ is an aromatic ring residue having the formula:

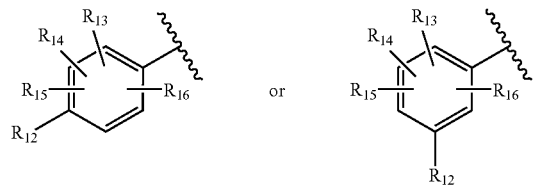

wherein (i) $R_{12}$ is an alkyl or substituted alkyl residue comprising 6 to 18 carbon atoms; or a cycloalkyl, a substituted cycloalkyl, a heterocyclic, a substituted heterocyclic, a heteroaryl, a substituted heteroaryl, an aryl or a substituted aryl residue comprising 5 to 18 carbon atoms, and (ii) $R_{13}$, $R_{14}$, $R_{15}$ and $R_{16}$ are independently or together hydrogen, a hydroxyl, or an amino residue, or an alkyl or substituted alkyl comprising 6 to 18 carbon atoms; or an alkenyl, a substituted alkenyl, an alkynyl, a substituted alkynyl, a cycloalkyl, a substituted a cycloalkyl, a heterocyclic, a substituted heterocyclic, an alkoxy, a substituted alkoxy, an acyl, a mono-substituted amino, a di-substituted amino, a carboxy, a carboalkoxy, a nitrile an alkylcarboxamide, a substituted an alkylcarboxamide, a dialkylcarboxamide, a substituted dialkylcarboxamide, a haloalkoxy, a triorganosilyloxy, a heteroaryl, a substituted heteroaryl, an aryl, or a substituted aryl residue comprising 5 to 18 carbon atoms; and (iii) Ar₃ and $R_{12}$ do not together form a substituted or unsubstituted 5,6,7,8-tetrahydro-2-napthyl residue, a substituted or unsubstituted 1,2,3,4-tetrahydro-6-quinolinyl residue, or a substituted or unsubstituted 1,2,3,4-tetrahydro-7-quinoxalinyl residue;

(b) Ar$_4$ is an unsubstituted aryl, a substituted aryl, a heteroaryl or a substituted heteroaryl residue comprising 5 to 18 carbon atoms;
(c) R$_5$ is hydrogen, hydroxy, alkyl or substituted alkyl;
(f) ----- represents a bond present or absent;
(g) m is the integers 0 or 1; and
(f) W, X, Y and Z form a residue of formula:

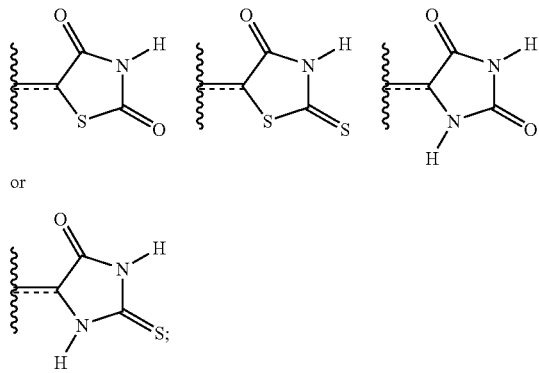

or

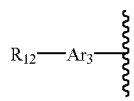

the method comprising the steps of:
1) coupling a first aryl residue with a second aryl residue to give a biaryl carbonyl containing compound; wherein the first aryl residue comprises a substituted or unsubstituted residue having the structure:

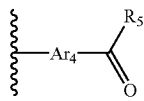

and wherein the second aryl residue has a carbonyl group and comprises a substituted or unsubstituted residue having the structure:

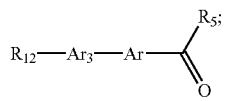

and wherein the biaryl carbonyl containing compound comprises a substituted or unsubstituted residue having the structure:

R$_{12}$—Ar$_3$—Ar—C(R$_5$)=O;

and
2) condensing the biaryl carbonyl containing compound with an active methylene compound of the structure:

In another embodiment the invention provides a process further comprising the step of reducing the benzylidene of Formula (XV) (wherein the double bond is present) to form the benzyl compound of Formula (XVI) wherein the double bond has been reduced to form a single bond:

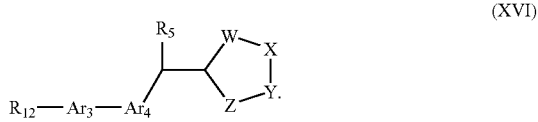

(XVI)

A number of methods suitable for reducing benzylidene compounds to benzyl compounds (including hydrogenation, reaction with metal hydride reagents, or dissolving metal reductions) are known to those of skill in the art, and those methods may be applied in the methods of the instant invention.

The various organic group transformations utilized herein may be performed by a number of procedures other than those described above. References for other synthetic procedures that may be utilized for the synthetic steps leading to the compounds disclosed herein may be found in, for example, March, J., *Advanced Organic Chemistry*, 4$^{th}$ Edition, Weiley-Interscience (1992); or Larock, R. C., *Comprehensive Organic Transformations, A Guide to Functional Group Preparations*, VCH Publishers, Inc. (1989), both incorporated herein by reference.

One embodiment of the invention relates to the processes for making compounds of Formula I which comprises coupling two aromatic rings to give a biaryl wherein one of the aryl rings contains a carbonyl moiety, preferably an aldehyde. The resulting biaryl product may be subsequently condensed with an active methylene compound, such as 2,4-thiazolidinedione, 2-thioxo-4-thiazolidinedione, 2,4-imidazolidinedione or 2-thioxo4-imidazolidinedione to give a benzylidene compound of Formula (I) where ----- is a bond. In an optional step, the benzylidene compound may be reduced to give a benzyl compound of Formula (I) where ----- is absent.

Coupling of two aryl rings may be conducted using an aryl boronic acid or esters with an aryl halide (such as, iodo, bromo, or chloro), triflate or diazonium tetrafluoroborate; as described respectively in Suzuki, *Pure & Applied Chem.*, 66:213–222 (1994), Miyaura and Suzuki, *Chem. Rev.* 95:2457–2483 (1995), Watanabe, Miyaura and Suzuki, *Synlett.* 207–210 (1992), Littke and Fu, *Angew. Chem. Int. Ed.*, 37:3387–3388 (1998), Indolese, *Tetrahedron Letters*, 38:3513–3516 (1997), Firooznia, et. al., *Tetrahedron Letters* 40:213–216 (1999), and Darses, et. al., *Bull. Soc. Chim. Fr.* 133:1095–1102 (1996); all incorporated herein by reference for their disclosures of methods for coupling aryl rings. According to this coupling reaction, precursors such as (XX) and (XXI) may be employed:

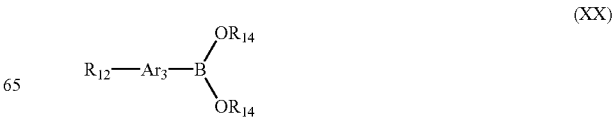

(XX)

(XXI)

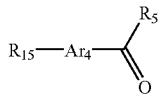

where $R_{14}$ is either alkyl or hydrogen and $R_{15}$ is a halide (such as, iodo, bromo, or chloro), triflate or diazonium tetrafluoroborate. Alternately, it is understood that the coupling groups may be reversed, such as the use of (XXII) and (XXIII), to achieve the same coupling product:

(XXII)

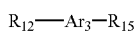

(XXIII)

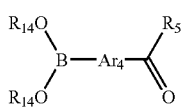

where $R_{14}$ and $R_{15}$ have the same meaning as described above. The preparation of the above mentioned precursors may be prepared by methods readily available to those skilled in the art. For example, the boronic ester may be prepared from an aryl halide by conversion of the corresponding aryl lithium, followed by treatment with a trialkyl borate. Preferably, the boronic ester is hydrolyzed to the boronic acid for coupling.

The coupling reaction may also be conducted between an aryl zinc halide and an aryl halide or triflate. Alternately, the coupling reaction may also be executed using an aryl trialkyltin derivative and an aryl halide or triflate. These coupling methods are reviewed by Stanforth, *Tetrahedron* 54:263–303 (1998) and incorporated herein by reference. In general, the utilization of a specific coupling procedure is selected with respect to available precursors, chemoselectivity, regioselectivity and steric considerations.

Condensation of the biaryl carbonyl containing derivatives (e.g., FIG. 5, compound (XXIV)) with a suitable active methylene compound, such as, 2,4-thiazolidinedione, may be accomplished by the use of methods known in the art. For example, the biaryl carbonyl product from the coupling reaction may be condensed with an active methylene compound to give a benzylidene compound of Formula (I) (i.e., ----- is a bond) as described by Tietze and Beifuss, *Comprehensive Organic Synthesis* (Pergamon Press), 2:341–394, (1991), incorporated herein by reference. It is understood by those of skill in the art that intermediates having hydroxyl groups bound thereto may be formed during condensation of a biaryl carbonyl containing derivative and an active methylene compound, as shown below.

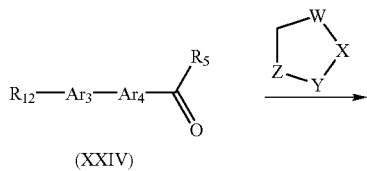

(XXIV)

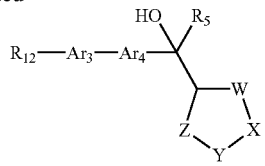

Figure 6:
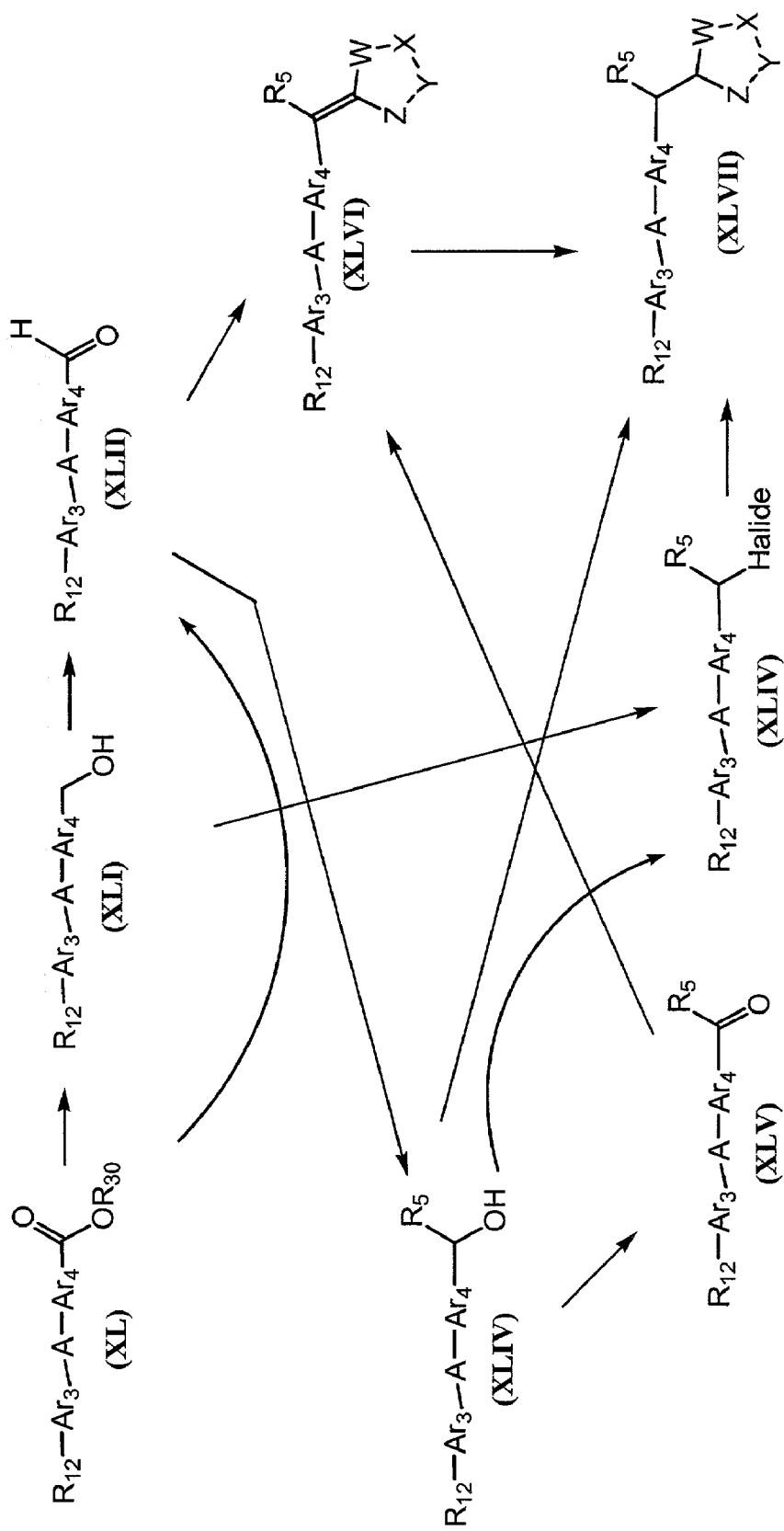
FIG. 6 shows examples of methods for the synthesis of certain heterocyclic compounds disclosed herein.

The hydroxyl groups of such intermediates are often eliminated (as water) during the condensation reaction, to form the desired benzylidene compound. Nevertheless, the conditions of the reaction may be modified for the isolation or further use of hydroxyl containing intermediates, and such embodiments are within the scope of the invention. Although the reaction shown above depicts the formation of the condensation intermediate for the reaction between compound (XXIV) and an active methylene compound, it is understood that a similar intermediate is within the scope of the methods for condensing compounds (XLV) and (XLII) as shown in FIG. 6. Effective catalysts for the condensation may be selected from ammonia, primary, secondary and tertiary amines, either as the free base or the amine salt with an organic acid, such as acetic acid. Examples of catalysts include pyrrolidine, piperidine, pyridine, diethylamine and the acetate salts thereof. Inorganic catalysts may also be used for the condensation. Inorganic catalysts include, but are not limited to, titanium tetrachloride and a tertiary base, such as pyridine; and magnesium oxide or zinc oxide in an inert solvent system. This type of condensation can be strongly solvent-dependent and it is understood that routine experimentation may be necessary to identify the optimal solvent with a particular catalyst, preferable solvents include ethanol, tetrahydrofuran, dioxane or toluene; or mixtures thereof.

The active methylene compound of the present invention may be 2,4-thiazolidinedione, 2-thioxo-4-thiazolidinone, 2,4-imidazolidinedione or 2-thioxo-4-imidazolidinedione. The resulting benzylidene (e.g., FIG. 5, compound (XXVIII)) may be reduced, if desired, to a compound of Formula (I) wherein ----- is absent (e.g., FIG. 5, compound (XXX)).

In addition, various methods may be employed in the production of the compounds disclosed herein wherein n=1, representative examples are shown in FIG. 6. Structures of compound (XL) may be prepared by methods known in the art. The acid, $R_{30}$=H or the ester, $R_{30}$=aryl, alkyl or substituted alkyl, may be reduced to the corresponding benzyl alcohol (XLI) followed by oxidation to an aldehyde (XLII). Alternatively, ester (XL), $R_{30}$=alkyl or substituted alkyl, may be reduced directly to the aldehyde via selective reductions, for example, DIBAL. Aldehyde (XLII) may be reacted with a metal reagent, such as a Grignard reagent, to give benzyl alcohol (XLIV) that can subsequently be converted to ketone (XLV) via an oxidation, such as a Swern oxidation, Corey oxidation with NCS or another suitable procedure described by Hudlicky, M, *Oxidations in Organic Chemistry*, ACS Monograph 186 (1990), incorporated herein by reference. In a similar manner as described above, compound (XLII) or compound (XLV) may be condensed with an active methylene of a heterocycle to give compound (XLVI). The reduced analogue (XLVII) may be prepared in a manner similar to the process described above using a benzyl halide derived from either benzyl alcohol (XLI) or reduction from compound (XLVI).

Figure 10:
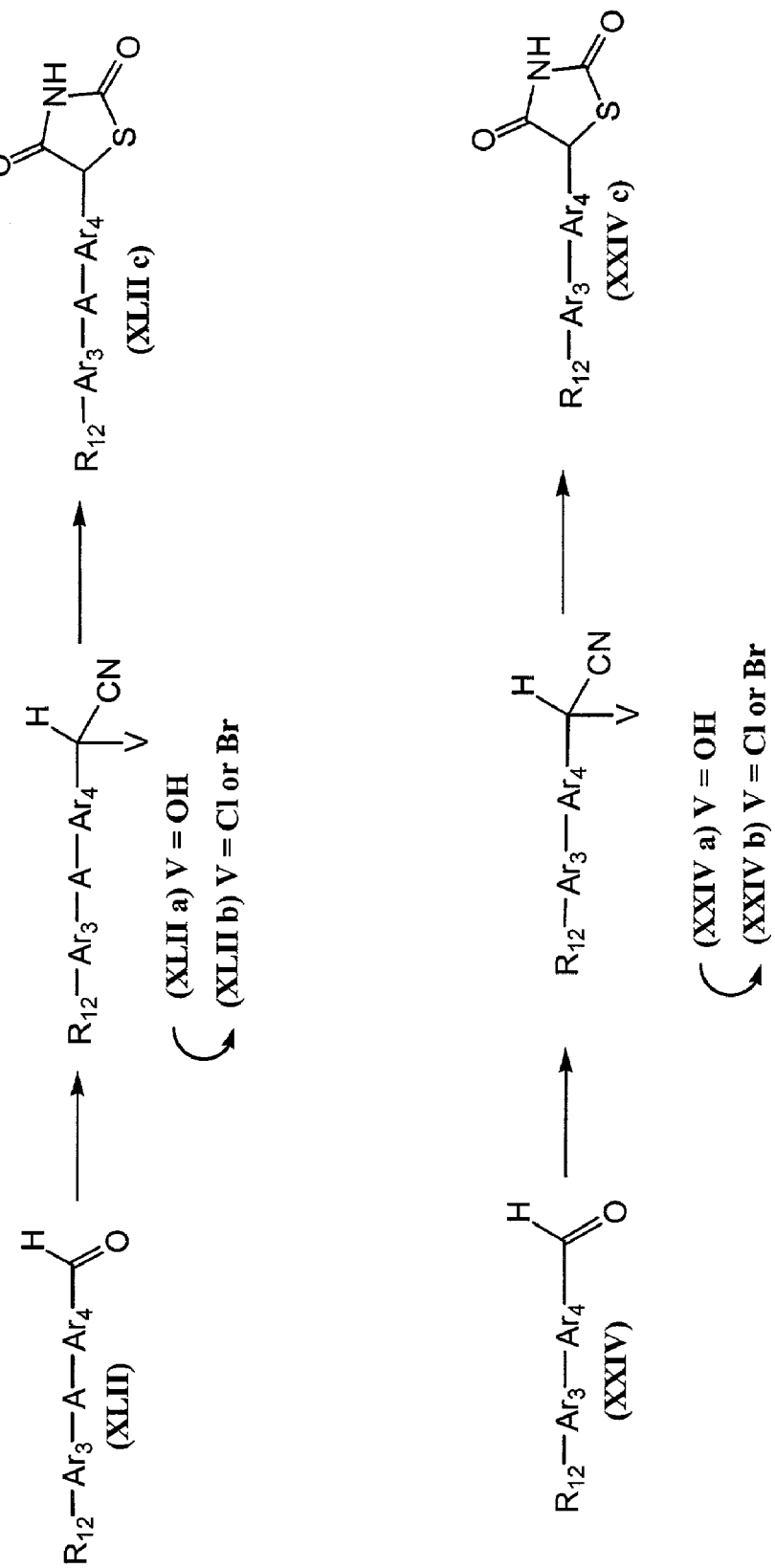
FIG. 10 shows examples of methods of synthesis of certain heterocyclic compounds of the invention.

In addition, various methods may be employed in the production of the compounds disclosed herein, such as compounds of Formula (I) and compounds of Formula (II), representative examples are shown in FIG. 10. Utilizing, for example, compound (XLII) or (XXIV) the carbonyl may be converted to a cyanohydrin using methods known in the art. Such methods include, the use of acetone cyanohydrin, TMS-CN/ZnI$_2$ (followed by hydrolysis of the TMS ether) and the like. The resulting alcohol of the cyanohydrin may be converted to a halide (where V=Cl or Br) with the use of thionyl chloride, thionyl bromide or the like, in the presence or absence of solvent. Conversion to compounds of Formula (XXIV(c)) may be prepared by the reaction of the (XLII a) or (XXIV b) with thiourea followed by hydrolysis.

Figure 7:
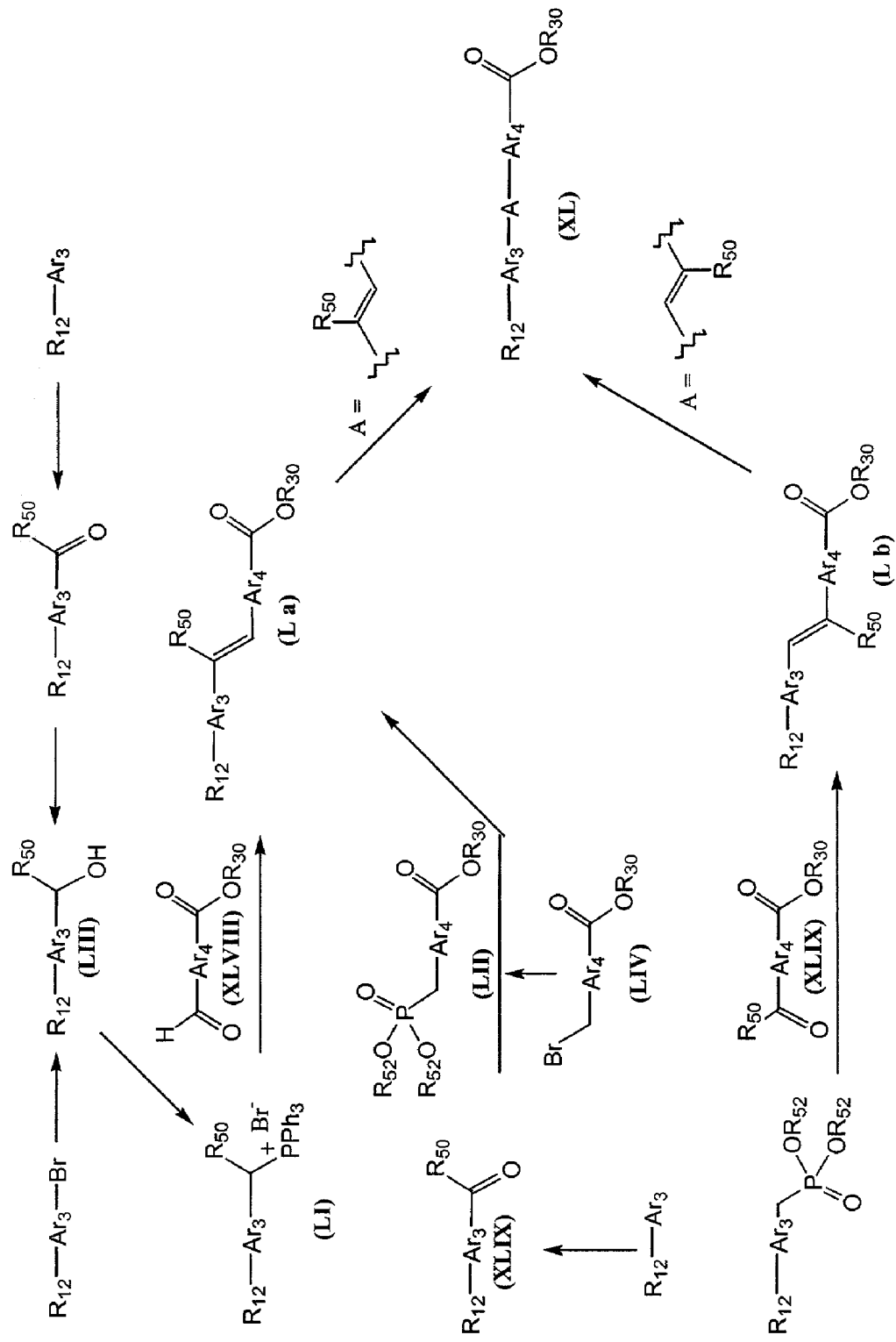
FIG. 7 shows examples of methods for the synthesis of certain bridged biaryl compounds disclosed herein.

Another aspect of the invention is a set of synthetic pathways for compounds of Formula (II) as shown in FIG. 7. One method, for example, for when A=alkylene, includes the use of the Wittig reaction (Maercker, Org. Reactions 1965, 14, 270–490), Horner-Emmons (Wadsworth, Org. Reactions 1977, 25, 73–253) and the like, references incorporated herein by reference. The phosphorus ylide as found in either the Wittig or Horner-Emmons reactions, generated from a phosphonium salt, phosphonate or the like, can react with aldehyde or ketone, such as, aryl (XLVIII) or aryl (XLIX, where $R_{50}$ is H or alkyl) to give diaryl alkylene (L a) or (L b). The formation of the ylide can be generated by treatment of a phosphonium salt, such as phosphonium salt (LI), a phosphonate, such as phosphonate (LII), or the like, with a base such as an alkyl lithium (for example, n-butyl lithium, t-butyl lithium and the like), metal hydride (for example, potassium hydride, sodium hydride and the like) or a base known in the art of appropriate strength. Phosphonium salt (LI) can be prepared from benzyl halide (such as a bromide, and a tri-substituted phosphine, such as triphenylphosphine. Alternatively, phosphonium salt (LI) can be prepared from benzyl alcohol (LIII) and a tri-substituted phosphine-hydrohalide, such as triphenylphosphine-hydrochloride or -hydrobromide. Phosphonate (LII) can be prepared from benzyl halide (LIV), such as a bromide, via the Arbuzov reaction (also known as the Michaelis-Arbuzov rearrangement, Petrov, et. al., Russ. Chem. Rev. 1983, 52, 1030–1035, incorporated herein by reference). Diaryl alkylene (L a or L b) can subsequently be converted into compounds of Formula (II) utilizing methods described herein.

Figure 8:
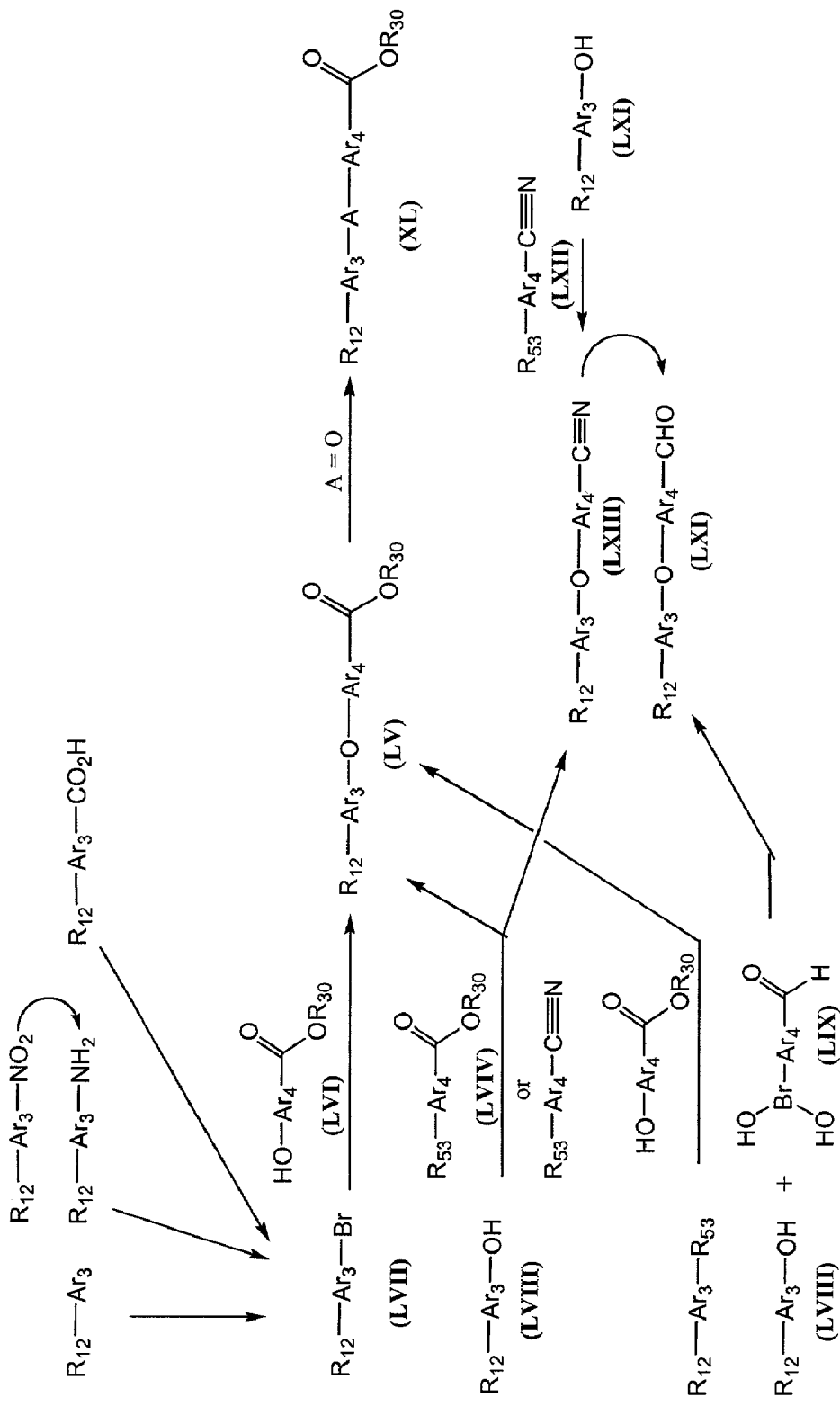
FIG. 8 shows examples of methods for the synthesis of certain bridged biaryl compounds disclosed herein.

Another set of synthetic pathways for compounds of Formula (II), for example when A=oxygen, are included in this invention. For example, as shown in FIG. 8, compounds of Formula (II) when A=oxygen, can be prepared through the use of the Ullmann ether synthesis (Moroz, et al. Russ. Chem. Reviews 1974, 43, 679–689), ether synthesis via metal-promoted arylation of phenol with either an aryl halide (Aranyos, et. al., J. Am. Chem. Soc. 1999, 121, 4369–4378) or boronic acid (Evans, et. al., Tetrahedron Letters, 1998, 39, 2937–2940, Chan, et al., Tetrahedron Letters, 1998, 39, 2933–2936, Jung, J. Org. Chem. 1999, 64, 2976–2977), phenoxide addition to electron deficient aryl rings (Paradisi, Comprehensive Organic Synthesis, Vol 4, 423–450, Trost, Editor-In-Chief, Pergamon Press 1991), and like reactions, references incorporated herein by reference. These methods represent examples for the synthesis of diaryl ether (LV). In the case of the Ullmann ether synthesis, phenol (LVI) can be coupled with aryl-halide (LVII), halide=iodide, bromide or chloride, in the presence of metallic copper or a copper salt, such as CuCl2, CuI, CuBr, CuCl, CuCO3, and the like to give diaryl ether (LV). Similarly, palladium can be used to catalyze the coupling between phenol (LVIII a) and aryl-$R_{53}$ (LVIV a) where $R_{53}$=I, Br, Cl or OTf). The ligands that comprise the palladium catalysis may be electron-rich, bulky aryldialkylphosphines, such as those described by Aranyos et. al. in J. Am. Chem. Soc. 1999, 121, 4369–4378. A coupling of this type can accommodate most groups including a carbonyl functionality or one that can be converted into one. For example, using these coupling conditions, 4-chlorobenzonitrile can be coupled with 3-isopropyl-phenol in the presence of Pd(OAc)$_2$, 2-(di-tert-butylphophino)biphenyl (the active catalysis is generated in situ) and K$_3$PO$_4$ gave 4-(3'-isopropylphenoxy)benzonitrile in 91% yield. Subsequently, the nitrile can be converted to an aldehyde using reducing agents known in the art, such as, DIBAL; or the nitrile can be converted to a ketone using methods known in the art, such as treatment with a Grignard reagent and subsequent hydrolysis. In this conversion, certain salts, such as Cu(I) salts, can also be used to facilitate the conversion of a nitrile to ketone (Weiberth, J. Org. Chem. 1987, 52, 3901). It should be noted that phenol (LVIII b) can be coupled with aryl-$R_{53}$ (LVIV b), where $R_{53}$=I, Br, Cl or OTf, to achieve diaryl ether (LV). In still another method for the preparation of diaryl ether (VL), Cu(OAc)$_2$ can be used to couple phenol (LVIII) and an aryl boronic acid (LX) to give diaryl ether (LV). This method can also accommodate many different groups, including a carbonyl functionality or groups that can be converted into a carbonyl group, as an example, those described herein. In yet another method diaryl ether (LV) can be prepared by the addition of a phenoxide ion to an election deficient aryl ring. For example, 4-isopropyl phenol and 4-fluoro-benzonitrile in the presence of K$_2$CO$_3$ in dimethylformamide at 110° C. gave 4-(4-isopropyl-phenoxy)-benzonitrile in 95% yield. As described above, the nitrile can be converted to an aldehyde or some other carbonyl group. Therefore, the anion of phenol (LXI) and aryl-halide (LXII) can be coupled to give diaryl ether (LXIII).

By selecting the appropriate phenol (LVI or LVIII) and the corresponding substituted aryl [i.e., aryl-halide (LVII or LVIV) or aryl boronic acid (LX)] the desired diaryl ether (LV) can be obtained. Diaryl ether (LV) can subsequently be converted into compounds of Formula (II) utilizing methods described herein for when A is oxygen.

Figure 9:
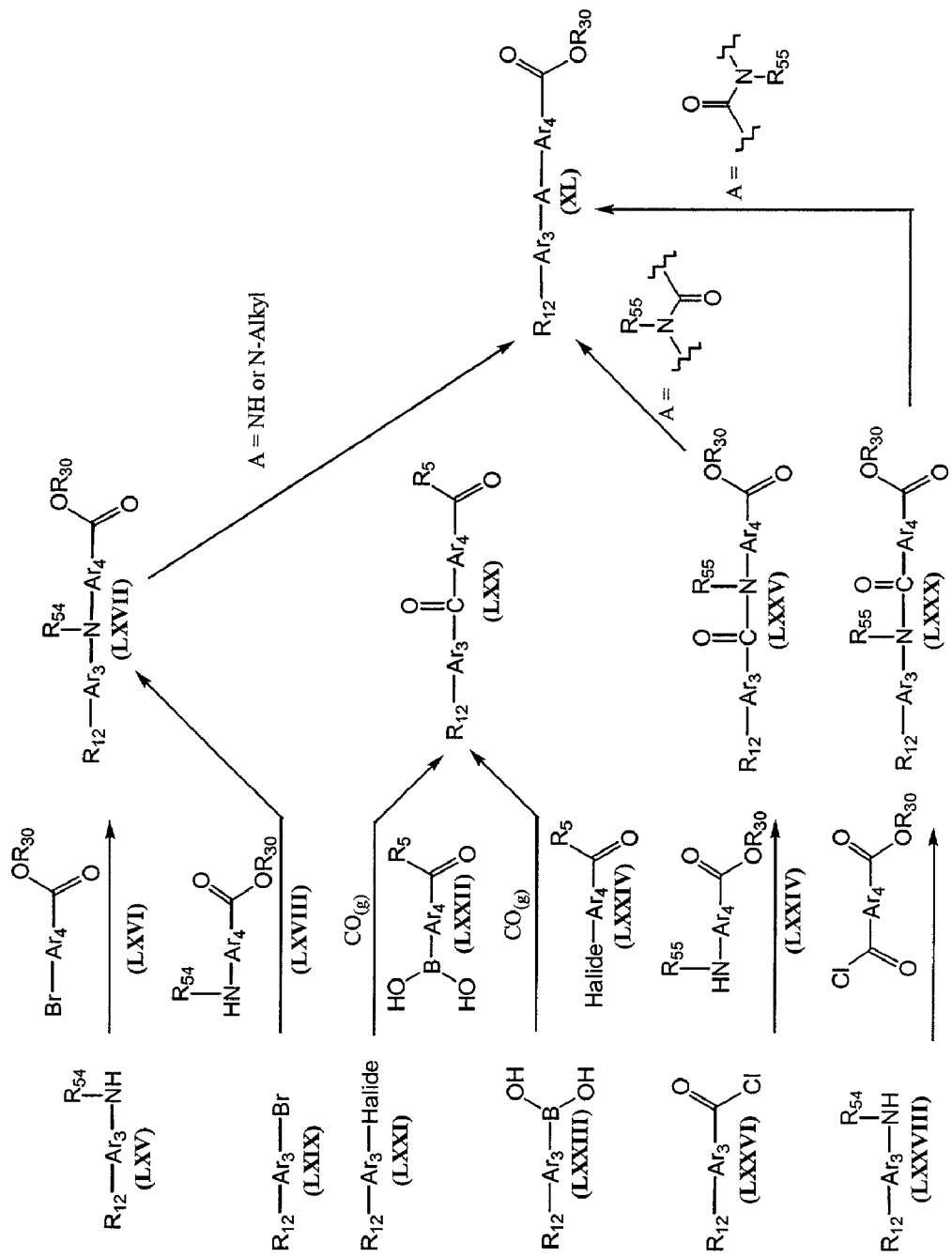
FIG. 9 shows examples of methods for the synthesis of certain bridged biaryl compounds of the invention.

Another aspect of the invention is a synthetic pathway for compounds of Formula (II) when A=NH or N-alkyl as shown in FIG. 9. By way of example, methods include palladium catalyzed amination of aryl bromide, chloride or triflate (Wolfe and Buchwald, J. Org. Chem. 2000, 65, 1144–1157, Wolfe, et. al., J. Org. Chem. 2000, 65, 1158–1174), arene-chromium palladium complexes for amination of aryl bromides (Kamidawa, et. al., J. Org. Chem. 1998, 63, 8407–8410), addition of an aniline to electron deficient aryl rings (Paradisi, Comprehensive Organic Synthesis, Vol 4, 423–450, Trost, Editor-In-Chief, Pergamon Press 1991), and like reactions, references incorporated herein by reference. Aniline (LXV, $R_{54}$=H or alkyl) and aryl (LXVI) can be coupled with a palladium catalysis to give diarylamine (LXVII). Aniline (LXV) can be prepared from methods known in the art. For example, an aryl-nitro compound can be reduced using hydrogenation conditions, Curtius rearrangement of a benzoic acid or direct amination using (CH3)$_3$SiN$_3$ and triflic acid. Mono-substituted anilines ($R_{54}$=alkyl) can be prepared by methods known in the art, such as, reductive alkylation. It is understood that aniline (LXVIII) and aryl (LXIX) can be coupled to achieve the same diarylamine (LXVII).

Another aspect of the invention is a synthetic pathway for Formula (II) when A is (C=O) as shown in FIG. 9. By way of example, methods include carbonylative cross-coupling of an aryl boronic acid and aryl-halide, such as iodo or bromo (Ishiyama, et. al., Tetrahedron Letters 1993, 34, 7595–7598, Ishiyama, et. al., J. Org. Chem. 1998, 63, 4726–4731, Cobb et. al., J. Med. Chem. 1998, 41, 5055–5069), palladium catalyzed cross-coupling of an acid chloride and an aryl boronic acid (Haddach and McCarthy, Tetrahedron Letters 1999, 40, 3109–3112), Friedel-Crafts acylation reaction and the like, references incorporated herein by reference. Diaryl ketone (LXX) can be prepared using Aryl-halide (LXXI, where halide=I, Br or OTf) and aryl boronic acid (LXXII) in the presence of a palladium catalysis in an atmosphere of carbon monoxide. Alternatively, Aryl-halide (LXXIV, where halide=I, Br or OTf) and aryl boronic acid (LXXIII) can be used to prepare diaryl ketone (LXX).

Another aspect of the invention is a synthetic pathway for Formula (II) when A=carboxamide or alkylcarboxamide as shown in FIG. (9). Amide (LXXV, where $R_{55}$ is H or alkyl) can be prepared using acid chloride (LXXVI) and aniline (LXXVII) in the presence of an appropriate base, such as pyridine, TEA, methyl morpholine, DIPEA. Alternatively, Amide (LXXX, where $R_{55}$ is H or alkyl) can be prepared using acid chloride (LXXIX) and aniline (LXXVIII) in the presence of an appropriate base.

A set of methods for preparing intermediates suitable for preparation of compounds containing heterocylic adamantyl derivatives are shown in FIG. 12. Phenyl acetonitrile can be used with acrylonitrile in the presence of a base, such as, triton B, in an alcoholic solvent to give diester (XXXXIV). Cyclization can be executive through the use of a base, one particularly good base was NaH, in xylene to give cyclohexanone (XXXXV) followed by acid promoted decarboxylation to give a new cyclohexanone (XXXXVI). The cyclohexanone is protected, for example, as a 1,3-dioxolane, and the nitrile is reduced to amine (XXXXVII) with lithium aluminum hydride in THF. Azaadamantanone (XXXXVIII) can be prepared from amine (XXXXVII) via a double Mannich reaction in a similar manner as described by Black in *Synthesis,* 1981, 829–830. The carbonyl of azaadamantanone (XXXXVIII) may subsequently be reduced via methods known in the art, such as, for example, hydrazine/KOH/triglyme, and the like, to give azaadamantane (XXXXIX).

Using the Compositions

The compounds disclosed herein are characterized by relatively low molecular weight and may be used to treat diseases in representative animal models, such as, athymic nude mice inoculated with human tumor cell lines. In addition, compounds of the invention have demonstrated oral bioavailability as exhibited by blood levels after oral dosing, either alone or in the presence of an excipient. Oral bioavailability allows oral dosing for use in chronic diseases, with the advantage of self-administration and decreased cost over other means of administration. The compounds described herein may be used effectively to prevent, alleviate or otherwise treat cancer or precancerous diseases and/or other disease states of uncontrolled proliferation in mammals, including humans.

The biological activity of the compounds of the invention may also be measured utilizing a panel of different human tumor cell lines. It is well known in the art that one or more of the known tumor cell lines used to test the antitumor activity of the above-listed polyaryl compounds can be utilized, such as:

For Leukemia: CCRF-CEM, HL-60 (TB), K-562, MOLT-4, RPMI-8226, and SR.

Lung Cancer: A549/ATCC, EKVX, HOP-62, HOP-92, NCI-H226, NCI-H23, NCI-H322M, NCI-H460, NCI-H292 and NCI-H522.

Colon Cancer: COLO 205, HCC-2998, HCT-116, HCT-15, HT-29, KM-12, LS174T and SW-620.

CNS Cancer: SF-268, SF-295, SF-539, SNB-19, SNB-75, and U-251.

Melanoma: LOX-IMVI, MALME-3M, M-14, SK-MEL-2, SK-MEL-28, SK-MEL-5, UACC-257, and UACC-62.

Ovarian Cancer: IGR-OVI, OVCAR-3, OVCAR-4, OVCAR-5, OVCAR-8, and SK-OV-3.

Renal Cancer: 786-0, A-498, ACHN, CAKI-1, RXF-393, RXF-631, SN12C, TK-10, and UO-31.

Prostate Cancer: PC-3, LNCaP and DU-145.

Pancreatic Cancer: BxPC-3, CCD-13Lu, LS 180, MIA PACA2, PANC-1, AsPC-1, SU.86.86, CFPAC-1, HPAF-II, HPAC, SW 1990, MPanc-96, Panc 10.05, Panc 03.27, Panc 06.03, Panc 08.13, Panc 02.03, Panc 02.13, Breast Cancer: MCF 7, MCF7/ADR-RES, MDA-MB-231/ATCC, HS578T, MDA-MB-435, MDA-N, BT-549, MDA-MB-468, MDA-MB-231 and T-47D.

This anti-cancer activity screening assay provides data regarding the general cytotoxicity of an individual compound. In particular, this type of assay is useful in identifying compounds which have enhanced cytotoxic activity against slow growing tumors as compared to faster growing tumor cells such as leukemia tumor cell lines. The identification of such compounds is critical since previously identified antitumor agents have low cytotoxic activity against slower growing tumors.

The anti-cancer activity of the compounds of the invention herein have been tested in in vitro assays using a microculture assay with 3-(4,5-dimethylthiazol-2-yl)-2,5-diphenyltetrazolium bromide ("MTT"). This assay has an advantage over in vivo assay in that results are obtained within a week as opposed to several months. The assay can be carried out in 96-well microtiter plates. The MTT assay is based on the production of a dark blue formazan product by dehydrogenase in the mitochondria of live tumor cells after exposure to drug for 6 days [M. C. Alley, D. A. Scudiero, A. Monks, M. L. Hursey, M. J. Czerwinski, D. L. Fine, B. J. Abbout, J. G. Mayo, R. H. Shoemaker and M. R. Boyd, *Cancer* Res., 48, 589, 1988]. Thus, only live cells are stained and can be measured at 595 nm. Anti-cancer activity can be reported as percent of the tumor cell growth in the presence of compound at a defined dose compared to control/untreated tumor cells.

The compounds of the present invention have been found to be potent compounds in a number of biological assays, both in vitro and in vivo, that correlate to, or are representative of, human diseases.

The compounds disclosed herein may be either used singularly or plurally, and with pharmaceutical compositions thereof for the treatment of mammalian diseases, particularly those diseases related to humans. Compounds disclosed herein and compositions thereof may be administered by various methods including, for example, orally, enterally, parenterally, topically, nasally, vaginally, opthalinically, sublingually or by inhalation for the treatment of diseases related to uncontrolled proliferative diseases such as, Routes of administration and dosages known in the art may be found in *Comprehensive Medicinal Chemistry, Volume* 5, Hansch, C. Pergamon Press, 1990; incorporated herein by reference. The compositions may also be used as regulators in diseases of uncontrolled proliferation. The composition may be useful in the treatment of polycystic kidney disease and cancers such as, carcinomas, lymphomas, leukemias, and sarcomas. A representative but non-limiting list of cancers is lymphoma, Hodgkin's Disease, myeloid leukemia, bladder cancer, brain cancer, head and neck cancer, kidney cancer, lung cancers such as small cell lung cancer and non-small cell lung cancer, myeloma, neuroblastoma/glioblastoma, ovarian cancer, pancreatic cancer, prostate cancer, skin cancer, liver cancer, melanoma, colon cancer, cervical carcinoma, breast cancer, and epithelial cancer. Compounds disclosed herein may be used for the treatment of inflammatory diseases such as osteoarthritis, rheumatoid arthritis, Crohn's Disease, pulmonary fibrosis, and Inflammatory Bowel Disease. Compounds disclosed herein may also be used for the treatment of precancer conditions such as cervical and anal dysplasias, other dysplasias, severe dysplasias, hyperplasias, atypical hyperplasias, and neoplasias.

Although the compounds described herein may be administered as pure chemicals either singularly or plurally, it is preferable to present the active ingredient as a pharmaceutical composition. Thus another embodiment of the invention is the use of a pharmaceutical composition comprising one or more compounds and/or a pharmaceutically acceptable salt thereof, together with one or more pharmaceutically acceptable carriers thereof and, optionally, other therapeutic and/or prophylactic ingredients. The carrier(s) must be "acceptable" in the sense of being compatible with the other ingredients of the composition and not overly deleterious to the recipient thereof.

Pharmaceutical compositions include those suitable for oral, enteral, parental (including intramuscular, subcutaneous and intravenous), topical, nasal, vaginal, ophthalinical, sublingually or by inhalation administration. The compositions may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combination thereof, and then, if necessary, shaping the product into the desired delivery system.

Pharmaceutical compositions suitable for oral administration may be presented as discrete unit dosage forms such as hard or soft gelatin capsules, cachets or tablets each containing a predetermined amount of the active ingredient; as a powder or as granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art., e.g., with enteric coatings.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or one or more preservative.

The compounds may also be formulated for parenteral administration (e.g., by injection, for example, bolus injection or continuous infusion) and may be presented in unit dose form in ampules, pre-filled syringes, small bolus infusion containers or in multi-does containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidernis, the compounds may be formulated as ointments, creams or lotions, or as the active ingredient of a transdermal patch. Suitable transdermal delivery systems are disclosed, for example, in Fisher et al. (U.S. Pat. No. 4,788,603, incorporated herein by reference) or Bawas et al. (U.S. Pat. Nos. 4,931,279, 4,668, 504 and 4,713,224; all incorporated herein by reference). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredient may also be delivered via iontophoresis, e.g., as disclosed in U.S. Pat. Nos. 4,140,122, 4,383,529, or 4,051,842; incorporated herein by reference.

Compositions suitable for topical administration in the mouth include unit dosage forms such as lozenges comprising active ingredient in a flavored base, usually sucrose and acacia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described compositions may be adapted to provide sustained release of the active ingredient employed, e.g., by combination thereof with certain hydrophilic polymer matrices, e.g., comprising natural gels, synthetic polymer gels or mixtures thereof.

The pharmaceutical compositions according to the invention may also contain other adjuvants such as flavorings, coloring, antimicrobial agents, or preservatives.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, one of skill in the art understands how to extrapolate in vivo data obtained in a model organism, such as an athymic nude mice inoculated with human tumor cell lines, to another mammal, such as a human. These extrapolations are not simply based on the weights of the two organisms, but rather incorporate differences in metabolism, differences in pharmacological delivery, and administrative routes. Based on these types of considerations, a suitable dose will, in alternative embodiments, typically be in the range of from about 0.5 to about 10 mg/kg/day, or from about 1 to about 20 mg/kg of body weight per day, or from about 5 to about 50 mg/kg/day.

The desired dose may conveniently be presented in a single dose or as divided doses administered at appropriate intervals, for example, as two, three, four or more sub-doses per day. The sub-dose, as necessary by one skilled in the art, may itself be further divided, e.g., into a number of discrete loosely spaced administrations.

One skilled in the art will recognize that dosage and dosage forms outside these typical ranges can be tested and, where appropriate, be used in the methods of this invention.

Combinations with Other Active Agents

According to another aspect of the invention, pharmaceutical compositions of matter useful for the treatment of cancer are provided that contain, in addition to the aforementioned compounds, an additional therapeutic agent. Such agents may be chemotherapeutic agents, ablation or other therapeutic hormones, antineoplastic agents, monoclonal antibodies useful against cancers and angiogenesis inhibitors. The following discussion highlights some agents in this respect, which are illustrative, not limitative. A wide variety of other effective agents also may be used.

Among hormones which may be used in combination with the present inventive compounds, diethylstilbestrol (DES), leuprolide, flutamide, cyproterone acetate, ketoconazole and amino glutethimide.

Among antineoplastic and anticancer agents that may be used in combination with the inventive compounds, 5-fluorouracil, vinblastine sulfate, estramustine phosphate, suramin and strontium-89. Other chemotherapeutics useful in combination and within the scope of the present invention are buserelin, chlorotranisene, chromic phosphate, cisplatin, cyclophosphamide, dexamethasone, doxorubicin, estradiol, estradiol valerate, estrogens conjugated and esterified, estrone, ethinyl estradiol, floxuridine, goserelin, hydroxyurea, melphalan, methotrexate, mitomycin and prednisone.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

The following examples are given to illustrate the invention and are not intended to be inclusive in any manner:

EXAMPLES

Example 1

4-[3-(1-Adamantyl)-4,5-methylenedioxyphenyl]-benzylidene-2,4-thiazolidinedione, which may hereinafter be referred to as "Compound 1"

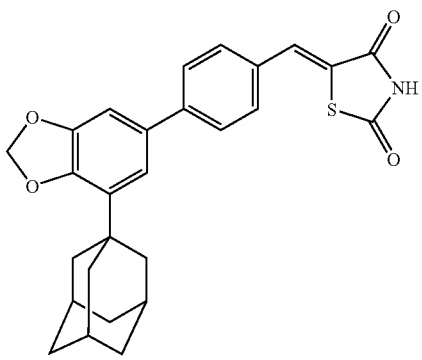

A solution of toluene (10 mL), piperidine (10 μL), acetic acid (10 μL), 4-[3-(1-adamantyl)-4,5-methylenedioxyphenyl]-benzaldehyde (0.400 g, 1.11 mmol) and 2,4-thiazolidinedione (0.130 g, 1.11 mmol) was heated at reflux overnight under an argon atmosphere. The reaction mixture was cooled to room temperature, and the resulting crystalline compound was filtered, washed with toluene and ethanol. The yellow solid was dried under high vacuum to afford 0.390 g (76%) of 4-[3-(1-adamantyl)-4,5-methylenedioxyphenyl]-benzylidene-2,4-thiazolidinedione, mp 308° (dec).
$^1$H NMR (500 MHz; DMSO-d$_6$): 1.74 (s, 6H), 2.04 (s, 9H), 6.05 (s, 2H), 7.06 (d, J=1.5 Hz, 1H), 7.20 (d, J=1.5 Hz, 1H), 7.63 (d, J=8.0 Hz, 2H), 7.78 (d, J=8.0 Hz, 2H), 7.81 (s, 1H), 12.5–12.7 (brs, 1H).

The intermediate 4-[3-(1-Adamantyl)-4,5-methylenedioxyphenyl]-benzaldehyde was prepared as follows:

a. 4-[3-(1-Adamantyl)-4,5-methylenedioxyphenyl]-benzaldehyde.

A mixture of 3-(1-adamantyl)-4,5-methylenedioxy-1-bromobenzene (2.00 g, 5.97 mmol), 4-formylphenylboronic acid (1.07 g, 7.16 mmol) and potassium carbonate (1.86 g, 13.42 mmol) in 1,2-dimethoxyethane (50 mL) and water (2.5 mL) was degassed with argon for 30 minutes. Tetrakis(triphenylphosphine)palladium(0) (0.34 g, 0.298 mmol) was added and the mixture heated at reflux under argon overnight. The solution was cooled to room temperature, diluted with ethyl acetate (200 mL) and washed successively with water (100 mL) and brine (100 mL), dried over anhydrous magnesium sulfate, filtered and evaporated. The residue was purified on silica gel (eluent: hexane:ethyl acetate, 95:5) to give 1.82 g of 4-[3-(1-Adamantyl)-4,5-methylenedioxy phenyl]-benzaldehyde (85%). $^1$H NMR (500 MHz; CDCl$_3$): δ 1.79 (s, 6H); 2.08 (s, 9H); 6.01 (s, 2H); 7.00 (d, J=2.0 Hz, 1H); 7.04 (d, J=2.0 Hz, 1H); 7.68 (d, J=8.1 Hz, 2H); 7.91 (d, J=8.1 Hz, 2H); 10.03 (s, 1H).

b. 3-(1-Adamantyl)-4,5-methylenedioxy-1-bromobenzene.

To a mixture of 3,4-methylenedioxy-1-bromobenzene (5.00 g, 24.87 mmol) and 1-adamantanol (3.79 g, 24.87 mmol) in CH$_2$Cl$_2$ (50 mL) under an atmosphere of argon was added sulfuric acid (2.0 mL) at room temperature. After stirring for 3 days the resulting mixture was diluted with CH$_2$Cl$_2$ and washed with water. The aqueous layer was extracted with CH$_2$Cl$_2$ and the combined organics were washed successively with water, brine and dried (MgSO$_4$). The mixture was filter, evaporated and the residue purified on silica gel (hexane) to give 4.41 g of 3-(1-adamantyl)-4,5-methylenedioxy-1-bromobenzene (53%) as a white solid, mp 135.5–136.0° C.

Example 2

4-[3-(1-Adamantyl)-4,5-methylenedioxyphenyl]-benzylidene-2-thioxo-4-thiazolidinone, which may hereinafter be referred to as "Compound 2"

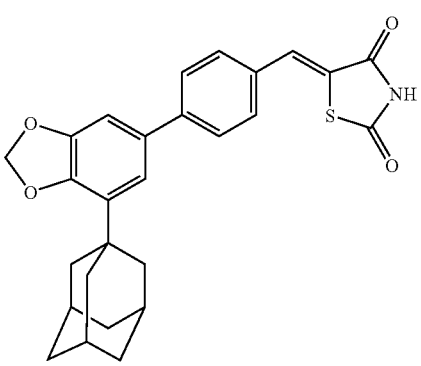

A solution of toluene (100 mL), piperidine (100 μL), acetic acid (100 μL), 4-[3-(1-adamantyl)-4,5-methylenedioxyphenyl]-benzaldehyde (1.50 g, 4.16 mmol, see Example 1a) and 2-thioxo-4-thiazolidinone (0.554 g, 4.16 mmol) was heated at reflux overnight under an argon atmosphere. Within 20 minutes an orange-yellow solid formed. A Dean-Stark trap was attached and after 48 hours the reaction mixture was cooled to room temperature, and the resulting crystalline compound was filtered and washed with ethanol. The yellow solid was dried under high vacuum to afford 1.50 g (76%) of 4-[3-(1-adamantyl)-4,5-methylenedioxyphenyl]-benzylidene-2,4-thiazolidinedione, mp 337.5–338.5° (dec). $^1$H NMR (500 MHz; DMSO-$d_6$): 1.75 (s, 6H), 2.05 (s, 9H), 6.05 (s, 2H), 7.07 (s, 1H), 7.22 (s, 1H), 7.63 (d, J=8.0 Hz, 1H), 7.80 (d, J=8.0 Hz, 1H), 13.6–13.9 (brs, 1H).

Example 3

6-[3-(1-Adamantyl)-4,5-methylenedioxyphenyl]-naphthalen-2-yl-methylene-2,4-thiazolidinedione, which may hereinafter be referred to as "Compound 3"

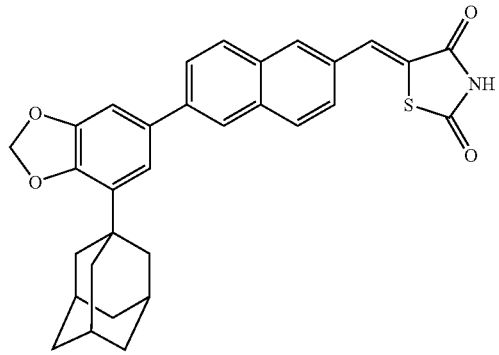

A mixture of toluene (10 mL), piperidine (10 μL), acetic acid (10 μL), 6-[3-(1-adamantyl)-4,5-methylenedioxyphenyl]-2-naphthaldehyde (0.400 g, 0.974 mmol) and 2,4-thiazolidinedione (0.114 g, 0.974 mmol) was heated at reflux overnight under an argon atmosphere. The reaction mixture was cooled to room temperature, and the resulting crystalline compound was filtered, washed with toluene and ethanol. The yellow solid was dried under high vacuum to afford 0.344 g (69%) of 6-[3-(1-adamantyl)-4,5-methylenedioxyphenyl]-naphthalen-2-yl-methylene-2,4-thiazolidinedione, mp 304–306° (dec). $^1$H NMR (500 MHz; DMSO-$d_6$): 1.76 (s, 6H), 2.07 (s, 9H), 6.06 (s, 2H), 7.16 (d, J=1.6 Hz, 1H), 7.29 (s, 1H), 7.68 (dd, J=1.0 Hz, J=9.0 Hz, 1H), 7.88 (d, J=9.0 Hz, 1H), 7.93 (s, 1H), 8.06 (d, J=9.0 Hz, 1H), 8.08 (d, J=8.8 Hz, 1H), 8.17 (s, 1H), 8.19 (s, 1H), 12.5–12.7 (brs, 1H).

The intermediate 6-[3-(1-adamantyl)-4,5-methylenedioxyphenyl]-2-naphthaldehyde was prepared as follows:

a. 6-[3-(1-Adamantyl)-4,5-methylenedioxyphenyl]-2-naphthaldehyde.

A mixture of 3-(1-adamantyl)-4,5-methylenedioxy-1-phenyl boronic acid (1.20 g, 4.00 mmol), 6-bromo-2-naphthaldehyde (0.89 g, 3.81 mmol) and potassium carbonate (1.18 g, 8.57 mmol) in 1,2-dimethoxyethane (40 mL) and water (4 mL) was degassed with argon for 30 minutes. Tetrakis(triphenylphosphine)palladium(0) (0.22 g, 0.190 mmol) was added and the mixture heated at reflux under argon overnight. The solution was cooled to room temperature, diluted with ethyl acetate:$CH_2Cl_2$ (1:1, 200 mL) and washed successively with water (100 mL) and brine (100 mL), dried over anhydrous magnesium sulfate, filtered and evaporated. The residue was purified on silica gel (eluent: hexane:$CH_2Cl_2$, 3:2 to 2:3) to give 1.27 g of 6-[3-(1-adamantyl)-4,5-methylenedioxyphenyl]-2-naphthaldehyde (81%). $^1$H NMR (500 MHz; CDCl$_3$): δ 1.81 (s, 6H); 2.12 (s, 9H); 6.02 (s, 2H); 7.09 (s, 1H); 7.12 (d, J=2.0 Hz, 1H), 7.79 (dd, J=2.0 Hz, J=8.0 Hz, 1H), 7.97 (s, 2H), 8.00 (s, 1H); 8.03 (d, J=8.5 Hz, 1H), 8.34 (s, 1H), 10.16 (s, 1H).

b. 3-(1-Adamantyl)-4,5-methylenedioxy-1-phenyl boronic acid.

To a mixture of 3-(1-adamantyl)-4,5-methylenedioxy-1-bromobenzene (see 1b, 2.00 g, 5.97 mmol) in THF (10 mL) cooled to −75° C. under an atmosphere of argon was added n-BuLi (3.6 mL, 2.5 M, 8.95 mmol) dropwise. The resulting suspension was stirred for 15 minutes and triisopropylborate (4.1 mL, 3.37 g, 17.90 mmol) was added dropwise via syringe. The mixture was warmed to 0° C. and 1.0 N HCl (20 mL) was slowly added and allowed to warm to RT. After 90 minutes the mixture was diluted with ethyl acetate (150 mL) and the layers separated, the aqueous layer was extracted once with ethyl acetate and the two organic layers combined. The resulting organic layer was washed with water (50 mL), brine (50 mL) and dried (Mg$_2$SO$_4$). The mixture was filtered, evaporated and the residue stirred in hexane. The resulting white suspension was filtered and the white solid dried under high vacuum to afford 1.35 g of 3-(1-adamantyl)-4,5-methylenedioxy-1-phenylboronic acid (75%). $^1$H NMR (500 MHz; CDCl$_3$): δ 1.73 (s, 6H); 1.99 (s, 9H); 5.95 (s, 2H); 7.18 (s, 1H); 7.27 (s, 1H); 7.87 (s, 2H).

c. 6-Bromo-2-naphthaldehyde.

To a solution of 6-bromo-2-naphthylmethyl alcohol (6.71 g, 28.3 mmol) in $CH_2Cl_2$ (350 mL) was added pyridinium chlorochromate (6.71 g, 31.13 mmol) all at once. The mixture visually went from orange-red to black over 30 minutes and 150 mL of ether was added. The black mixture was passed through a silica gel column and eluted with ether. The solvents were evaporated and the solid was further purified on silica gel (hexane:$CH_2Cl_2$ 1:1) to give 6.25 g of 6-bromo-2-naphthaldehyde (94%) as a white solid. %). $^1$H NMR (300 MHz; CDCl$_3$): δ 7.65 (dd, $J_1$=2.0 Hz, $J_2$=9.0 Hz, 1H); 7.84 (t, J=8.0 Hz, 2H); 7.97 (dd, $J_1$=2.0 Hz, $J_2$=8.0 Hz, 1H); 8.06 (d, J=2.0 Hz, 1H); 8.29 (s, 1H); 10.14 (s, 1H); $^{13}$C NMR (300 MHz; CDCl$_3$): ppm 123.5, 123.9, 128.0, 130.1, 130.5, 130.8, 130.9, 133.9, 134.2, 137.1, 191.6.

d. 6-Bromo-2-naphthylmethyl alcohol.

To a solution of ethyl 6-bromo-2-naphthoate (7.90 g, 28.30 mmol) in 200 mL toluene at −78° C. under an atmosphere of argon was added DIBAL (84.9 mL, 1.0 M in toluene, 84.91 mmol) via transfer needle over 20 minutes. After 1 hour the reaction mixture was quenched with ethyl acetate and the resulting mixture was allowed to warm to RT. The mixture was diluted with ethyl acetate and washed with 1.0 N HCl, water and brine. The organics were dried with magnesium sulfate, filtered and evaporated to give 7.51 g of 6-bromo-2-naphthylmethyl alcohol as a white solid and used without further purification in the oxidation (step c). $^1$H NMR (300 MHz; CDCl$_3$): δ 4.86 (s, 2H); 7.50 (dd, $J_1$=2.0 Hz, $J_2$=8.0 Hz, 1H); 7.57 (d, J=2.0 Hz, 1H); 7.70 (d, J=9.0 Hz, 1H); 7.75 (d, J=8.0 Hz, 1H); 7.79 (s, 1H); 8.00 (d, J=2.0 Hz, 1H).

e. Ethyl 6-bromo-2-naphthoate.

A mixture of 6-bromo-2-naphthoic acid (6.18 g, 24.6 mmol), iodoethane (19.7 mL, 38.39 g, 246.1 mmol) and Cs$_2$CO$_3$ (12.03 g, 36.9 mmol) in acetonitrile (200 mL) under an atmosphere was heated to reflux overnight. The resulting mixture was filtered and evaporated. The solid was dissolved in ethyl acetate and washed with water (4×), brine and dried (Mg$_2$SO$_4$). The mixture was filtered and evaporated to give 6.68 g of ethyl 6-bromo-2-naphthoate (97%) as a solid. $^1$H NMR (500 MHz; CDCl$_3$): δ 1.45 (t, J=7.0 Hz, 3H); 4.44 (q, J=7.0 Hz, 2H); 7.61 (dd, J$_1$=2.0 Hz, J$_2$=9.0 Hz, 1H); 7.79 (d, J=8.5 Hz, 1H); 7.82 (d, J =9.0 Hz, 1H); 8.00–8.11 (m, 2H); 857 (brs, 1H), Example 4

4-[3-(2-Methoxyphenyl)-4,5-methylenedioxyphenyl]-benzylidene-2,4-thiazolidinedione, which may hereinafter be referred to as "Compound 4"

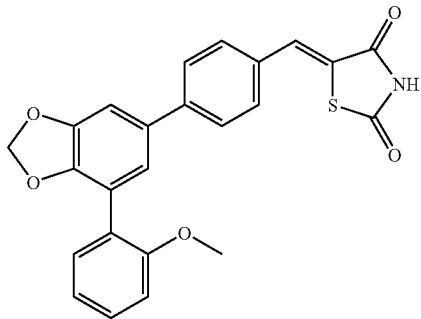

A solution of toluene (10 mL), piperidine (10 μL), acetic acid (10 μL), 4-[3-(2-methoxyphenyl)-4,5-methylenedioxyphenyl]benzaldehyde (0.164 g, 0.493 mmol) and 2,4-thiazolidinedione (0.0578 g, 0.493 mmol) was heated at reflux overnight under an argon atmosphere. The reaction mixture was cooled to room temperature, and the resulting crystalline compound was filtered, washed with ethanol. The yellow solid was dried under high vacuum to afford 0.125 g (59%) of 4-[3-(2-methoxyphenyl)-4,5-methylenedioxyphenyl]-benzylidene-2,4-thiazolidinedione, mp 227–228° C. (dec.). $^1$H NMR (300 MHz; DMSO-d$_6$): 3.77 (s, 3H), 6.05 (s, 2H), 7.12 (t, J=7.5 Hz, 1H), 7.12 (d, J=8.7 Hz, 1H), 7.23 (s, 1H), 7.30 (s, 1H), 7.33–7.43 (m, 2H), 7.63 (d, J=7.8 Hz, 2H), 7.80 (d, J=7.8 Hz, 2H), 7.81 (s, 1H), 12.5–12.7 (brs, 1H). $^{13}$C NMR (75 MHz; DMSO-d$_6$): 56.3, 56.4, 101.9, 106.6, 112.4, 120.8, 121.0, 123.0, 123.6, 124.7, 127.8, 130.2, 131.3, 131.4, 132.0, 132.2, 133.1, 142.2, 145.9, 148.7, 157.1, 168.0, 168.4.

The intermediate 4-[3-(2-methoxyphenyl)-4,5-methylenedioxyphenyl]benzaldehyde was prepared as follows:

a. 4-[3-(2-Methoxyphenyl)-4,5-methylenedioxyphenyl]benzaldehyde.

A mixture of 3-(2-methoxyphenyl)-4,5-methylenedioxyphenyl trifluoromethane-sulfonate (0.315 g, 0.864 mmol), 4-formylphenylboronic acid (0.136 g, 0.907 mmol) and potassium carbonate (0.358 g, 2.59 mmol) in 1,2-dimethoxyethane (15 mL) and water (1.5 mL) was degassed with argon for 30 minutes.

Tetrakis(triphenylphosphine)-palladium (0) (0.050 g, 0.0432 mmol) was added and the mixture heated at reflux under argon overnight. The solution was cooled to room temperature, diluted with ethyl acetate (100 mL) and washed successively with water (50 mL) and brine (50 mL), dried over anhydrous magnesium sulfate, filtered and evaporated. The residue was purified on silica gel (eluent: hexane:ethyl acetate, 85:15) to give 0.192 g of 4-[3-(2-methoxyphenyl)-4,5-methylenedioxyphenyl]]benzaldehyde (67%). $^1$H NMR (300 MHz; DMSO-d$_6$): δ 3.77 (s, 3H); 6.07 (s, 2H); 7.02 (t, J=7.0 Hz, 1H); 7.12 (d, J=9.0 Hz, 1H); 7.25 (d, J=1.5 Hz, 1H); 7.33 (d, J=1.5 Hz, 1H); 7.34–7.45 (m, 2H), 7.87 (d, J=8.0 Hz, 2H); 7.93 (d, J=8.0 Hz, 2H); 10.01 (s, 1H);

b. 3-(2-methoxyphenyl)-4,5-methylenedioxyphenyl trifluoromethane-sulfonate.

To a solution of 3-(2-methoxyphenyl)-4,5-methylenedioxyphenol (0.52 g, 2.13 mmol) in CH$_2$Cl$_2$ (15 mL) and pyridine (0.253 g, 0.978 mL, 3.19 mmol) at 0° C. was added triflic anhydride (0.901 g, 3.19 mmol, 0.54 mL) dropwise under an atmosphere of argon. After stirring overnight the resulting mixture was diluted with CH$_2$Cl$_2$ and washed with water, brine and dried (MgSO$_4$). The mixture was filter, evaporated and the residue dried under high vacuum to give 0.652 g of 3-(2-methoxyphenyl)-4,5-methylenedioxyphenyl trifluoromethanesulfonate as a dark oil (81%). $^1$H NMR (300 MHz; CDCl$_3$): δ 3.84 (s, 3H); 6.05 (s, 2H); 6.74 (d, J=1.2 Hz, 1H); 6.96 (d, J=1.5 Hz, 1H); 6.97–7.10 (m, 2H); 7.30–7.45 (m, 2H).

c. 3-(2-Methoxyphenyl)-4,5-methylenedioxyphenol.

A solution of 3-(2-methoxyphenyl)-4,5-methylenedioxybenzaldehyde (0.850 g, 3.32 mmol), m-chloroperbenzoic acid (1.431 g, 8.29 mmol) in CH$_2$Cl$_2$ (25 mL) was heated to reflux overnight. The resulting orange mixture was evaporated, dissolved into MeOH (15 mL) and 2.5 M NaOH (6 mL) and stirred for 45 minutes. The dark mixture was diluted with ethyl acetate and acidified with 1.0 N HCl. The layers were separated and the organics washed successively with water, 0.5 M NaHCO$_3$, water, brine and dried (MgSO$_4$). The mixture was filtered, evaporated and the residue was purified on silica gel (hexane:ethyl acetate 4:1) to give 0.55 g of 3-(2-methoxyphenyl)-4,5-methylenedioxyphenol (68%) as a tan solid, $^1$H NMR (500 MHz; CDCl$_3$): δ 3.82 (s, 3H); 5.91 (s, 2H); 6.40–6.45 (m, 2H); 6.99 (d, J=9.0 Hz, 1H); 7.02 (d, J=7.0 Hz, 1H); 7.40–7.30 (m, 2H).

d. 3-(2-Methoxyphenyl)-4,5-methylenedioxybenzaldehyde.

A mixture of 3-bromo-4,5-methylenedioxybenzaldehyde (2.51 g, 10.97 mmol), 2-methoxyphenylboronic acid (2.00 g, 13.16 mmol) and potassium carbonate (3.41 g, 24.68 mmol) in 1,2-dimethoxyethane (70 mL) and water (3.5 mL) was degassed with argon for 30 minutes. Tetrakis(triphenylphosphine)palladium(0) (0.63 g, 0.548 mmol) was added and the mixture heated at reflux under argon overnight. The solution was cooled to room temperature, diluted with ethyl acetate (100 mL) and washed successively with water (50 mL) and brine (50 mL), dried over anhydrous magnesium sulfate, filtered and evaporated. The residue was purified on silica gel (eluent: hexane:ether, 9:1) to give 0.910 g of 3-(2-methoxyphenyl)-4,5-methylenedioxybenzaldehyde (32%) as a white solid. $^1$H NMR (300 MHz; CDCl$_3$): δ 3.84 (s, 3H); 6.07 (s, 2H); 7.00–7.10 (m, 2H); 7.31 (brs, 1H); 7.30–7.45 (m, 2H); 7.53 (brs, 1H); 9.83 (s, 1H).

e. 3-Bromo-4,5-methylenedioxybenzaldehyde.

To a stirred solution of 3-bromo-4,5-dihydroxybenzaldehyde (10.50 g, 48.38 mmol) in DMF (145 mL) was added anhydrous KF (14.02 g, 241.9 mmol, dried for 24 hours under high vacuum/P$_2$O$_5$). After 15 minutes CH$_2$Br$_2$ was added all at once and the resulting mixture heated to 100–105° C. for 4 hours. The mixture was evaporated under reduced pressure and the residue was taken up in ether and water. The layers were separated, the aqueous layer was washed with ether (3×). The combined ether layers were washed with water (2×), brine and dried over anhydrous magnesium sulfate. After filtration, the mixture was concentrated under reduced pressure to give 8.42 g of 3-bromo-4, 5-methylenedioxybenzaldehyde (76%) as a brownish solid. $^1$H NMR (500 MHz; CDCl$_3$): δ 6.16 (s, 2H); 7.26 (s, 1H); 7.55 (s, 1H); 9.77 (s, 1H).

f. 3-Bromo-4,5-dihydroxybenzaldehyde.

To a vigorously stirred suspension of 3-bromo4-hydroxy-5-methoxy-benzaldehyde (15.20 g, 65.8 mmol), AlCl$_3$ (9.65 g, 72.4 mmol) in CH$_2$Cl$_2$ (100 mL) at 0° C. with exclusion of moisture was added pyridine (22.90 g, 290 mmol, 23.4 mL) to keep the temperature below 32° C. The resulting clear dark solution was heated to reflux for 24 hours and cooled to RT. The mixture was poured into a slurry of 1 N HCl and ice. The CH$_2$Cl$_2$ layer was removed and the aqueous suspension was extracted with ether till clear. The combined ether layers were dried over anhydrous magnesium sulfate, filtered and evaporated to a volume of approximately 200 mL and cooled to 0° C. for 2 hours. The resulting suspension was collected by filtration and dried under high vacuum to give 10.12 g of 3-bromo-4,5-dihydroxybenzaldehyde (71%) as a tan solid. $^1$H NMR (500 MHz; CDCl$_3$): δ 7.18 (s, 1H); 7.37 (d, J=2.0 Hz, 1H); 8.48 (brs, 1H); 9.40 (brs, 1H); 9.56 (s, 1H).

Example 5

4-[3-(1-Adamantyl)-4-methoxyphenyl]-benzylidene-2,4-thiazolidinedione, which may hereinafter be referred to as "Compound 5"

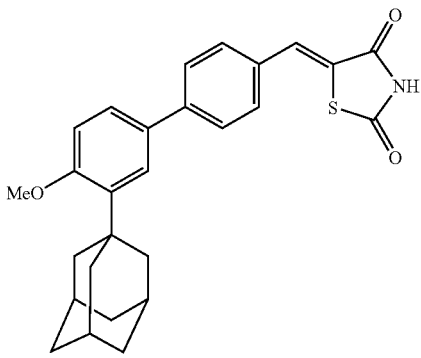

A solution of toluene (6 mL), piperidine (10 μL), acetic acid (10 μL), 4-[3-(1-adamantyl)-4-methoxyphenyl]benzaldehyde (0.337 g, 0.97 mmol) and 2,4-thiazolidinedione (0.114 g, 0.97 mmol) was heated at reflux overnight under an argon atmosphere. The reaction mixture was cooled to room temperature, and the resulting crystalline compound was filtered, washed with toluene and ethanol. The yellow solid was dried under high vacuum to afford 0.375 g (87%) of 4-[3-(1-adamantyl)-4-methoxyphenyl]benzylidene-2,4-thiazolidinedione, mp 304–306° C. $^1$H NMR (300 MHz; DMSO-d$_6$): 1.75 (s, 6H), [2.06 (s), 2.11 (s), 9 H], 3.85 (s, 3H), 7.09 (d, J=8.7 Hz, 1H), 7.46 (d, J=2.3 Hz, 1H), 7.57 (dd, J=8.7 Hz, J=2.3 Hz, 1H), 7.65 (d, J=8.4 Hz, 2H), 7.80 (d, J=8.4 Hz, 2H), 7.82 (s, 1H), 12.4–12.7 (brs, 1H).

The intermediate 4-[3-(1-adamantyl)-4-methoxyphenyl]benzaldehyde was prepared as follows:

A mixture of 3-(1-adamantyl)-4-methoxy-1-bromobenzene (1.000 g, 3.11 mmol, prepared in a similar manner as described by Charpentier, B. et al. in J. Med. Chem. 1995, 38, 4993–5006), 4-formylphenylboronic acid (0.559 g, 3.73 mmol) and potassium carbonate (1.719 g, 12.44 mmol) in 10.5 mL of DME and 1.5 mL of water was degassed with argon for 30 minutes. Tetrakis(triphenylphosphine)palladium(0) (0.185 g, 0.16 mmol) was added and the mixture heated at reflux under argon overnight. The solution was cooled to room temperature, diluted with ethyl acetate (200 mL) and washed successively with water (100 mL) and brine (100 mL), dried over anhydrous magnesium sulfate, filtered and evaporated. The residue was purified on silica gel (eluent: hexane:ethyl acetate, 95:5) to give 0.372 g of 4-[3-(1-adamantyl)-4-methoxyphenyl]benzaldehyde (34%). $^1$H NMR (300 MHz; CDCl$_3$): δ 1.80 (s, 6H), [2.10 (brs), 216 (s), 9 H], 3.91 (s, 3H), 6.98 (d, J=8.4 Hz, 1H), 7.48 (dd, J$_1$=8.4 Hz, J$_2$=2.4 Hz, 1H), 7.51 (d, J=2.4 Hz, 1H), 7.73 (d, J=8.7 Hz, 2H), 7.93 (d, J=8.7 Hz, 2H), 10.04 (s, 1H).

Example 6

4-[3-(1-Adamantyl)-4-methoxyphenyl]-benzylidene-2-thioxo-4-thiazolidinedione, which may hereinafter be referred to as "Compound 6"

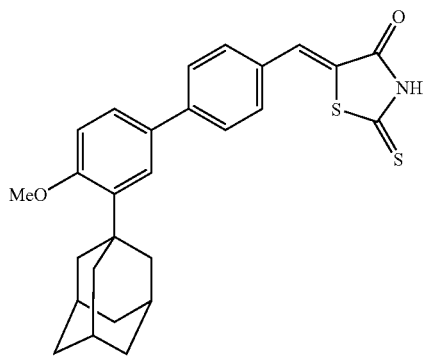

A solution of toluene (6 mL), piperidine (9 μL), acetic acid (8 μL), 4-[3-(1-adamantyl)-4-methoxyphenyl]-benzaldehyde (0.303 g, 0.87 mmol, see Example 5) and 2-thioxo-4-thiazolidinone (0.116 g, 0.87 mmol) was heated at reflux under an argon atmosphere. After 48 hours the reaction mixture was cooled to room temperature, and the resulting crystalline compound was filtered and washed with ethanol. The yellow solid was dried under high vacuum to afford 0.293 g (72%) of 4-[3-(1-adamantyl)-4-methoxyphenyl]-benzylidene-2-thioxo-4-thiazolidinedione, mp 313–317°. $^1$H NMR (300 MHz; DMSO-d$_6$): 1.73 (s, 6H), [2.04 (s), 2.08(s), 9 H], 3.84 (s, 3H), 7.07 (d, J=8.7 Hz, 1H), 7.46 (d, J=1.0 Hz, 1H), 7.56 (dd, J$_1$=8.7 Hz, J$_2$=1.0 Hz, 1H), 7.63 (d, J=8.1 Hz, 2H), 7.65 (s, 1H), 7.79 (d, J=8.1 Hz, 2H), 13.6–14.0 (brs, 1H).

Example 7

4-[3-(1-Adamantyl)-4-hydroxyphenyl]benzylidene-2,4-thiazolidinedione,

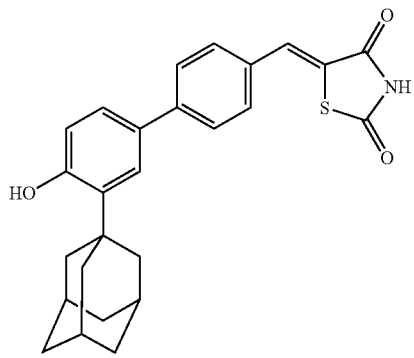

which may hereinafter be referred to as "Compound 7."

A solution of toluene (180 mL), piperidine (0.60 mL), acetic acid (0.63 mL), 4-[3-(1-adamantyl)-4-hydroxyphenyl]benzaldehyde (6.08 g, 18.30 mmol) and 2,4-thiazolidinedione (2.14 g, 18.30 mmol) was heated at reflux for 12 hours under an argon atmosphere. The resulting suspension was filtered hot and the solid was stirred at room temperature in 210 mL of H$_2$O/EtOH (6:1). After 30 minutes the solid was filtered and dried under high vacuum to afford 5.6 g (71%) of 4-[3-(1-adamantyl)-4-hydroxyphenyl]benzylidene-2,4-thiazolidinedione, mp 307–308.5° C. $^1$H NMR (300 MHz; DMSO-d$_6$): δ 1.75 (brs, 6H), 2.05–2.13 (m, 9H), 6.88 (dd, J$_1$=1.8 Hz, J$_2$=8.7 Hz, 1H), 7.40–7.42 (m, 2H), 7.61–7.64 (m, 2H), 7.73–7.79 (m, 3H), 9.62 (s, 1H), 12.57 (brs, 1H).

The intermediate 4-[3-(1-adamantyl)-4-hydroxyphenyl]benzaldehyde was prepared as follows:

a. 4-[3-(1-Adamantyl)-4-hydroxyphenyl]benzaldehyde.

To a solution of 4-[3-(1-adamantyl)-4-methoxymethoxyphenyl]benzaldehyde (6.88 g, 18.30 mmol) in 200 mL of THF:isopropanol (1:1) was a added 30 mL of 6 N HCl at room temperature. After 20 hours 30 mL of 12 N HCl was added. After 57 hours starting material was still present, 60 mL of additional 12 N HCl was added and stirred for 16 hours. The resulting mixture was diluted with water and extracted with ether (2×200 mL). The combined organics were washed with water (150 mL), brine (100 mL), dried over anhydrous magnesium sulfate, filtered and evaporated to give 6.00 g (99%) of 4-[3-(1-adamantyl)-4-hydroxyphenyl]benzaldehyde as a solid. $^1$H NMR (300 MHz; DMSO-d6): δ 1.72 (brs, 6H), 2.00–2.20 (m, 9H), 6.88 (d, J=8.7 Hz, 1H), 7.36–7.48 (m, 2H), 7.78 (d, J=8.1 Hz, 2H), 7.90 (d, J=8.1 Hz, 2H), 9.67 (s, 1H), 9.98 (s, 1H).

b. 4-[3-(1-Adamantyl)-4-methoxymethoxyphenyl]benzaldehyde.

A mixture of 3-(1-adamantyl)-4-methoxymethoxy-bromobenzene (8.48 g, 24.16 mmol), 4-formylphenylboronic acid (3.99 g, 26.57 mmol) and potassium carbonate (10.02 g, 72.47 mmol) in 300 mL of toluene:EtOH (4:1) and water (15 mL) was degassed with argon for 30 minutes. Tetrakis(triphenylphosphine)palladium(0) (2.79 g, 2.41 mmol) was added and the mixture heated at reflux for 14 hours. The solution was cooled to room temperature, diluted with ethyl acetate and washed successively with water and brine, dried over anhydrous magnesium sulfate, filtered and evaporated. The residue was purified on silica gel (eluent: hexane:ether, 95:5) to give 7.01 g of 4-[3-(1-adamantyl)-4-methoxymethoxyphenyl]benzaldehyde (78%) as a solid. $^1$H NMR (300 MHz; CDCl$_3$): δ 1.80 (s, 6H), 2.10–2.17 (m, 9H), 3.55 (s, 3H), 5.29 (s, 2H), 7.20 (d, J=8.4 Hz, 1H), 7.44 (dd, J$_1$=8.7 Hz, J$_2$=2.4 Hz, 1H), 7.52 (d, J=2.4 Hz, 2H), 7.72 (d, J=8.4 Hz, 2H), 7.92 (d, J=7.8 Hz, 2H), 10.03 (s, 1H).

c. 3-(1-Adamantyl)-4-methoxymethoxy-bromobenzene.

To a mixture of 2-(1-adamantyl)-4-bromophenol (10.00 g, 32.57 mmol) in DMF (90 mL) cooled to 0° C. was added NaH (1.08 g, 80% in mineral oil, 35.83 mmol) under an atmosphere of argon. The mixture was allowed to warm to room temperature and subsequently stirred for 30 minutes. The resulting mixture was cooled to 0° C. and chloromethyl methyl ether (2.72 mL, 35.83 mmol) was added dropwise. After 14 hours at room temperature and the reaction mixture was poured into ice water and extracted with EtOAc (2×150 mL). The combined organic layers were washed water (100 mL), brine (100 mL), dried (MgSO$_4$) and filtered. The solvent was removed under reduced pressure and the resulting solid was purified on silica gel (hexane:ethyl acetate 99:1 to 97:3) to give 8.6 g (76%) of 3-(1-adamantyl)-4-methoxymethoxy-bromobenzene. $^1$H NMR (300 MHz; CDCl$_3$): δ 1.77 (s, 6H), 2.08 (s, 9H), 3.50 (s, 3H), 5.19 (s, 2H), 6.98 (d, J=8.7 Hz, 1H), 7.24 (dd, J$_1$=9.0 Hz, J$_2$=2.4 Hz, 1H), 7.32 (d, J=2.4 Hz, 1H).

d. 2-(1-Adamantyl)-4-bromophenol.

To a mixture of 4-bromophenol (34.60 g, 200 mmol) and 1-adamantanol (30.45 g, 200 mmol) in 100 mL of anhydrous CH$_2$Cl$_2$ at room temperature was added dropwise over 10–15 minutes concentrated H$_2$SO$_4$ (11 mL). After 1.5 hours a thick suspension resulted and the reaction was allowed to continue for a total of 24 hours. The suspension was carefully poured into ice water and neutralized with solid NaHCO$_3$. The resulting layers were separated and the aqueous layer extracted with CH$_2$Cl$_2$ (2×). The combined organics were washed with brine, dried (MgSO$_4$) and filtered. The solvent was removed under reduced pressure and the resulting solid was purified on silica gel (hexane:ethyl acetate 85:15), the impure fractions were further purified by recrystallization from hexane and the two lots combined to give 45.2 g (74%) of 2-(1-adamantyl)-4-bromophenol. $^1$H NMR (300 MHz; CDCl$_3$): δ 1.77 (s, 6H), 2.08 (s, 9H), 4.81 (s, 1H), 6.53 (d, J=8.4 Hz, 1H), 7.14 (dd, J$_1$=8.7 Hz, J$_2$=2.4 Hz, 1H), 7.29 (d, J=2.4 Hz, 1H).

Example 8

6-[3-(1-Adamantyl)-4-methoxyphenyl]-naphthalen-2-yl-methylene-2,4-thiazolidinedione, which may hereinafter be referred to as "Compound 8"

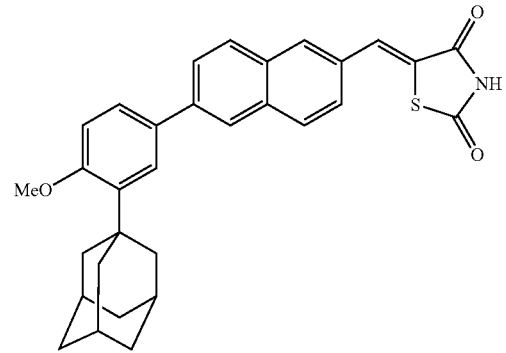

A solution of toluene (150 mL), piperidine (0.48 mL), acetic acid (0.51 mL), 6-[3-(1-adamantyl)-4-methoxyphenyl]-2-naphthaldehyde (5.84 g, 14.75 mmol) and 2,4-thiazolidinedione (1.73 g, 14.75 mmol) was heated at reflux for 18 hours under an argon atmosphere. The resulting suspension was filtered and the solid was stirred at room temperature in 30 mL of EtOH. After 30 minutes the solid was filtered and dried under high vacuum to afford 5.3 g (71%) of 6-[3-(1-adamantyl)-4-methoxyphenyl]-naphthalen-2-yl-methylene-2,4-thiazolidinedione, mp 286–287° C. $^1$H NMR (300 MHz; DMSO-d$_6$): 1.76 (brs, 6H), 2.07–2.14 (m, 9H), 3.87 (s, 3H), 7.11 (d, J=8.4 Hz, 1H), 7.58 (s, 1H), 7.66 (t, J=9.3 Hz, 2H), 7.88–7.93 (m, 2H), 8.09 (t, J=8.7 Hz, 2H), 8.18 (d, J=5.7 Hz, 2H), 12.63 (brs, 1H).

The intermediate 6-[3-(1-adamantyl)-4-methoxyphenyl]-2-naphthaldehyde was prepared as follows:

A mixture of 6-bromo-2-naphthaldehyde (1.17 g, 4.98 mmol, see Example 3c), 3-(1-adamantyl)-4-methoxyphenyl boronic acid (1.57 g, 5.48 mmol, prepared in a manner similar to that described in Example 3b.) and potassium carbonate (1.55 g, 11.20 mmol) in 75 mL of toluene and water (4 mL) was degassed with argon for 30 minutes. Tetrakis(triphenyl phosphine)palladium(0) (0.575 g, 0.50 mmol) was added and the mixture heated at reflux for 18 hours. The solution was cooled to room temperature, diluted with ethyl acetate and washed successively with water and brine, dried over anhydrous magnesium sulfate, filtered and evaporated. The residue was purified on silica gel (eluent: hexane:$CH_2Cl_2$, 3:2 to 1:1) to give 1.6 g of 6-[3-(1-adamantyl)-4-methoxyphenyl]-2-naphthaldehyde (82%) as a solid. $^1$H NMR (300 MHz; $CDCl_3$): δ 1.80 (s, 6H), 2.10–2.17(m, 9H), 3.90 (s, 3H), 6.99 (d, J=8.1 Hz, 1H), 7.52–7.60 (m, 2H), 7.82 (d, J=8.4 Hz, 1H), 7.95–8.02 (m, 4H), 8.32 (s, 1H), 10.13 (s, 1H).

Example 9

6-[3-(1-Adamantyl)-4-methoxyphenyl]-naphthalen-2-yl-methyl-2,4-thiazolidinedione, which may hereinafter be referred to as "Compound 9"

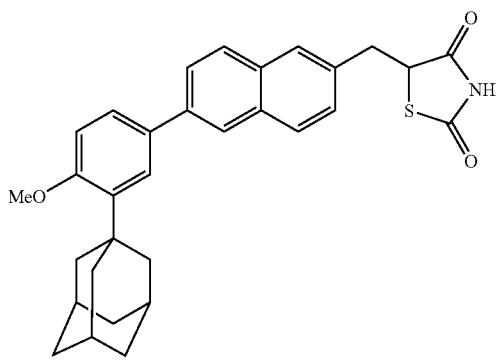

To a stirred solution of 2,4-thiazolidinedione (0.094 g, 0.80 mmol) in 4.0 mL of anhydrous THF at −78° C. under argon was added n-BuLi (0.58 mL of 2.5 M in hexanes). After 20 minutes, the reaction mixture was allowed to warm to 0° C. for 30 minutes then cooled to −78° C. To this mixture was added 6-[3-(1-adamantyl)-4-methoxyphenyl]-naphthalen-2-yl-methyliodide (0.177 g, 0.35 mmol) in 3 mL anhydrous THF and stirred at −78° C. for 30 minutes. The reaction mixture was warmed to room temperature. After 14 hours, the reaction mixture was diluted with water and extracted with EtOAc (2×50 mL). The combined organics were washed with water (100 mL), sat. $NH_4Cl$ (100 mL), brine (100 mL), dried over anhydrous magnesium sulfate, filtered and evaporated. The residue was purified on silica gel (eluent: hexane:EtOAc 4:1) to give 0.097 g of 6-[3-(1-adamantyl)-4-methoxyphenyl]-naphthalen-2-yl-methyl-2,4-thiazolidinedione (56%), mp 251–253° C. $^1$H NMR (300 MHz; DMSO-$d_6$): δ 1.80 (brs, 6H), 2.10–2.18 (m, 9H), 3.32 (dd, J=9.6 Hz, J=14.1 Hz, 1H), 3.72 (dd, J=3.6 Hz, J=14.1 Hz, 1H), 3.90 (s, 3H), 4.65 (dd, J=3.6 Hz, J=9.9 Hz, 1H), 6.99 (d, J=8.1 Hz, 1H), 7.36 (dd, J=1.5 Hz, J=8.4 Hz, 1H), 7.52 (dd, J=1.8 Hz, J=8.7 Hz, 1H), 7.57 (d, J=2.1 Hz, 1H), 7.70–7.76 (m, 2H), 7.84 (d, J=3.3 Hz, 1H), 7.87 (d, J=3.6 Hz, 1H), 7.96 (d, J=0.3 Hz, 1H), 8.13 (brs, 1H). $^{13}$C NMR (75 MHz; DMSO-$d_6$): 38.4, 46.6, 47.4, 62.7, 65.3, 122.6, 134.0, 134.7, 135.3, 137.3, 137.6, 137.9, 138.1, 141.5, 141.8, 142.3, 144.1, 147.7, 147.8, 168.1, 181.4, 185.5.

The intermediate 6-[3-(1-adamantyl)-4-methoxyphenyl]-naphthalen-2-yl-methyliodide was prepared as follows:

a. 6-[3-(1-Adamantyl)-4-methoxyphenyl]-naphthalen-2-yl-methyliodide.

To a solution of 6-[3-(1-adamantyl)-4-methoxyphenyl]-naphthalen-2-yl-methyl alcohol (0.365 g, 0.92 mmol), triphenylphosphine (0.366 g, 1.39 mmol) and imidazole (0.095 g, 1.39 mmol) in 7 mL of anhydrous THF at 0° C. was added dropwise a solution of $I_2$ (0.303 g, 1.19 mmol) in 4 mL of anhydrous THF. After 30 minutes the mixture was diluted with EtOAc and washed with sodium thiosulfate aq. (100 mL), brine (100 mL), dried with magnesium sulfate, filtered and evaporated. The residue was purified on silica gel (eluent: hexane:EtOAc 100 to 95:5) to give 0.210 g of 6-[3-(1-adamantyl)-4-methoxyphenyl]-naphthalen-2-yl-methyliodide (45%). $^1$H NMR (300 MHz; $CDCl_3$): δ 1.80 (s, 6H), 2.10–2.18 (m, 9H), 3.89 (s, 3H), 4.65 (s, 2H), 6.98 (d, J=8.7 Hz, 1H), 7.46–7.57 (m, 3H), 7.71–7.93(m, 5H).

b. 6-[3-(1-Adamantyl)-4-methoxyphenyl]-naphthalen-2-yl-methyl alcohol.

To a solution of 6-[3-(1-adamantyl)-4-methoxyphenyl]-2-naphthaldehyde (0.500 g, 1.26 mmol, see Example 9) in 15 mL toluene at −78° C. under an atmosphere of argon was added DIBAL (2.5 mL, 1.0 M in toluene, 3.79 mmol) via needle dropwise. After 1 hour the reaction mixture was quenched with ethyl acetate and the resulting mixture was allowed to warm to RT. The mixture was diluted with ethyl acetate and washed with 1.0 N HCl, water and brine. The organics were dried with magnesium sulfate, filtered and evaporated. The residue was purified on silica gel (eluent: $CH_2Cl_2$) to give 0.450 g of 6-[3-(1-adamantyl)-4-methoxyphenyl]-naphthalen-2-yl-methylalcohol (90%), mp 169–171° C. $^1$HNMR (300 MHz; $CDCl_3$): δ 1.80 (s, 6H), 2.10–2.18 (m, 9H), 3.90 (s, 3H), 4.86 (s, 2H), 6.98 (d, J=8.4 Hz, 1H), 7.24–7.25 (m, 1H), 7.46–7.59 (m, 3H), 7.71–7.74 (m, 1H), 7.80–7.89 (m, 3H), 7.97 (s, 1H).

Example 10

4-[3-(1-Adamantyl)-4-methoxymethoxyphenyl]-benzylidene-2,4-thiazolidinedione, which may hereinafter be referred to as "Compound 10"

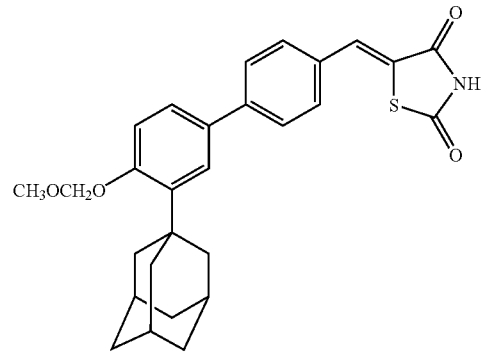

A solution of toluene 10 mL, piperidine 0.04 mL, acetic acid 0.04 mL, 6-[3-(1-adamantyl)-4-methoxymethoxyphenyl]-2-benzaldehyde (0.364 g, 0.97 mmol) and 2,4-thiazolidinedione (0.114 g, 0.97 mmol) was heated at reflux for 20 hours under an argon atmosphere. The resulting suspension was filtered and the solid was stirred at room temperature in 30 mL of EtOH. After 20 minutes the solid was filtered and dried under high vacuum to afford 0.280 g (61%) of 4-[3-(1-adamantyl)-4-methoxymethoxyphenyl]-benzylidene-2,4-thiazolidinedione, mp 253–254.5° C. $^1$H NMR (300 MHz; DMSO-$d_6$): 1.75 (brs, 6H), 2.06–2.13 (m, 9H), 3.45 (s, 3H), 5.29 (s, 2H), 7.13 (d, J=8.4 Hz, 1H), 7.49–7.54 (m, 2H), 7.64 (d, J=8.4 Hz, 2H), 7.77 (d, J=8.4 Hz, 2H), 7.82 (s, 1H), 12.63 (brs, 1H), $^{13}$C NMR (75 MHz; DMSO-$d_6$): 28.4, 36.5, 35.7, 56.0, 93.7, 114.7, 122.6, 124.9. 125.2, 126.8, 130.5, 131.1, 131.3, 131.4, 138.0, 142.0, 155.8, 167.1, 167.6.

The intermediate 6-[3-(1-adamantyl)-4-methoxymethoxyphenyl]-2-benzaldehyde was prepared as follows:

A mixture of 4-formylphenyl boronic acid (3.99 g, 26.57 mmol), 3-(1-adamantyl)-4-methoxymethoxyphenyl boronic acid (8.48 g, 24.16 mmol, prepared in a manner similar to that described in Example 3b.) and potassium carbonate (10.02 g, 72.47 mmol) in 300 mL of toluene:ethanol (4:1) and water (15 mL) was degassed with argon for 30 minutes. Tetrakis(triphenylphosphine) palladium(0) (0.279 g, 2.41 mmol) was added and the mixture heated at reflux for 14 hours. The solution was cooled to room temperature, diluted with ethyl acetate and washed successively with water and brine, dried over anhydrous magnesium sulfate, filtered and evaporated. The residue was purified on silica gel (eluent: hexane:EtOAc, 95:5) to give 7.01 g of 6-[3-(1-adamantyl)-4-methoxymethoxyphenyl]-2-benzaldehyde (78%) as a solid. $^1$H NMR (300 MHz; CDCl$_3$): 1.80 (brs, 6H), 2.10–2.17 (m, 9H), 3.54 (s, 3H), 5.29 (s, 2H), 7.20 (d, J=8.7 Hz, 1H), 7.43 (dd, J=8.7 Hz, J=2.4 Hz, 1H), 7.52 (d, J=2.4 Hz, 1H), 7.71 (d, J=8.4 Hz, 2H), 7.91 (d, J=7.8 Hz, 2H), 10.03 (s, 1H).

Example 11

6-[3-(1-Adamantyl)-4-(t-butyldimethylsilyloxy)phenyl]-benzylidene-2,4-thiazolidinedione, which may hereinafter be referred to as "Compound 11"

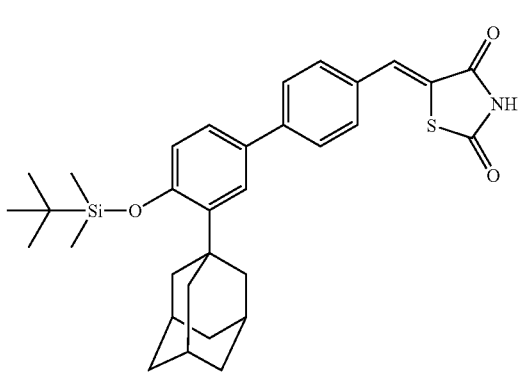

A solution of toluene (10 mL), piperidine (0.04 mL), acetic acid (0.04 mL), 6-[3-(1-adamantyl)-4-(t-butyldimethylsilyloxy)phenyl]-benzaldehyde (0.473 g, 1.06 mmol) and 2,4-thiazolidinedione (0.125 mg, 1.06 mmol) was heated at reflux for 23 hours under an argon atmosphere. The resulting suspension was filtered and the solid was stirred at room temperature in 30 mL of EtOH. After 20 minutes, the solid was filtered and dried under high vacuum to afford 0.400 g (70%) of 6-[3-(1-adamantyl)-4-(t-butyldimethylsilyloxy) phenyl]-benzylidene-2,4-thiazolidinedione, mp 277–278° C. $^1$H NMR (300 MHz, DMSO-$d_6$): δ 0.33 (s, 6H), 1.00 (s, 9H), 1.72 (brs, 6H), 2.01–2.09 (m, 9H), 6.89 (d, J=7.8 Hz, 1H), 7.42–7.44 (m, 2H), 7.61 (d, J=8.4 Hz, 2H), 7.73 (d, J=8.4 Hz, 2H), 7.79 (s, 1H), 12.60 (brs, 1H); $^{13}$C NMR (75 MHz, DMSO-$d_6$): ppm −3.6, 18.6, 26.1, 28.4, 36.5, 119.2, 122.5, 125.0, 125.4, 126.6, 130.5, 130.9, 131.0, 131.3, 139.0, 142.0, 154.4, 167.2, 167.6.

The intermediate 6-[3-(1-adamantyl)-4-(t-butyldimethylsilyloxy)phenyl]-benzaldehyde was prepared as follows:

A mixture of 4-formylphenyl boronic acid (0.301 g, 2.00 mmol), 3-(1-adamantyl)-4-(t-butyldimethylsilyloxy)bromobenzene (0.768 g, 1.82 mmol, prepared in a similar manner as described by Charpentier, B. et al. in J. Med. Chem. 1995, 38, 4993–5006) and potassium carbonate (0.757 g, 5.47 mmol) in 60 mL of toluene:methanol (4:1) and water (2 mL) was degassed with argon for 30 minutes. Tetrakis(triphenylphosphine) palladium(0) (0.422 g, 0.36 mmol) was added and the mixture heated at reflux for 19 hours. The solution was cooled to room temperature, diluted with ethyl acetate and washed successively with water and brine, dried over anhydrous magnesium sulfate, filtered and evaporated. The residue was purified on silica gel (eluent: hexane:EtOAc, 97:3) to give 0.500 g of 4-[3-(1-adamantyl)-4-(t-butyldimethylsilyloxy)phenyl]-benzaldehyde (78%) as a solid. $^1$H NMR (300 MHz; CDCl$_3$): 0.38 (s, 6H), 1.07 (s, 9H), 1.79 (s, 6H), 2.10–2.17 (m, 9H), 6.89 (d, J=8.7 Hz, 1H), 7.34 (dd, J$_1$=8.4 Hz, J$_2$=2.4 Hz, 1H), 7.52 (d, J=2.4 Hz, 1H), 7.71 (d, J=8.1 Hz, 2H), 7.91 (d, J=8.1 Hz, 2H), 10.02 (brs, 1H).

Example 12

6-(3-Phenyl-4-methoxyphenyl)-naphthalen-2-yl-methylene-2,4-thiazolidinedione, which may hereinafter be referred to as "Compound 12"

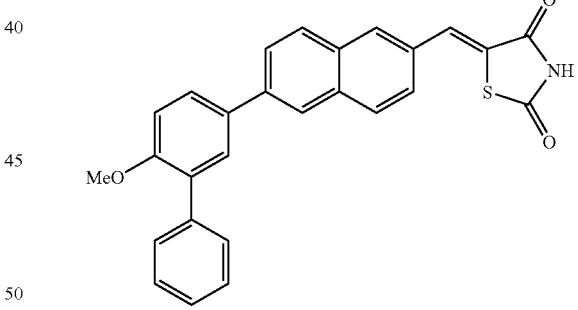

A mixture of toluene (2.5 mL), piperidine (0.003 mL), acetic acid (0.004 mL), 6-[3-phenyl-4-methoxyphenyl]-2-naphthaldehyde (0.124 g, 0.37 mmol) and 2,4-thiazolidinedione (0.043 mg, 0.37 mmol) was heated at reflux for 20 hours under an argon atmosphere. The resulting suspension was filtered and the solid was stirred at room temperature in EtOH. After 3 hours, the solid was filtered and dried under high vacuum to afford 0.023 g (14%) of 6-(3-phenyl-4-methoxyphenyl)-naphthalen-2-yl-methylene-2,4-thiazolidinedione, mp 221–224° C. $^1$H NMR (300 MHz, DMSO-$d_6$): δ 3.85 (s, 3H), 7.28 (d, J=8.4 Hz, 1H), 7.38 (d, J=8.1 Hz, 1H), 7.46 (t, J=7.0 Hz, 2H), 7.60 (d, J=8.4 Hz, 2H), 7.70 (d, J=8.4 Hz, 1H), 7.77 (s, 1H), 7.86 (d, J=8.4 Hz, 1H), 7.94 (s, 1H), 8.00 (d, J=8.4 Hz, 1H), 8.10 (d, J=8.4 Hz, 2H), 8.20 (s, 1H), 8.32 (s, 1H), 12.66 (brs, 1H).

The intermediate 6-(3-phenyl-4-methoxyphenyl)-2-naphthaldehyde was prepared as follows:

a. 6-(3-Phenyl-4-methoxyphenyl)-2-naphthaldehyde.

A mixture of 3-phenyl-4-methoxyphenyl boronic acid (0.465 g, 2.04 mmol), 6-bromo-2-naphthaldehyde (0.400 g, 1.70 mmol) and sodium carbonate (0.541 g, 5.10 mmol) in 10 mL of toluene:ethanol (4:1) and water (1 mL) was degassed with argon for 30 minutes. Tetrakis(triphenylphosphine) palladium(0) (0.059 g, 0.05 mmol) was added and the mixture heated at reflux for 17 hours. The solution was cooled to room temperature, diluted with ethyl acetate and washed successively with water and brine, dried over anhydrous magnesium sulfate, filtered and evaporated. The residue was purified on silica gel (eluent: hexane:EtOAc, 9:1) to give 0.50 g of 6-(3-phenyl-4-methoxyphenyl)-2-naphthaldehyde (86%) as a solid. $^1$H NMR (300 MHz; DMSO-$d_6$, 300 MHz): δ 3.90 (s, 3H), 7.12 (d, J=9.0 Hz, 1H), 7.33–7.50 (m, 3H), 7.55-7.65 (m, 2H), 7.68–7.75 (m, 2H), 7.87 (dd, $J_1$=8.4 Hz, $J_2$=1.8 Hz, 1H), 7.97 (brs, 2H), 8.06 (d, J=9.0 Hz, 1H), 8.09 (d, J=1.0 Hz, 1H), 8.35 (s, 1H), 10.16 (s, 1H).

b. 3-Phenyl-4-methoxyphenyl boronic acid.

To a mixture of 2-phenyl-4-bromoanisole (26.00 g, 0.0988 mol) in THF (240 mL) cooled to −75° C. under an atmosphere of argon was added n-BuLi (68 mL, 1.6 M, 0.109 mol) dropwise maintaining a temperature below −70° C. The resulting suspension was stirred for 30 minutes and triisopropylborate (34.2 mL, 27.87 g, 0.148 mol) was added dropwise. The mixture was warmed to 0° C. over 1 hour and 1.0 N HCl (190 mL) was slowly added and allowed to warm to RT overnight. The mixture was diluted with ether and the layers separated, the aqueous layer was extracted ether (3×) and the organic layers combined. The resulting organic layer was washed with water, brine and dried (Mg$_2$SO$_4$). The mixture was filtered, evaporated and the resulting reddish residue solidified overnight. The solid was collected and washed with hexane and dried under high vacuum to afford 17.29 g of 3-phenyl-4-methoxyphenyl boronic acid (77%). $^1$H NMR (300 MHz; DMSO-$d_6$): δ 3.78 (s, 3H), 7.07 (d, J=8.1 Hz, 1H), 7.28–7.50 (m, 5H), 7.72–7.80 (m, 2H), 7.92 (brs, 2H).

c. 2-Phenyl-4-bromoanisole.

To a solution of 2-phenylanisole (18.27 g, 0.099 mol) in CH$_2$Cl$_2$ (350 mL) was added pyridinium tribromide (34.88 g, 0.109 mol). The resulting mixture was allowed to stir at RT overnight. The mixture was diluted with CH$_2$Cl$_2$ and H$_2$O and the layers were separated, the aqueous layer was extracted with CH$_2$Cl$_2$ (3×). The combined organic layers were washed with H$_2$O, brine and dried with MgSO$_4$. The mixture was filtered and the solvents evaporated to give 2-phenyl-4-bromoanisole as a reddish oil (26.05 g, 100%). $^1$H NMR (300 MHz, CDCl$_3$): δ 3.75 (s, 3H), 6.82 (d, J=8.7 Hz, 1H), 7.28–7.43 (m, 5H), 7.45–7.49 (m, 2H).

d. 2-Phenylanisole.

To a suspension of 2-phenylphenol (20.00 g, 0.117 mol) and K$_2$CO$_3$ (32.48 g, 0.235 mol) in 235 mL of anhydrous acetone was added a neat solution of dimethylsulfate (15.56 g, 0.123 mol) dropwise through a syringe over 5 minute at RT under argon. The resulting thick suspension was stirred over night at RT and 100 mL of EtOH was added. After 1 hour, the mixture was diluted with ether and water. The aqueous layer was extracted with EtOAc. The combined organic layers were washed with water, brine and dried with MgSO$_4$. After filtration, the solvents were removed and dried under high vacuum to give afford 2-phenylanisole (18.85 g, 87% yield). $^1$H NMR (300 MHz, CDCl$_3$): δ 3.80 (s, 3H), 6.95–7.60 (m, 2H), 7.28–7.35 (m, 3H), 7.37–7.43 (m, 2H), 7.50–7.55 (m, 2H).

Example 13

6-(3-Phenyl-4-methoxyphenyl)-naphthalen-2-yl-methylene-2-thioxo-4-thiazolidinone, which may hereinafter be referred to as "Compound 13"

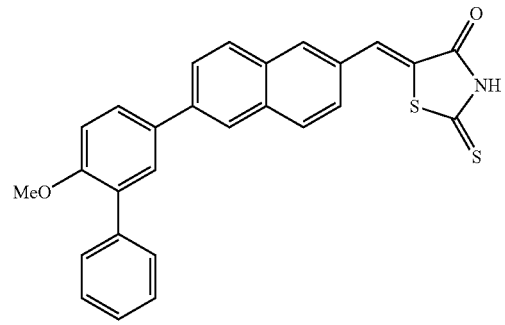

A solution of toluene (2.5 mL), piperidine (0.003 mL), acetic acid (0.004 mL), 6-(3-phenyl-4-methoxyphenyl)-2-naphthaldehyde (0.124 g, 0.37 mmol) and 2-thioxo-4-thiazolidinone (0.049 mg, 0.37 mmol) was heated at reflux for 20.5 hours under an argon atmosphere. The resulting suspension was filtered and the solid was stirred at room temperature in EtOH. After 2 hours, the solid was filtered and dried under high vacuum to afford 0.117 g (70%) of 6-(3-phenyl-4-methoxyphenyl)-naphthalen-2-yl-methylene-2-thioxo4-thiazolidinone, mp 266–269° C. $^1$H NMR (300 MHz, DMSO-$d_6$): δ 3.82 (s, 3H), 7.25 (d, J=8.4 Hz, 1H), 7.35 (d, J=7.2 Hz, 1H), 7.43 (t, J=7.4 Hz, 2H), 7.57 (d, J=7.2 Hz, 2H), 7.67 (d, J=8.7 Hz, 1H), 7.75 (d, J=2.4 Hz, 1H), 7.77 (s, 1H), 7.84 (dd, $J_1$=6.0 Hz, $J_2$=2.4 Hz, 1H), 7.98 (d, J=8.7 Hz, 1H), 8.10 (t, J=9.0 Hz, 2H), 8.19 (s, 1H), 8.30 (s, 1H), 13.96 (brs, 1H).

Example 14

6-[3-(t-butyl)-4-methoxyphenyl]-naphthalen-2-yl-methylene-2,4-thiazolidinedione, which may hereinafter be referred to as "Compound 14"

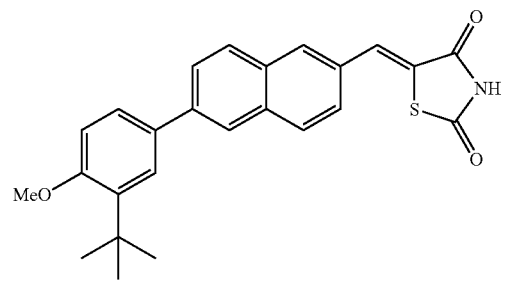

A solution of toluene (2.5 mL), piperidine (0.003 mL), acetic acid (0.003 mL), 6-[3-(t-butyl)-4-methoxyphenyl]-2-naphthaldehyde (0.124 g, 0.31 mmol) and 2,4-thiazolidinedione (0.036 mg, 0.31 mmol) was heated at reflux for 16.5 hours under an argon atmosphere. The resulting suspension was filtered and the solid was stirred at room temperature in EtOH. After 3 hours, the solid was filtered and dried under high vacuum to afford 0.037 g (28%) of 6-[3-(t-butyl)-4-methoxyphenyl]-naphthalen-2-yl-methylene-2,4-thiazolidinedione, mp 274–276° C. $^1$H NMR (300 MHz, DMSO-d$_6$): δ 1.40 (s, 9H), 3.86 (s, 3H), 7.11 (d, J=8.4 Hz, 1H), 7.63 (s, 1H), 7.66 (t, J=8.1 Hz, 2H), 7.88 (d, J=8.4 Hz, 1H), 7.92 (s, 1H), 8.07 (d, J=8.4 Hz, 1H), 8.08 (d, J=8.4 Hz, 1H), 8.17 (brs, 2H), 12.60 (brs, 1H).

The intermediate 6-[3-(t-butyl)-4-methoxyphenyl]-2-naphthaldehyde was prepared as follows:

a. 6-[3-(t-Butyl)-4-methoxyphenyl]-2-naphthaldehyde.

A mixture of 3-(t-butyl)-4-methoxyphenyl boronic acid (0.424 g, 2.04 mmol), 6-bromo-2-naphthaldehyde (0.400 g, 1.70 mmol) and sodium carbonate (0.541 g, 5.10 mmol) in 10 mL of toluene:ethanol (4:1) and water (1 mL) was degassed with argon for 30 minutes. Tetrakis(triphenylphosphine) palladium(0) (0.059 g, 0.05 mmol) was added and the mixture heated at reflux for 17 hours. The solution was cooled to room temperature, diluted with ethyl acetate and washed successively with water and brine, dried over anhydrous magnesium sulfate, filtered and evaporated. The residue was purified on silica gel (eluent: hexane:EtOAc, 9:1) to give 0.50 g of 6-[3-(t-butyl)-4-methoxyphenyl]-2-naphthaldehyde (76%) as a solid. $^1$H NMR (300 MHz; DMSO-d$_6$, 300 MHz): 1.46 (s, 9H), 3.92 (s, 3H), 7.02 (d, J=8.7 Hz, 1H), 7.57 (dd, J$_1$=8.7 Hz, J$_2$=2.4 Hz, 1H), 7.66 (d, J=2.4 Hz, 1H), 7.84 (dd, J$_1$=8.4 Hz, J$_2$=1.8 Hz, 1H), 7.97 (brs, 2H), 8.04 (s, 1H), 8.05 (d, J=8.7 Hz, 1H), 8.35 (s, 1H), 10.16 (s, 1H).

b. 3-(t-Butyl)-4-methoxyphenyl boronic acid.

To a mixture of 2-(t-butyl)-4-bromoanisole (23.07 g, 0.0949 mol) in THF (238 mL) cooled to –75° C. under an atmosphere of argon was added n-BuLi (65.3 mL, 1.6 M, 0.1044 mol) dropwise maintaining a temperature below –70° C. The resulting suspension was stirred for 30 minutes and triisopropylborate (34.2 mL, 27.87 g, 0.148 mol) was added dropwise. The mixture was allowed to warm to RT overnight. The resulting mixture was cooled to 0° C. and 1.0 N HCl (150 mL) was slowly added. After warming to RT the mixture was diluted with ether and the layers separated, the aqueous layer was extracted ether (3×) and the organic layers combined. The resulting organic layer was washed with water, brine and dried (Mg$_2$SO$_4$). The mixture was filtered, evaporated and the resulting yellowish residue solidified overnight. The solid was collected and washed with hexane and dried under high vacuum to afford 12.68 g of 3-(t-butyl)-4-methoxyphenyl boronic acid (64%). $^1$H NMR (300 MHz; DMSO-d$_6$): δ 1.33 (s, 9H), 3.81 (s, 3H), 6.91 (d, J=7.8 Hz, 1H), 7.62–7.79 (m, 2H), 7.78 (brs, 2H).

c. 2-(t-Butyl)-4-bromoanisole.

To a solution of 2-(t-butyl)anisole (16.38 g, 0.0997 mol) in CH$_2$Cl$_2$ (350 mL) was added pyridinium tribromide (35.09 g, 0.110 mol). The resulting mixture was allowed to stir at RT overnight. The mixture was diluted with CH$_2$Cl$_2$ and H$_2$O and the layers were separated, the aqueous layer was extracted with CH$_2$Cl$_2$ (2×). The combined organic layers were washed with H$_2$O, brine and dried with MgSO$_4$. The mixture was filtered and the solvents evaporated to give 2-(t-butyl)-4-bromoanisole as an oil (23.16 g, 95%). $^1$H NMR (300 MHz, CDCl$_3$): δ 1.35 (s, 9H), 3.82 (s, 3H), 6.74 (d, J=8.7 Hz, 1H), 7.28 (dd, J$_1$=8.7 Hz, J$_2$=2.4 Hz, 1H), 7.35 (d, J=2.4 Hz, 1H).

d. 2-(t-Butyl)anisole.

To a suspension of 2-t-butylphenol (20.00 g, 0.133 mol) and K$_2$CO$_3$ (36.80 g, 0.266 mol) in 260 mL of anhydrous acetone was added a neat solution of dimethylsulfate (17.63 g, 0.140 mol) dropwise through a syringe over 5 minute at RT under argon. The resulting thick suspension was stirred over night at RT and 100 mL of EtOH was added. After 1 hour, the mixture was diluted with ether and water. The aqueous layer was extracted with EtOAc. The combined organic layers were washed with water, brine and dried with MgSO$_4$. After filtration, the solvents were removed and dried under high vacuum to give afford 2-t-butylanisole (16.99 g, 78% yield). $^1$H NMR (300 MHz, CDCl$_3$): δ 1.40 (s, 9H), 3.86 (s, 3H), 6.88–6.96 (m, 2H), 7.18–7.26 (m, 1H), 7.31 (dd, J$_1$=7.5 Hz, J$_2$=1.2 Hz, 1H).

Example 15

6-[3-(t-Butyl)-4-methoxyphenyl]-naphthalen-2-yl-methylene-2-thioxo-4-thiazolidinone, which may hereinafter be referred to as "Compound 15"

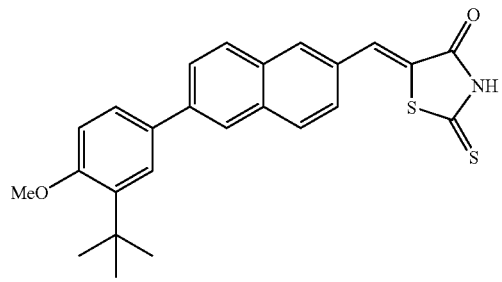

A solution of toluene (2.5 mL), piperidine (0.003 mL), acetic acid (0.003 mL), 6-[3-(t-butyl)-4-methoxyphenyl]-2-naphthaldehyde (0.100 g, 0.31 mmol) and 2-thioxo-4-thiazolidinone (0.041 mg, 0.31 mmol) was heated at reflux for 16.5 hours under an argon atmosphere. The resulting suspension was filtered and the solid was washed with EtOH and H$_2$O. The solid was dried under high vacuum to afford 0.076 g (56%) of 6-[3-(t-butyl)-4-methoxyphenyl]-naphthalen-2-yl-methylene-2-thioxo-4-thiazolidinone, mp 281–284° C. $^1$H NMR (300 MHz, DMSO-d$_6$): δ 1.40 (s, 9H), 3.86 (s, 3H), 7.11 (d, J=8.4 Hz, 1H), 7.61–7.70 (m, 3H), 7.77 (s, 1H), 7.89 (d, J=8.4 Hz, 1H), 8.09 (dd, J$_1$=8.4 Hz, J$_2$=3.0 Hz, 2H), 8.10 (s, 2H), 13.9 (brs, 1H).

Example 16

6-[3-(1-Adamantyl)-4-hydroxyphenyl]-naphthalen-2-yl-methyl-2,4-thiazolidinedione, which may hereinafter be referred to as "Compound 16"

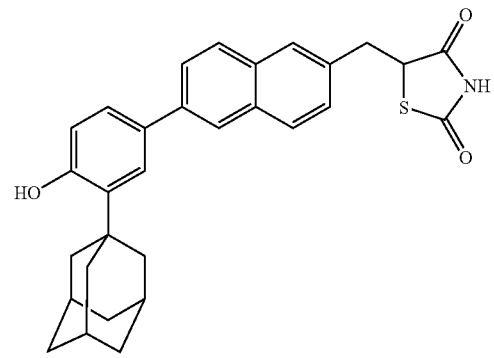

To a yellow suspension of 6-[3-(1-adamantyl)-4-methoxyphenyl]-naphthalen-2-yl-methylene-2,4-thiazolidinedione (0.455 g, 0.92 mmol, see Example 8) in anhydrous CH$_2$Cl$_2$ (15 mL) at −78° C. under an argon atmosphere was added boron triiodide (2.16 g, 5.52 mmol). The cooling bath was removed and the reaction mixture stirred for 6 hours before more boron triiodide (2.16 g, 5.52 mmol) was added. Stirring at room temperature was continued for 44 hours before the reaction mixture was poured onto ice-water, extracted with CH$_2$Cl$_2$, purified on silica gel, (7:3, hexanes: EtOAc as eluant) to afford 0.225 g (52%) of 6-[3-(1-adamantyl)-4-hydroxyphenyl]-naphthalen-2-yl-methyl-2,4-thiazolidinedione, mp 270.5–272.0° C. $^1$H NMR (300 MHz; DMSO-d$_6$): δ 1.75 (s, 6H), 2.06–2.16 (m, 9H), 3.30 (dd, J=9.3 Hz, J=14.1 Hz, 1H), 3.56 (dd, J=4.2 Hz, J=14.1 Hz, 1H), 5.03 (dd, J=4.5 Hz, J=9.3 Hz, 1H), 6.89 (d, J=8.1 Hz, 1H), 7.39–7.46 (m, 3H), 7.73–7.77 (m, 2H), 7.87–7.93 (m, 2H), 8.04 (s, 1H), 9.50 (s, 1H), 12.07 (brs, 1H).

Example 17

5-[3-(1-Adamantyl)-4-methoxyphenyl]-naphthalen-1-yl-methylene-2,4-thiazolidinedione, which may hereinafter be referred to as "Compound 17"

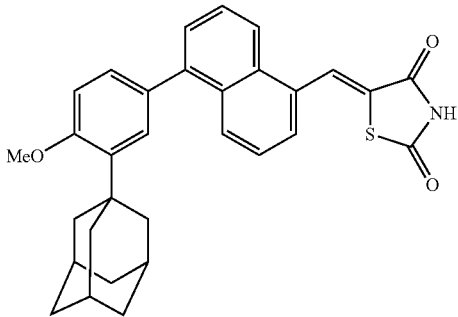

Prepared in a similar manner as described herein using 5-[3-(1-adamantyl)-4-methoxyphenyl]-1-naphthaldehyde (for example, see Example 1); mp 294–295° C., $^1$H NMR (300 MHz; DMSO-d$_6$): δ 1.69 (s, 6H), 1.98–2.05 (m, 9H), 3.86 (s, 3H), 7.09 (d, J=8.1 Hz, 1H), 7.18 (s, 1H), 7.26 (d, J=8.1 Hz, 1H), 7.46–7.66 (m, 4H), 7.92 (d, J=8.7 Hz, 1H), 8.06 (d, J=8.1 Hz, 1H), 8.43 (s, 1H), 12.69 (brs, 1H).

The intermediate 5-[3-(1-adamantyl)-4-methoxyphenyl]-1-naphthaldehyde was prepared in a similar manner as described herein using 3-(1-adamantyl)-4-methoxyphenyl boronic acid (see Example 8) and 5-bromo-1-naphthaldehyde.

5-Bromo-1-naphthaldehyde.

To a flask fitted with a condenser containing 1-naphthaldehyde (10 g, 64.02 mmol) was added a solution of bromine (3.3 mL, 63.83 mmol) in anhydrous chloroform (15 mL). The reaction mixture was heated under reflux for 3.5, allowed to RT and filtered. The filtrate was washed with water, brine and dried (MgSO$_4$). After evaporation the crude product was purified on silica gel (eluant: hexanes:EtOAc, 98:2) to afford 6-bromo-1-naphthaldehyde 5.5 g (27%).

Example 18

5-[3-(1-Adamantyl)-4-methoxyphenyl]-naphthalen-1-yl-methylene-2-thioxo-4-thiazolidinone, which may hereinafter be referred to as "Compound 18"

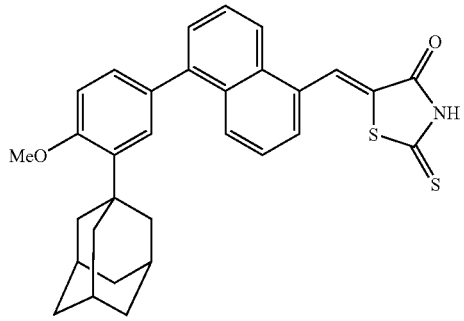

Prepared in a similar manner as described herein using 5-[3-(1-adamantyl)-4-methoxyphenyl]-1-naphthaldehyde (for example, see Example 2); mp 322–324° C., $^1$H NMR (300 MHz; DMSO-d$_6$): δ 1.69 (s, 6H), 1.99–2.05 (m, 9H), 3.86 (s, 3H), 7.11 (d, J=8.4 Hz, 1H), 7.18 (s, 1H), 7.26 (dd, J=6.3 Hz, J=1.5 Hz, 1H), 7.48–7.68 (m, 4H), 7.94 (d, J=8.1 Hz, 1H), 8.11 (d, J=8.4 Hz, 1H), 8.30 (s, 1H), 13.90 (brs, 1H).

Example 19

6-[5-(3,3-Dimethyl-2,3-dihydrobenzofuryl)]-naphthalen-2-yl-methylene-2,4-thiazolidinedione, which may hereinafter be referred to as "Compound 19"

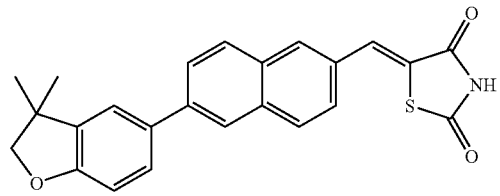

Prepared in a similar manner as described herein using 6-[5-(3,3-Dimethyl-2,3-dihydrobenzofuryl)]-2-naphthaldehyde (for example, see Example 1); mp 243–244° C., $^1$H NMR (300 MHz; DMSO-d$_6$): δ 1.39 (s, 6H), 4.30 (s, 2H), 6.91 (d, J=8.1 Hz, 1H), 7.62 (dd, J$_1$=9.0 Hz, J$_2$=2.0 Hz, 1H), 7.70 (d, J=8.4 Hz, 1H), 7.74 (d, J=1.8 Hz, 1H), 7.91 (s, 1H), 7.93 (s, 1H), 8.09 (d, J=9.0 Hz, 2H), 8.20 (d, J=10.8 Hz, 2H), 12.76 (brs, 1H).

The intermediate 6-[5-(3,3-dimethyl-2,3-dihydrobenzofuryl)]-2-naphthaldehyde was prepared as follows:

a. 6-[5-(3,3-Dimethyl-2,3-dihydrobenzofuryl)]-2-naphthaldehyde.

Prepared in a similar manner as described in Example 1b. using 5-(3,3-dimethyl-2,3-dihydrobenzofur-5-yl boronic acid and 6-bromo-2 naphthaldehyde (see Example 4c), 87% yield, $^1$H NMR (300 MHz; CDCl$_3$): δ 1.44 (s, 6H), 4.34 (s, 2H), 6.93 (d, J=8.4 Hz, 1H), 7.47 (d, J=2.1 Hz, 1H), 7.53 (dd, J$_1$=9.0 Hz, J$_2$=2.1 Hz, 1H), 7.84 (dd, J$_1$=9.0 Hz, J$_2$=2.1 Hz, 1H), 7.97 (s, 2H), 8.06 (d, J=9.0 Hz, 1H), 8.36 (s, 1H), 10.17 (s, 1H).

b. 5-(3,3-Dimethyl-2,3-dihydrobenzofur-5-yl boronic acid.

Prepared using a similar procedure as described herein (see Example 3b.) using 3,3-dimethyl-5-bromo-2,3-dihydrobenzofuran (prepared in a similar manner as described by Spruce, L., et al. in J. Med. Chem. 1987, 30, 1474–1482), 88% yield. δ 1.26 (s, 6H), 4.12 (s, 2H), 6.69 (d, J=8.4 Hz, 1H), 7.56 (dd, $J_1$=8.4 Hz, $J_2$=1.0 Hz, 1H), 7.59 (d, J=1.0 Hz, 1H), 7.77 (s, 2H).

Example 20

6-[5-(3,3-Dimethyl-2,3-dihydrobenzofuryl)]-naphthalen-2-yl-methylene-2-thioxo-4-thiazolidinone, which may hereinafter be referred to as "Compound 20"

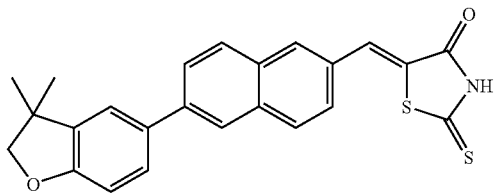

Prepared in a similar manner as described herein using 5-[3-(1-adamantyl)-4-methoxyphenyl]-1-naphthaldehyde (for example, see Example 2).

Example 21

6-[3-(1-Methylcyclohexyl)-4-methoxyphenyl]-naphthalen-2-yl-methylene-2,4-thiazolidinedione, which may hereinafter be referred to as "Compound 21"

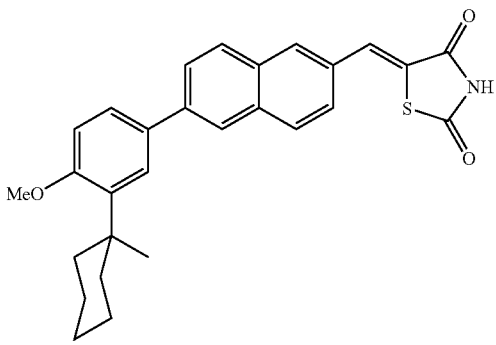

A solution of toluene (2.5 mL), piperidine (0.003 mL), acetic acid (0.003 mL), 6-[3-(1-methylcyclohexyl)-4-methoxyphenyl]-2-naphthaldehyde (0.100 g, 0.28 mmol) and 2,4-thiazolidinedione (0.033 mg, 0.28 mmol) was heated at reflux for 15 hours under an argon atmosphere. The resulting suspension was filtered and the solid was stirred at room temperature in EtOH. After 1 hours, the solid was filtered and dried under high vacuum to afford 0.048 g (37%) of 6-[3-(1-methylcyclohexyl)-4-methoxyphenyl]-naphthalen-2-yl-methylene-2,4-thiazolidinedione, mp 268–271° C. $^1$H NMR (300 MHz, DMSO-$d_6$): δ 1.21–1.61 (m, 9H), 1.69–1.81 (m, 2H), 2.15 (t, J=10.7 Hz, 2H), 3.86 (s, 3H), 7.14 (d, J=8.7 Hz, 1H), 7.65 (s, 1H), 7.69 (brt, J=9.6 Hz, 2H), 7.90 (d, J=9.9 Hz, 1H), 7.94 (s, 1H), 8.10 (d, J=8.7 Hz, 1H), 8.12 (d, J=8.7 Hz, 1H), 8.19 (s, 2H), 12.66 (brs, 1H).

The intermediate 6-[3-(1-methylcyclohexyl)-4-methoxyphenyl]-2-naphthaldehyde was prepared as follows:

a. 6-[3-(1-Methylcyclohexyl)-4-methoxyphenyl]-2-naphthaldehyde.

A mixture of 3-(1-methylcyclohexyl)-4-methoxyphenyl boronic acid (0.315 g, 1.27 mmol), 6-bromo-2-naphthaldehyde (0.250 g, 1.06 mmol) and sodium carbonate (0.337 g, 3.18 mmol) in 10 mL of toluene:ethanol (4:1) and water (1 mL) was degassed with argon for 30 minutes. Tetrakis(triphenylphosphine) palladium(0) (0.035 g, 0.03 mmol) was added and the mixture heated at reflux for 17 hours. The solution was cooled to room temperature, diluted with ethyl acetate and washed successively with water and brine, dried over anhydrous magnesium sulfate, filtered and evaporated. The residue was purified on silica gel (eluent: hexane: EtOAc, 9:1) to give 0.28 g of 6-[3-(1-methylcyclo-hexyl)-4-methoxyphenyl]-2-naphthaldehyde (75%) as a solid. $^1$H NMR (300 MHz; CDCl$_3$, 300 MHz): δ 1.36 (s, 3H), 1.40–1.65 (m, 6H), 1.70–1.85 (m, 2H), 2.10–2.25 (m, 2H), 3.90 (s, 3H), 7.02 (d, J=8.7 Hz, 1H), 7.56 (dd, $J_1$=8.4 H, $J_2$=2.4 Hz, 1H), 7.68 (d, J=2.4 Hz, 1H), 7.84 (dd, $J_1$=8.1 Hz, $J_2$=1.8 Hz, 1H), 7.97 (s, 2H), 8.02–8.07 (m, 2H), 8.35 (s, 1H), 10.16 (s, 1H).

b. 3-(1-Methylcyclohexyl)-4-methoxyphenyl boronic acid.

To a mixture of 2-(1-methylcyclohexyl)-4-bromoanisole (13.66 g, 0.0482 mol) in THF (121 mL) cooled to −75° C. under an atmosphere of argon was added n-BuLi (33.2 mL, 1.6 M, 0.053 mol) dropwise maintaining a temperature below −70° C. The resulting suspension was stirred for 30 minutes and triisopropylborate (34.2 mL, 27.87 g, 0.148 mol) was added dropwise. The mixture was allowed to warm to RT overnight. The resulting mixture was cooled to 0° C. and 1.0 N HCl (150 mL) was slowly added. After warming to RT the mixture was diluted with ether and the layers separated, the aqueous layer was extracted ether (3×) and the organic layers combined. The resulting organic layer was washed with water, brine and dried (Mg$_2$SO$_4$). The mixture was filtered, evaporated and the resulting yellow oil was purified on silica gel (eluent: CH$_2$Cl$_2$:MeOH, 100 to 92:2) to afford 3-(1-methylcyclohexyl)-4-methoxyphenyl boronic acid (7.72 g, 64%) as a white solid. $^1$H NMR (300 MHz; DMSO-$d_6$): δ 120 (s, 3H), 1.40–1.85 (m, 8H), 2.00–2.10 (m, 2H), 3.75 (s, 3H), 6.90 (d, J=8.4 Hz, 1H), 7.60 (d, J=8.4 Hz, 1H), 7.66 (brs, 1H), 7.81 (s, 2H).

c. 2-(1-Methylcyclohexyl)-4-bromoanisole.

To a suspension of 2-(1-methylcyclohexyl)-4-bromophenol (29.68 g, 0.110 mol) and K$_2$CO$_3$ (30.48 g, 0.221 mol) in 200 mL of anhydrous acetone was added a neat solution of dimethylsulfate (13.91 g, 0.110 mol) dropwise through a syringe over 5 minute at RT under argon. The resulting thick suspension was stirred over night at RT and 100 mL of EtOH was added. After 1 hour, the mixture was diluted with ether and water. The aqueous layer was extracted with EtOAc. The combined organic layers were washed with water, brine and dried with MgSO$_4$. After filtration, the solvents were removed and the residue distilled under reduced vacuum, 130–132° C. (0.7 mm/Hg). The impure fractions were combined and further purified on silica gel (hexane) to give a total amount of 2-(1-methylcyclohexyl)-4-bromoanisole as an oil (13.66 g, 44%). $^1$H NMR (300 MHz, CDCl$_3$): δ 1.26 (s, 3H), 1.30–1.70 (m, 8H), 1.90–2.10 (m, 2H), 3.79 (s, 3H), 6.74 (d, J=8.4 Hz, 1H), 7.26 (dd, $J_1$=8.4 Hz, $J_2$=2.4 Hz, 1H), 7.36 (d, J=2.4 Hz, 1H).

d. 2-(1-Methylcyclohexyl)-4-bromophenol.

A mixture of 1-methylcyclohexanol (100.00 g, 0.876 mol) and 4-bromophenol (101.01 g, 0.584 mol) in $CH_2Cl_2$ (1.0 L) and $H_2SO_4$ (44 mL) was heated to reflux for 4 days. The mixture was cooled to RT. The reaction was poured in a separatory funnel and washed with water, 0.5 N $NaHCO_3$ (till neutralized), brine and dried ($MgSO_4$). The mixture was filtered, evaporated and the residue was purified on silica gel (eluant: hexane: $CH_2Cl_2$, 4:1) to give a total amount of 2-(1-methylcyclohexyl)-4-bromoanisole as an oil (29.70 g, 13%). $^1H$ NMR (300 MHz, $CDCl_3$): δ 1.30 (s, 3H), 1.30–1.70 (m, 8 H), 2.00–2.15 (m, 2H), 4.87 (s, 1H), 6.54 (d, J=8.4 Hz, 1H), 7.15 (dd, $J_1$=8.4 Hz, $J_2$=2.4 Hz, 1H), 7.36 (d, J=2.4 Hz, 1H).

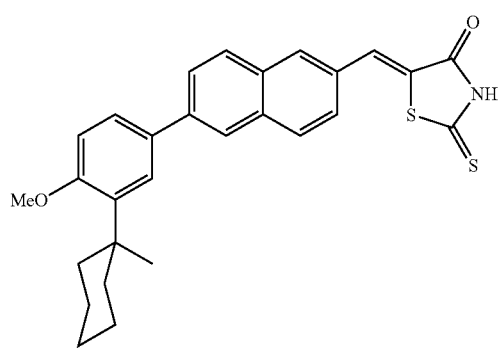

Example 22

6-[3-(1-Methylcyclohexyl)-4-methoxyphenyl]-naphthalen-2-yl-methylene-2-thioxo-4-thiazolidinone, which may hereinafter be referred to as "Compound 22"

A solution of toluene (2.5 mL), piperidine (0.002 mL), acetic acid (0.002 mL). 6-[3-(1-methylcyclohexyl)-4-methoxphenyl]-2-naphthaldehyde (0.075 g, 0.21 mmol). and 2-thioxo-4-thiazolidinone (0.028 mg, 0.21 mmol) was heated at reflux for 16 hours under an argon atmosphere. The mixture was diluted with toluene (5 mL) and after 10 minutes and mixture was filtered hot. The resulting solid was stirred in EtOH for 1 hour, filtered and the solid dried under high vacuum to afford 0.039 g (39%) of 6-[3-(1-methylcyclohexyl)-4-methoxyphenyl]-naphthalen-2-yl-methylene-2-tioxo-4-thiazolidinone, mp 288–291° C. $^1H$ NMR (300 MHz, DMSO-$d_6$): δ 132 (s, 3H), 1.40–1.65 (m, 6H), 1.69–1.81 (m, 2H), 2.15 (t, J=9.9 Hz, 2H), 3.86 (s, 3H), 7.14 (d, J=9.0 Hz, 1H), 7.64–7.72 (m, 3H), 7.79 (s, 1H), 7.91 (dd, $J_1$=8.7 Hz, $J_2$=1.2 Hz, 1H), 8.12 (d, J=8.7 Hz, 1H), 8.13 (d, J=8.7 Hz, 1H), 8.20 (brs, 2H), 13.91 (brs, 1H).

Example 23

5-[6-(3-[1-Adamantyl]-4-methoxyphenyl)-naphthalen-2-yl]-2,4-thiazolidinedione, which may hereinafter be referred to as "Compound 23"

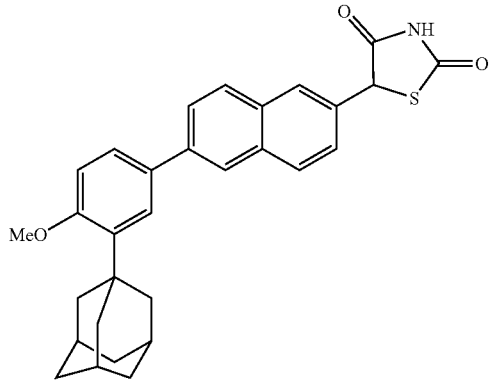

To a suspension of the 2-[6-(3-[1-adamantyl]-4-methoxyphenyl)-2-naphthyl]-2-chloro-acetonitrile (0.74 mmol) in anhydrous EtOH (10 mL) was added thiourea (0.082 mg, 1.08 mmol) under an argon atmosphere. The reaction mixture was heated under reflux for 3 hours before it was allowed to cool and 3N HCl (10 mL) added. It was heated under reflux for 18 hours before it was allowed to cool, poured into water, extracted with EtOAc, washed with water, brine and purified on silica gel (eluant: hexanes: EtOAc, 7:3) to afford 5-[6-(3-[1-adamantyl]-4-methoxyphenyl)-naphthalen-2-yl]-2,4-thiazolidinedione 0.285 mg (80%), mp 205–207° C. $^1H$ NMR (300 MHz; DMSO-$d_6$): δ 1.79 (s, 6H), 2.04–2.11 (m, 9H), 3.82 (s, 3H), 5.97 (s, 1H), 7.0 (d, J=8.1 Hz, 1H), 7.49–7.61 (m, 3H), 7.82 (d, J=8.4 Hz, 1H), 7.97–8.02 (m, 3H), 8.14 (s, 1H), 12.37 (brs, 1H); $^{13}C$ NMR (75 MHz; DMSO-$d_6$): 28.4, 36.6, 54.6, 55.3, 112.5, 123.9, 124.7, 125.4, 125.6, 125.7, 127.6, 128.3, 129.0, 131.3, 131.5, 132.2, 133.0, 137.8, 138.5, 158.2, 171.3, 174.7.

The intermediate 2-[6-(3-[1-adamantyl]-4-methoxyphenyl)-2-naphthyl]-2-chloro-acetonitrile was prepared as follows:

a. 2-[6-(3-[1-Adamantyl]-4-methoxyphenyl)-2-naphthyl]-2-hydroxy-acetonitrile.

To a suspension of 6-[3-(1-adamantyl)-4-methoxyphenyl]-2-naphthaldehyde (0.4 g, 1.01 mmol) and $ZnI_2$ (0.07 mg, 0.02 mmol) in anhydrous $CH_2Cl_2$ (5 mL) stirring at 0–5° C. under an argon atmosphere was added trimethylsilylcyanide (0.16 mL, 1.18 mmol). The reaction mixture was stirred for 1.0 hour at 0–5° C. before it was allowed to warm to room temperature and stirred for 26 hours. It was poured into water, extracted with $CH_2Cl_2$. After removal of the solvent, the residue was dissolved in 1,3-dioxolane (10 mL) and 2N HCl added. After stirring at room temperature for 1.5 hours, it was poured into water, extracted with EtOAc, washed with water, brine and recrystallized from hexane/$CH_2Cl_2$ to afford 2-[6-(3-[1-adamantyl]-4-methoxyphenyl)-2-naphthyl]-2-hydroxy-acetonitrile as an orange powder 0.340 mg (80%). $^1H$ NMR (300 MHz; $CDCl_3$): δ 1.80 (s, 6H), 2.10–2.18 (m, 9H), 2.86 (s, 1H), 3.90 (s, 3H), 5.71 (s, 1H), 6.99 (d, J=8.4 Hz, 1H), 7.51–7.61 (m, 3H), 7.78–7.82 (m, 1H), 7.90–8.02 (m, 4H).

b. 2-[6-(3-[1-Adamantyl]-4-methoxyphenyl)-2-naphthyl]-2-chloro-acetonitrile.

To a solution of 2-[6-(3-[1-adamantyl]-4-methoxyphenyl)-2-naphthyl]-2-hydroxy-acetonitrile, (0.314 mg, 0.74 mmol) in anhydrous chloroform (10 mL) were added $SOCl_2$ (0.17 mL, 2.23 mmol) and DMF (3 drops). The reaction mixture was heated under reflux for 40 minutes before it was allowed to cool down, washed with water, saturated $NaHCO_3$, brine to give 2-[6-(3-[1-adamantyl]-4-methoxyphenyl)-2-naphthyl]-2-chloro-acetonitrile that was used without further purification.

Example 24

5-[6-(3-[1-Adamantyl]-4-hydroxyphenyl)-naphthalen-2-yl]-2,4-thiazolidinedione, which may hereinafter be referred to as "Compound 24"

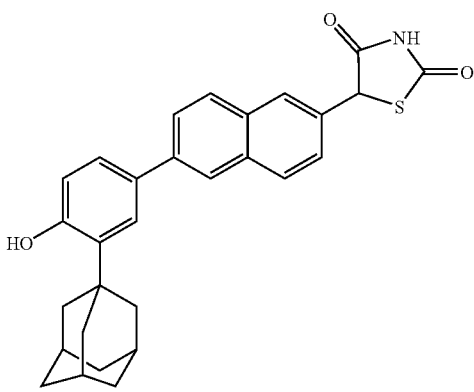

To a solution of 5-[6-(3-[1-adamantyl]-4-methoxyphenyl)-naphthalen-2-yl]-2,4-thiazolidinedione (0.130 g, 0.27 mmol) in 10 mL of anhydrous $CH_2Cl_2$ cooled to −78° C. under argon was added borontribromide (0.31 mL, 3.23 mmol). The cooling bath was removed and the reaction mixture was stirred for 18 hours at RT. The resulting mixture was carefully poured onto ice and extracted with $CH_2Cl_2$ (2×50 mL). The combined organics were washed with water, brine and dried over magnesium sulfate. The mixture was filtered, evaporated and the residue was purified on silica gel (eluent: hexane:EtOAc, 3:2) to give 5-[6-(3-[1-adamantyl]-4-hydroxyphenyl)-naphthalen-2-yl]-2,4-thiazolidinedione as a solid (0.090 g, 72% yield); mp 312–314.5° C., $^1$H NMR (300 MHz; DMSO-$d_6$): δ 1.74 (s, 6H), 2.05–2.15 (m, 9H), 5.97 (s, 3H), 6.88 (d, J=8.1 Hz, 1H), 7.43–7.51 (m, 3H), 7.81 (dd, $J_1$=8.7 Hz, $J_2$=1.8 Hz 1H), 7.94–8.02 (m, 3H), 8.10 (s, 1H), 9.52 (s, 1H), 12.35 (brs, 1H).

Example 25

6-[3-(3-Pyridyl)-4,5-methylenedioxyphenyl]-naphthalen-2-yl-methylene-2,4-thiazolidinedione, which may hereinafter be referred to as "Compound 25"

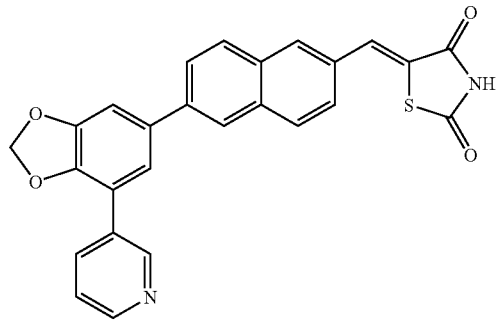

A solution of toluene (8 mL), piperidine (0.008 mL), acetic acid (0.009 mL) and 6-[3-(3-pyridyl)-4,5-methylenedioxyphenyl]-2-naphthaldehyde (0.304 g, 0.86 mmol) and 2,4-thiazolidinedione (101 mg, 0.86 mmol) was heated at reflux for 16 hours under an argon atmosphere. The resulting suspension was filtered and the solid was stirred at room temperature in EtOH. After 1 hours, the solid was filtered and dried under high vacuum to afford 78.0 mg of 6-[3-(3-pyridyl)-4,5-methylenedioxyphenyl]-naphthalen-2-yl-methylene-2,4-thiazolidinedione, mp 298–300° C. $^1$H NMR (300 MHz, DMSO-$d_6$): δ 6.16 (s, 2H), 7.10–7.28 (m, 4H), 7.51 (dt, $J_1$=8.0 Hz, $J_2$=1.5 Hz, 1H), 7.66 (dd, $J_1$=8.4 Hz, $J_2$=1.8 Hz, 1H), 7.75–7.85 (m, 2H), 7.90 (s, 1H), 7.93 (d, J=8.7 Hz, 1H), 8.11 (s, 1H), 8.25 (d, J=1.5 Hz, 1H), 8.34 (dd, $J_1$=4.8 Hz, $J_2$=1.4 Hz, 1H), 12.69 (brs, 1H).

The intermediate 6-[3-(3-pyridyl)-4,5-methylenedioxyphenyl]-2-naphthaldehyde was prepared as follows:

a. 6-[3-(3-Pyridyl)-4,5-methylenedioxyphenyl]-2-naphthaldehyde.

To a degassed mixture of 3-pyridiylboronic acid (0.83 g, 6.75 mmol), 6-[3-bromo-4,5-methylenedioxyphenyl]-2-naphthaldehyde (2.00 g, 5.63 mmol) and sodium carbonate (1.790 g, 16.89 mmol) in 80 mL of toluene:ethanol (4:1) and water (8 mL) was added tetrakis(triphenylphosphine) palladium(0) (0.324 g, 0.28 mmol). The resulting mixture was heated at reflux for 17 hours. The solution was cooled to room temperature, diluted with ethyl acetate and washed successively with water and brine, dried over anhydrous magnesium sulfate, filtered and evaporated. The residue was purified on silica gel (eluent: hexane:EtOAc, 1:1) to give 1.36 g of 6-[3-(3-Pyridyl)-4,5-methylene-dioxyphenyl]-2-naphthaldehyde (68%) as a solid. $^1$H NMR (300 MHz; $CDCl_3$): 6.10 (s, 2H), 6.96 (s, 1H), 7.04 (s, 1H), 7.07 (dd, $J_1$=4.5 Hz, $J_2$=1.0 Hz, 1H), 7.18 (dd, $J_1$=8.7 Hz, $J_2$=1.8 Hz, 1H), 7.36 (ddd, $J_1$=8.0 Hz, $J_2$=2 Hz, $J_3$=1.5 Hz, 1H), 7.71 (d, J=1.0 Hz, 1H), 7.79 (t, J=9.3 Hz, 2H), 7.93 (dd, $J_1$=8.4 Hz, $J_2$=1.8 Hz, 1H), 8.26 (s, 1H), 8.30–8.45 (m, 2H), 10.13 (s, 1H).

b. 6-[3-Bromo-4,5-methylenedioxyphenyl]-2-naphthaldehyde.

To a solution of 6-[3-bromo-4,5-methylenedioxyphenyl]-naphthalen-2-yl-methyl alcohol (16.80, 47.03 mmol) in $CH_2Cl_2$ (460 mL) was added PCC (11.15 g, 51.73 mmol) all at once. The mixture was stirred at room temperature for 1 hour and 200 mL of anhydrous ether was added. The resulting dark suspension was passed through a short column of silica and washed with ether. The solvents were evaporated and the solid was dried under high vacuum to give 15.32 g (91.7%) of 6-[3-bromo-4,5-methylene-dioxyphenyl]-2-naphthaldehyde. $^1$H NMR (300 MHz; CDCl$_3$): 6.07 (s, 2H), 6.91 (s, 1H), 7.17 (s, 1H), 7.64 (dd, J$_1$=8.4 Hz, J$_2$=1.8 Hz, 1H), 7.87 (s, 1H), 7.90–8.10 (m 3H), 8.39 (s, 1H), 10.19 (s, 1H).

c. 6-[3-Bromo-4,5-methylenedioxyphenyl]-naphthalen-2-yl-methyl alcohol.

To a solution of ethyl 6-[3-bromo-4,5-methylenedioxyphenyl]-2-naphthoate (18.32 g, 45.90 mmol) in 308 mL toluene at −78° C. under an atmosphere of argon was added DIBAL (92 mL, 1.5 M in toluene, 137.7 mmol) dropwise. After 1 hour the reaction mixture was quenched with ethyl acetate and the resulting mixture was allowed to warm to RT. The mixture was diluted with ethyl acetate and washed with 5% NH$_4$Cl, water and brine. The organics were dried with magnesium sulfate, filtered and evaporated. The residue was passed through a short silica gel column (eluent: CH$_2$Cl$_2$) to give 16.40 g of 6-[3-bromo-4,5-methylenedioxyphenyl]-naphthalen-2-yl-methyl alcohol (100%). $^1$H NMR (300 MHz; CDCl$_3$): δ 4.85 (s, 2H), 6.01 (s, 2H), 6.88 (s, 1H), 7.13 (s, 1H), 7.47 (dd, J$_1$=4.0 Hz, J$_2$=1.8 Hz, 1H), 7.50 (dd, J$_1$=4.0 Hz, J$_2$=1.8 Hz, 1H), 7.76–7.85 (m, 4H).

d. Ethyl 6-[3-bromo-4,5-methylenedioxyphenyl]-2-naphthoate.

To a solution of ethyl 6-[4,5-methylenedioxyphenyl]-2-naphthoate (19.61 g, 56.50 mmol, prepared in a similar manner via a Suzuki coupling of 3,4-methylenedioxyphenyl boronic acid and 6-carboethoxynaphthyl-2-trifluoromethanesulfonate, 84% yield) in CH$_2$Cl$_2$ (900 mL) was pyridinium tribromide (19.91 g, 62.26 mmol) at RT. The resulting mixture was allowed to stir overnight. After 24 hours, additional amount of pyridinium tribromide (9.05 g, 28.3 mmol) was added and the mixture stirred overnight. The mixture was washed with H$_2$O, brine and dried over magnesium sulfate. After filtering, the solvent was removed and purified on silica gel (CH$_2$Cl$_2$) to give ethyl 6-[3-bromo-4,5-methylenedioxyphenyl]-2-naphthoate (100%) as a white solid. $^1$H NMR (300 MHz; CDCl$_3$): δ 1.47 (t, J=7.2 Hz, 3H), 4.46 (q, J=7.2 Hz, 2H), 6.05 (s, 2H), 6.90 (s, 1H), 7.15 (s, 1H), 7.57 (dd, J$_1$=9.0 Hz, J$_2$=1.5 Hz, 1H), 7.84 (s, 1H), 7.90 (d, J=9.0 Hz, 1H), 7.98 (d, J=9.0 Hz, 1H), 8.64 (s, 1H).

Example 26

6-[3-(4-Pyridyl)-4,5-methylenedioxyphenyl]-naphthalen-2-yl-methylene-2,4-thiazolidinedione, which may hereinafter be referred to as "Compound 26"

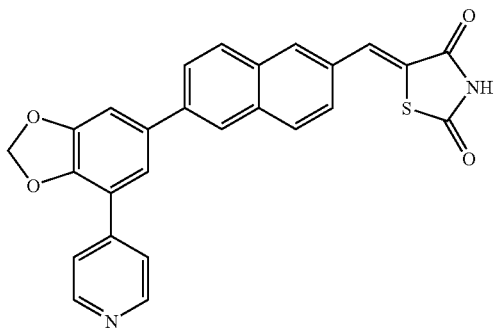

Prepared in a similar manner as described in Example 25 utilizing 6-[3-(4-pyridyl)-4,5-methylenedioxyphenyl]-2-naphthaldehyde and 2,4-thiazolidinedione, mp 304–307° C., $^1$H NMR (300 MHz, DMSO-d$_6$): δ 6.21 (s, 2H), 7.20 (dd, J$_1$=8.4 Hz, J$_2$=1.5 Hz, 1H), 7.25 (d, J=3.3 Hz, 2H), 7.47 (d, J=3.3 Hz, 2H), 7.69 (dd, J$_1$=8.7 Hz, J$_2$=1.8 Hz, 1H), 7.80–8.00 (m, 4H), 8.14(s, 1H), 8.56 (d, J=6.6 Hz, 2H), 12.69 (brs, 1H).

The intermediate 6-[3-(4-pyridyl)-4,5-methylenedioxyphenyl]-2-naphthaldehyde was prepared as follows was prepared in a similar manner as described in Example 25(a).

Example 27

6-[3-(1-Adamantyl)-3,4-methylenedioxyphenyl]-naphthalen-2-yl-methyl-2,4-thiazolidinedione, which may hereinafter be referred to as "Compound 27"

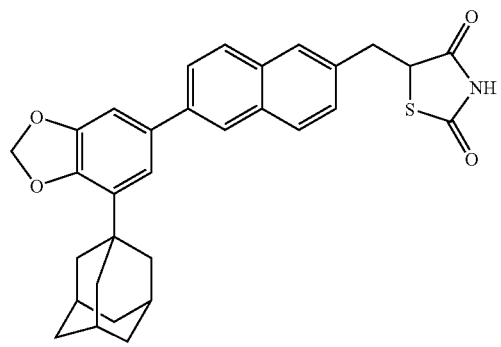

To a solution of 6-[3-(1-adamantyl)-4,5-methylenedioxyphenyl]-naphthalen-2-yl-methylene-2,4-thiazolidinedione (0.377 g, 0.72 mmol) in 3.0 mL THF and 0.58 mL pyridine was added 0.79 mL of LiBH$_4$ (1.58 mmol). The resulting orange solution was heated to reflux until starting material was consumed. The mixture was cooled to 0° C., acidified with 1 N HCl and extracted with EtOAc (3×). The organics were combined and washed with water, brine and dried (MgSO$_4$). After filtering, the mixture was evaporated and the crude product was purified on silica gel, (1:1, hexane:EtOAc) to give a yellow solid, 0.111 g (29% yield); mp 191–195° C., $^1$H NMR (300 MHz, CDCl$_3$): δ 1.80 (s, 6H), 2.11 (s, 9H), 3.32 (dd, J$_1$=14.1 Hz, J$_2$=9.9 Hz, 1H), 3.72 (dd, J$_1$=13.8 Hz, J$_2$=3.6 Hz, 1H), 4.65 (dd, J$_1$=9.3 Hz, J$_2$=4.5 Hz, 1H), 6.00 (s, 2H), 7.08 (dd, J$_1$=5.4 Hz, J$_2$=1.8 Hz, 2H), 7.36 (dd, J$_1$=8.7 Hz, J$_2$=1.8 Hz, 1H), 7.65–7.75 (m, 2H), 7.86 (dd, J$_1$=8.7 Hz, J$_2$=3.3 Hz, 2H), 7.93 (brs, 2H).

Example 28

6-[3-(4-Pyridyl)-4,5-methylenedioxyphenyl]-naphthalen-2-yl-methyl-2,4-thiazolidinedione, which may hereinafter be referred to as "Compound 28"

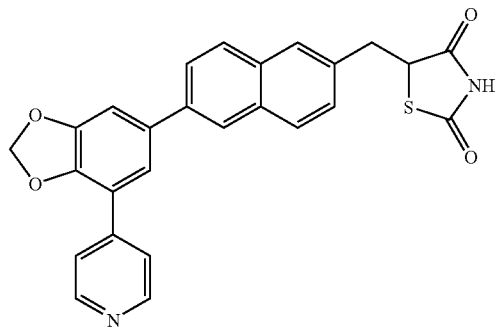

Prepared in a similar manner as described in Example 27 utilizing 6-[3-(4-pyridyl)-4,5-methylenedioxyphenyl]-naphthalen-2-yl-methylene-2,4-thiazolidinedione.

Example 29

6-[3-(1-Adamantyl)-4-hydroxyphenyl]-naphthalen-2-yl-methylene-2,4-thiazolidinedione, which may hereinafter be referred to as "Compound 29"

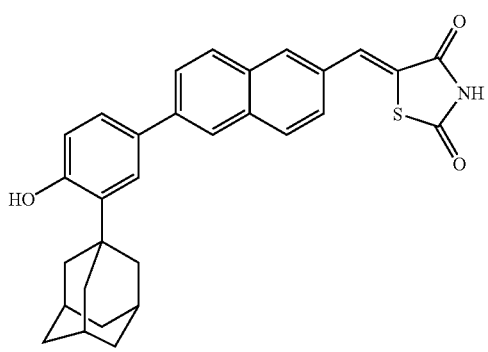

Prepared in a similar manner as described in Example 24 utilizing 6-[3-(1-adamantyl)-4-methoxyphenyl]-naphthalen-2-yl-methylene-2,4-thiazolidinedione. mp 299–302° C., [M–H]⁻=480, expected 480, ¹H NMR (300 MHz, DMSO-$d_6$): δ 1.76 (brs, 6H), [2.07 (s), 2.17 (s), 9 H], 6.91 (d, J=8.0 Hz, 1H), 7.45–7.55 (m, 2H), 7.67 (d, J=8.0 Hz, 1H), 7.86 (d, J=7.0 Hz, 1H), 7.93 (d, J=2.0 Hz, 1H), 8.08 (m, 4H), 9.59 (d, J=3.0 Hz, 1H), 12.63 (brs 1H).

Example 30

6-[3-(t-butyl)-4-hydroxyphenyl]-naphthalen-2-yl-methylene-2,4-thiazolidinedione, which may hereinafter be referred to as "Compound 30"

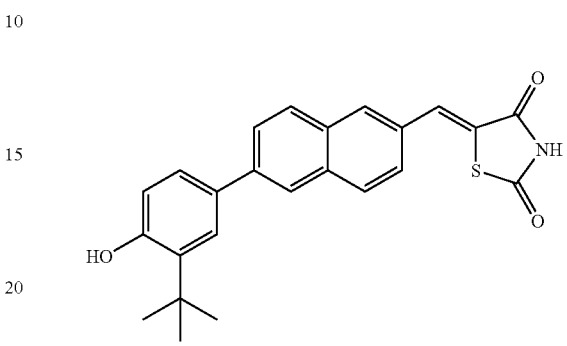

Prepared in a similar manner as described in Example 24 utilizing 6-[3-(t-butyl)-4-methoxyphenyl]-naphthalen-2-yl-methylene-2,4-thiazolidinedione. mp 276-278° C., ¹H NMR (300 MHz, DMSO-$d_6$): δ 1.42 (s, 9H), 6.92 (d, J=9.0 Hz, 1H), 7.49 (d, J=2.0 Hz, 1H), 7.57 (d, J=2.0 Hz, 1H), 7.67 (dd, $J_1$=9.0 Hz, $J_2$=2.0 Hz, 1H), 7.86 (dd, $J_1$=8.4 Hz, $J_2$=2.0 Hz, 1H), 7.92 (s, 1H), 8.05 (d, J=8.4 Hz, 1H), 8.07 (d, J=8.4 Hz, 1H), 9.64 (s, 1H), 12.63 (brs, 1H).

Example 31

6-[3-(3-Pyridyl)-4,5-methylenedioxyphenyl]-naphthalen-2-yl-methyl-2,4-thiazolidinedione, which may hereinafter be referred to as "Compound 31"

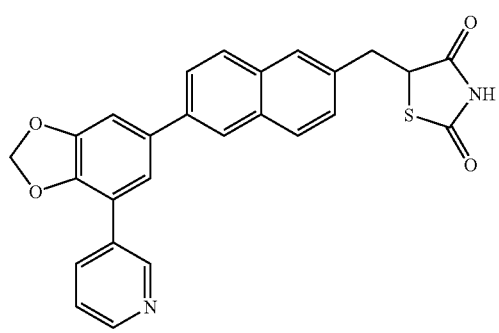

Prepared in a similar manner as described in Example 27 utilizing 6-[3-(3pyridyl)-4,5-methylenedioxyphenly]-naphthalen-2-yl-methylene-2,4-thiazolidinedione.

Example 32

6-[3-(1-Adamantyl)-3,4-methylenedioxyphenyl]-naphthalen-2-yl-methyl-2-thioxo-4-thiazolidinone, which may hereinafter be referred to as "Compound 32"

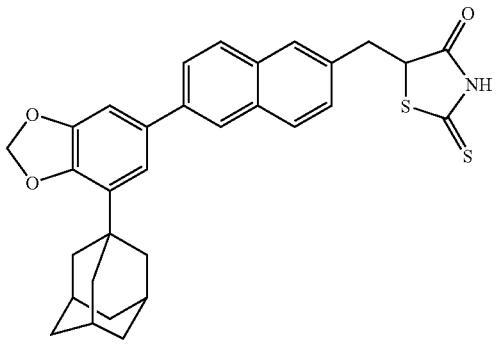

Prepared in a similar manner as described in Example 27 utilizing 6-[3-(1-adamantyl)-4,5-methylenedioxyphenyl]-naphthalen-2-yl-methylene-2-thioxo-4-thiazolidinedione (this compounds was prepared in a similar manner as described herein). mp 151–155° C., $^1$H NMR (300 MHz, CDCl$_3$): δ 1.80 (s, 6H), 2.11 (s, 9H), 3.34 (dd, J$_1$=14.1 Hz, J$_2$=9.9 Hz, 1H), 3.72 (dd, J$_1$=14.1 Hz, J$_2$=3.6 Hz, 1H), 4.72 (dd, J$_1$=9.9 Hz, J$_2$=3.9 Hz, 1H), 6.00 (s, 2H), 7.08 (dd, J$_1$=5.4 Hz, J$_2$=1.8 Hz, 2H), 7.35 (dd, J$_1$=8.7 Hz, J$_2$=1.8 Hz, 1H), 7.65–7.75 (m, 2H), 7.84 (d, J=8.7 Hz, 1H), 7.86 (d, J=8.4 Hz, 1H), 7.93 (s, 1H); 8.88 (brs, 1H).

Example 33

6-[3-(1-Adamantyl)-4-hydroxy-phenyl]-pyridin-3-ylmethylene]-thiazolidine-2,4-dione, which may hereinafter be referred to as "Compound 33"

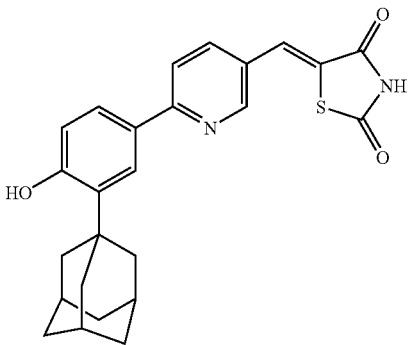

A solution of toluene (425 mL), piperidine (0.545 mL, 0.10 eq), acetic acid (0.316 mL, 0.1 eq), 6-[3-(1-adamantyl)-4-hydroxy-phenyl]-pyridin-3-carboxaldehyde (18.375 g, 0.0551 mol) and 2,4-thiazolidinedione (6.455 g, 0.0551mol) was heated at reflux overnight under an argon atmosphere. The reaction mixture was filtered hot and the resulting solid was suspended in EtOH (1 L) for 1.5 hours. The yellow solid was collected via filtration and dried under high vacuum to afford 15.559 g (65%) of 6-[3-(1-adamantyl)-4-hydroxy-phenyl]-pyridin-3-ylmethylene]-thiazolidine-2,4-dione, mp 315–318° C. $^1$H NMR (300 MHz; DMSO-d$_6$): 1.72 (s, 6H); 2.04 (s, 3H); 2.11 (s, 6H); 6.86 (d, J=8.7 Hz, 1H); 7.75–8.10 (m, 5H); 8.81 (d, J=1.8 Hz, 1H); 9.84 (s, 1H); 12.66 (brs, 1H).

The intermediate 6-[3-(1-adamantyl)-4-hydroxy-phenyl]-pyridin-3-carboxaldehyde was prepared as follows:

a. 6-[3-(1-Adamantyl)-4-hydroxy-phenyl]-pyridin-3-carboxaldehyde.

To a solution of 6-[3-(1-adamantyl)-4-t-butyldimethylsilanyloxyphenyl]-pyridin-3-carboxaldehyde (24.673 g, 0.0511 mol) in 330 mL of dry THF cooled to 0° C. was added dropwise 60.6 mL of 1.0 M solution of tetrabutylammonium fluoride in THF. After 10 minutes from the completion of the addition, the dark red solution was partitioned between EtOAc and 1 M HCl. The mixture was separated the organics were washed with brine, dried (MgSO$_4$), filtered and evaporated. The resulting solid was dried under high vacuum to give 6-[3-(1-adamantyl)-4-hydroxy-phenyl]-pyridin-3-carboxaldehyde (100%). $^1$H NMR (300 MHz; CDCl$_3$): δ 1.79 (brs, 6H), [2.09 (brs), 2.20 (s), 9 H], 6.47 (brs, 1H), 6.86 (d, J=8.1 Hz, 1H), 7.76 (dd, J$_1$=8.1, J$_2$=2.4 Hz, 1H), 8.01 (d, J=2.4 Hz, 1H), 8.17 (dd, J$_1$=8.1, J$_2$=2.4 Hz, 1H), 9.06 (d, J=2.4 Hz, 1H), 10.09 (s, 1H).

b. 6-[3-(1-Adamantyl)-4-t-butyldimethylsilanyloxyphenyl]-pyridin-3-carboxaldehyde.

A mixture of 6-bromopyridine-3-carboxaldehyde (15.00 g, 0.0806 mol), 3-adamantan-1-yl-4-t-butyldimethylsilanyloxyphenyl boronic acid (37.39 g, 0.09677 mmol) and sodium carbonate (1.719 g, 12.44 mmol) in 750 mL of toluene:EtOH (4:1) and 75 mL of water was degassed with argon for 30 minutes. Tetrakis(triphenyl-phosphine)palladium(0) (2.335 g, 0.00202 mmol, 0.025 eq) was added and the mixture heated at reflux under argon overnight. The solution was cooled to room temperature, diluted with ethyl acetate and washed successively with water and brine, dried over anhydrous magnesium sulfate, filtered and evaporated. The residue was purified on silica gel (eluent: hexane:ethyl acetate, 9:1) to give 24.689 g of 6-[3-(1-adamantyl)-4-t-butyldimethylsilanyloxyphenyl]-pyridin-3-carboxaldehyde (68%). $^1$H NMR (300 MHz; CDCl$_3$): δ 0.39 (s, 6H), 1.06 (s, 9H), 1.79 (brs, 6H), [2.11 (brs), 2.19 (s), 9 H], 6.91 (d, J=8.4 Hz, 1H), 7.75–7.85 (m, 2H), 8.04 (d, J=2.1 Hz, 1H), 8.16 (dd, J$_1$=8.4, J$_2$=2.1 Hz, 1H), 9.06(d, J=2.1 Hz, 1H), 10.09 (s, 1H).

c. 3-Adamantan-1-yl-4-t-butyldimethylsilanyloxyphenyl boronic acid.

To a solution of n-BuLi (142.4 mL, 2.5 M, 0.356 mmol, 1.5 eq) in THF (1.1 L) cooled to –78° C. under an atmosphere of argon was added a solution of 3-adamantan-1-yl-4-t-butyldimethylsilanyloxy bromobenzene (100.0 g, 0.237 mol) in THF (200 mL) dropwise over 30 minutes. After stirring for 1 hour at –78° C., triisopropylborate (133.9 g, 0.712 mol, 164 mL, 3.0 eq) was added dropwise over 30 minutes and the cold bath was removed. The mixture was stirred for 45 minutes (internal temperature <0° C.), 200 mL of saturated NH$_4$Cl was added and the mixture was stirred overnight. The mixture was diluted with ethyl acetate and the layers separated, the aqueous layer was extracted once with ethyl acetate and the two organic layers combined. The resulting organic layer was washed with water, brine and dried (Mg$_2$SO$_4$). The mixture was filtered, evaporated and the residue stirred in hexane. The resulting white suspension was filtered and the white solid dried under high vacuum to afford 54.7 g of 3-adamantan-1-yl-4-t-Butyl-dimethyl-silanyloxy-phenylboronic acid (59%). Additional material can be obtained from the hexane filtrate using silica gel chromatography. $^1$H NMR (300 MHz; CDCl$_3$): δ 0.40 (s, 6H), 1.07 (s, 9H), 1.82 (brs, 6H), 2.11 (brs, 3H). 2.22 (s, 6H), 6.91 (d, J=7.8 Hz, 1H), 7.92 (dd, J$_1$=7.8 Hz, J$_2$=1.5 Hz, 1H), 8.16 (d, J=1.5 Hz, 1H).

d. 3-Adamantan-1-yl-4-t-butyldimethylsilanyloxy bromobenzene.

A 2.0 L three-neck flask attached with a power-stirrer was charged with 2-adamantan-1-yl-4-bromophenol (102.8 g, 0.334 mol, 1.0 eq), DMAP (3.67 g, 0.0301 mol), anhydrous DMF (1.0 L) and triethylamine (76.1 g, 0.753 mol, 1.25 eq). Stirring was initiated and to the resulting solution at room temperature was added t-butyl-dimethylsilyl chloride (99.8 g, 0.662 mmol, 1.10 eq). The resulting mixture was allowed to stir overnight, poured into water, and extracted with diethyl ether (2×). The combined organics were washed successively with water and brine, dried over anhydrous magnesium sulfate, filtered, and evaporated. The residue was purified on silica gel (hexane) to give 179 g (70%) of 3-adamantan-1-yl-4-t-butyldimethylsilanyloxybromobenzene as a white powder. $^1$H NMR (300 MHz; CDCl$_3$): δ 0.33 (s, 6H), 1.03 (s, 9H), 1.75 (brs, 6H), 2.06 (s, 9H), 6.65 (d, J=8.4 Hz, 1H), 7.14 (dd, J$_1$=8.4 Hz, J$_2$=2.1 Hz, 1H), 7.29 (d, J=2.1 Hz, 1H).

e. 2-Adamantan-1-yl-4-bromophenol.

A 2.0 L three-neck flask attached with a power-stirrer was charged with 4-bromophenol (340.8 g, 1.97 mmol) and 1-adamantanol (300.0 g, 1.97 mmol) in 1.0 L of anhydrous CH$_2$Cl$_2$ at room temperature. Stirring was initiated and once all the reagents were solubilized then concentrated H$_2$SO$_4$ (105 mL, 193.2 g, 1.97 mmol, 1.0 eq) was added dropwise over 15–30 minutes. After approximately 1.0 hour a suspension resulted and the reaction was allowed to continue for a total of 24 hours. The suspension was carefully poured into ice water and neutralized with solid NaHCO$_3$. The resulting layers were separated and the aqueous layer extracted with CH$_2$Cl$_2$ (2×). The combined organics were washed with brine, dried (MgSO$_4$) and filtered. The solvent was removed under reduced pressure and the resulting solid was suspended in a minimal amount of hexanes. After stirring at room temperature for an hour the solid was collected via filtration and dried under reduced pressure to give 495.0 g (77%) of 2-adamantan-1-yl-4-bromophenol as a white solid. $^1$H NMR (300 MHz; CDCl$_3$): δ 1.77 (s, 6H), 2.08 (s, 9H), 4.81 (s, 1H), 6.53 (d, J=8.4 Hz, 1H), 7.14 (dd, J$_1$=8.7 Hz, J$_2$=2.4 Hz, 1H), 7.29 (d, J=2.4 Hz, 1H).

Example 34

4-[3-(1-Adamantyl)-4-hydroxy-5-fluoro-phenyl]benzylidene-2,4-thiazolidinedione, which may hereinafter be referred to as "Compound 34"

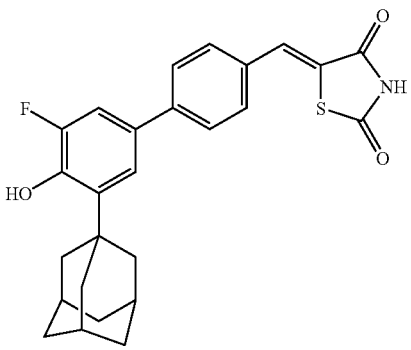

mp 305–308° C. $^1$H NMR (300 MHz, DMSO-d6): δ 1.73 (s, 6H), 2.04 (s, 3H), 2.13 (s, 6H), 7.25 (s, 1H), 7.45 (dd, J=1.8 Hz, J=12 Hz, 1H), 7.62 (d, J=8.7 Hz, 2H), 7.79 (d, J=9.0 Hz, 1H), 7.80 (s, 1H), 9.67 (d, J=2.7 Hz, 1H), 12.61 (s, 1H).

Example 35

4-[3-(1-Adamantyl)-4-hydroxy-phenyl]-5-hydroxy-benzylidene-2,4-thiazolidinedione, which may hereinafter be referred to as "Compound 35"

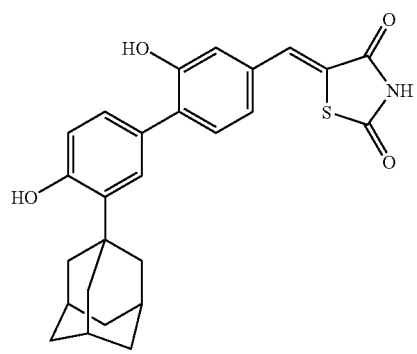

mp 224–226° C. $^1$H NMR (300 MHz, DMSO-d6): δ 1.73 (s, 6H); 2.06 (s, 9H); 6.80 (d, J=8.4 Hz, 1H); 7.10 (s, 1H); 7.12 (s, 1H); 7.28 (dd, J1=8.4 Hz, J2=2.1 Hz, 1H); 7.35 (d, J=2.1 Hz, 1H); 7.38 (s, 1H); 7.68 (s, 1H); 9.42 (s, 1H); 9.84 (s, 1H), 12.59 (brs, 1H).

Example 36

4-[3-(1-Adamantyl)-4-hydroxy-6-methyl-phenyl]benzylidene-2,4-thiazolidinedione, which may hereinafter be referred to as "Compound 36"

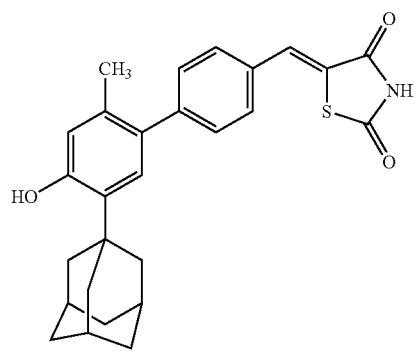

mp 275–280° C. $^1$H NMR (300 MHz, DMSO-d6): δ 1.72 (brs, 6H), 2.02 (brs, 3H), 2.07 (brs, 6H), 2.16 (s, 3H), 6.69 (s, 1H), 6.91 (s, 1H), 7.47 (d, 1H, J=8.4 Hz), 7.62 (d, 1H), J=8.1 Hz), 7.83 (s, 1H), 9.38 (s, 1H), 12.61 (s, 1H) ppm.

Example 37

6-[3-(1-Adamantyl)-4-hydroxy-5-fluoro-phenyl]-pyridin-3-ylmethylene]-thiazolidine-2,4-dione, which may hereinafter be referred to as "Compound 37"

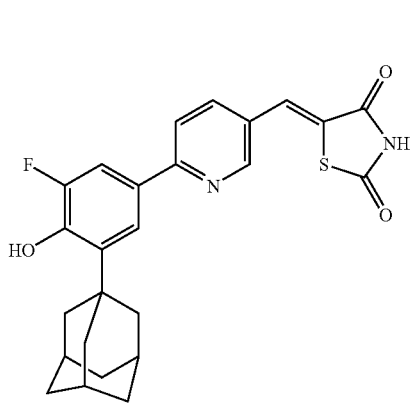

mp 307–310° C. $^1$H NMR (300 MHz, DMSO-d6): δ 1.73 (s, 6H), 2.05 (s, 3H), 2.12 (s, 6H), 7.77–7.83 (m, 3H), 7.91 (dd, J=2.1 Hz, J=8.7 Hz, 1H), 8.03 (d, J=8.4 Hz, 1H), 8.82 (d, J=2.4 Hz, 1H), 9.90 (d, J=2.4 Hz, 1H), 12.68 (brs, 1H).

Example 38

4-[3-(1-Adamantyl)-4-hydroxy-5-chloro-phenyl]benzylidene-2,4-thiazolidinedione, which may hereinafter be referred to as "Compound 38"

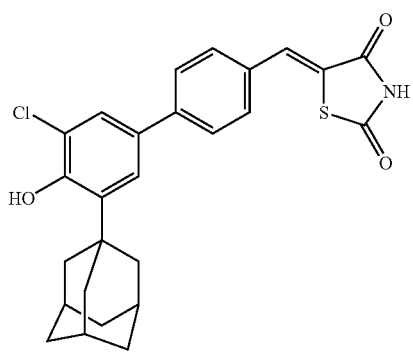

mp 323–328° C. $^1$H NMR (300 MHz, DMSO-d6): δ 1.76 (s, 6H), 2.08 (s, 3H), 2.16 (s, 6H), 7.39 (d, J=2.1 Hz, 1H), 7.57–7.66 (m, 3H), 7.72–7.83 (m, 3H), 9.21 (s, 1H), 12.59 (s, 1H).

Example 39

4-[3-(t-Butyl)-4-hydroxy-phenyl]benzylidene-2,4-thiazolidinedione, which may hereinafter be referred to as "Compound 39"

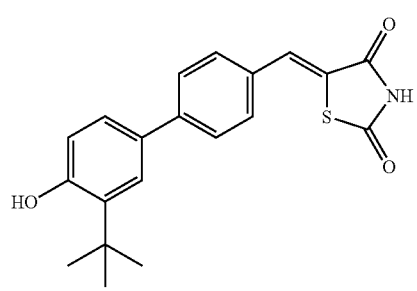

mp 256–257° C. $^1$H NMR (300 MHz, DMSO-d6): δ 1.40 (s, 9H), 6.88 (d, J=8.4 Hz, 1H), 7.42 (dd, J=8.4 Hz, J$_{12}$=1.8 Hz, 1H), 7.48 (d, J=1.8 Hz, 1H), 7.64 (d, J=8.4 Hz, 2H), 7.76 (d, J=8.4 Hz, 2H), 7.82 (s, 1H), 9.70 (s, 1H).

Example 40

6-[3-(t-Butyl)-4-hydroxy-phenyl]-pyridin-3-ylmethylene]-thiazolidine-2,4-dione, which may hereinafter be referred to as "Compound 40"

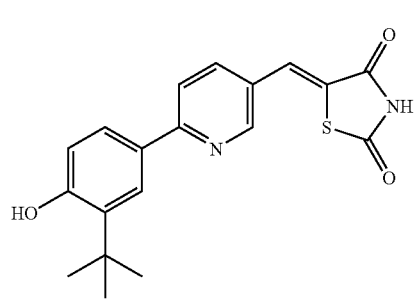

mp 303–304° C. $^1$H NMR (300 MHz, DMSO-d6): δ 1.41 (s, 9H), 6.91 (d, J=8.4 Hz, 1H), 7.83 (dd, J1=8.4 Hz, J2=2.0 Hz, 1H), 7.94 (dd, J1=8.7 Hz, J2=2.0 Hz, 1H), 8.01 (d, J=8.7 Hz, 1H), 8.05 (d, J=2.0 Hz, 1H), 8.84 (d, J=2.0 Hz, 1H), 9.93 (s, 1H).

Example 41

4-[3-(1-Adamantyl)-4-hydroxy-phenyl]-5-fluorobenzylidene-2,4-thiazolidinedione, which may hereinafter be referred to as "Compound 41"

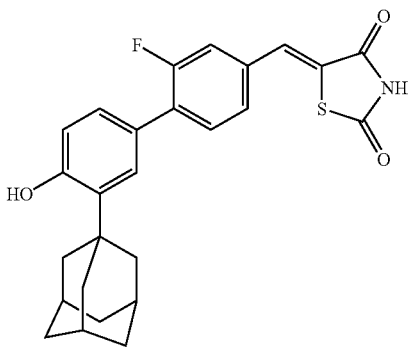

mp 270–274° C. $^1$H NMR (300 MHz, DMSO-d6): δ 1.74 (s, 6H), [2.04 (s), 2.11 (s), 9H], 6.88 (d, J=8.0 Hz, 1H), 7.31–7.25 (m, 2H), 7.46 (d, J=8.0 Hz, 1H), 7.51 (d, J=12.0 Hz, 1H), 7.65 (t, J=8.4 Hz, 1H), 7.79 (s, 1H), 9.70 (s, 1H), 12.54 (brs, 1H).

Example 42

4-[3-(1-Adamantyl)-4-hydroxy-phenyl]-6-fluorobenzylidene-2,4-thiazolidinedione, which may hereinafter be referred to as "Compound 42"

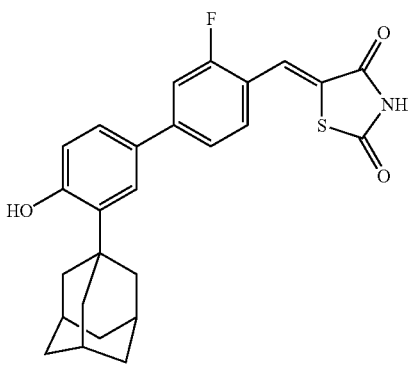

mp 307–309° C. $^1$H NMR (300 MHz, DMSO-d6): δ 1.74 (s, 6H), [2.06 (s), 2.13 (s), 9H], 6.88 (d, J=8.0 Hz, 1H), 7.40–7.65 (m, 5H), 7.79 (s, 1H), 9.74 (s, 1H), 12.71 (brs, 1H).

Example 43

6-[3-(1-Adamantyl)-4-hydroxy-5-chloro-phenyl]-pyridin-3-ylmethylene]-thiazolidine-2,4-dione, which may hereinafter be referred to as "Compound 43"

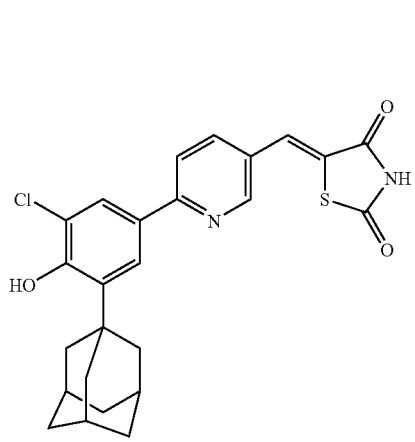

mp 339–342° C. $^1$H NMR (300 MHz, DMSO-d6): δ 1.76 (s, 6H), 2.08 (s, 3H), 2.15 (s, 6H), 7.85 (s, 1H), 7.94–7.99 (m, 2H), 8.04 (d, J=2.1 Hz, 1H), 8.10 (d, J=8.4 Hz, 1H), 8.87 (d, J=2.1 Hz, 1H), 9.53 (s, 1H), 12.71 (brs, 1H).

Example 44

6-[3-(1-Adamantyl)-4-hydroxy-5-methoxy-phenyl]-pyridin-3-ylmethylene]-thiazolidine-2,4-dione, which may hereinafter be referred to as "Compound 44"

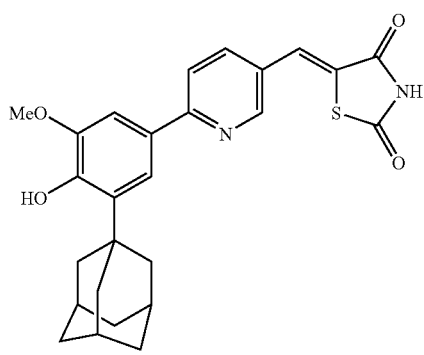

mp 211–216° C. $^1$H NMR (300 MHz, DMSO-d6): δ 1.75 (s, 6H), 2.06 (s, 3H), 2.14 (s, 6H), 3.90 (s, 3H), 7.64 (s, 2H), 7.84 (s, 1H), 7.95 (dd, J=8.4, J=2.4, 1H), 8.09 (d, J=8.4 Hz, 1H), 8.85 (d, J=2.4 Hz, 1H), 8.91 (s, 1H), 12.69 (broad s, 1H).

Example 45

4-[3-(1-Adamantyl)-4-hydroxy-phenyl]-5-methoxy-benzylidene-2,4-thiazolidinedione, which may hereinafter be referred to as "Compound 45"

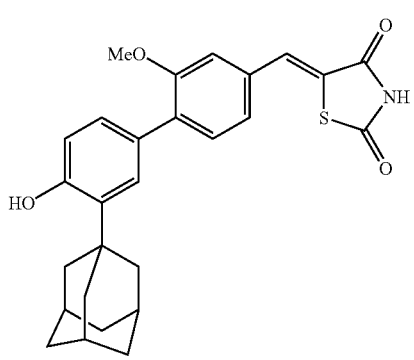

mp ° C. $^1$H NMR (300 MHz, DMSO-d6): δ.

Example 46

4-[3-(1-Adamantyl)-4-hydroxy-phenyl]-5-trifluoromethoxybenzylidene-2,4-thiazolidinedione, which may hereinafter be referred to as "Compound 46"

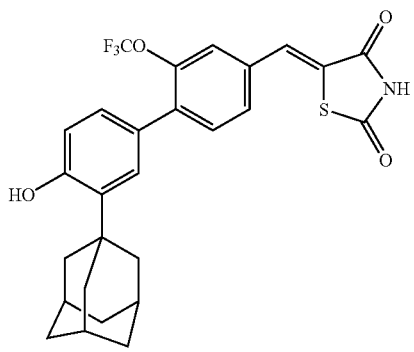

mp 238–240° C. $^1$H NMR (300 MHz, DMSO-d6): δ 1.71 (s, 6H); 2.02 (s, 3H); 2.07 (s, 6H); 6.86 (d, J=8.4 Hz, 1H); 7.16–7.26 (m, 2H); 7.60–7.70 (m, 3H); 7.85 (s, 1H); 9.68 (s, 1H).

Example 47

6-[3-(1-methylcyclohexyl)-4-hydroxy-phenyl]-pyridin-3-ylmethylene]-thiazolidine-2,4-dione, which may hereinafter be referred to as "Compound 47"

mp 293–295° C. $^1$H NMR (300 MHz, DMSO-d6): δ 1.20–1.75 (m, 12H); 2.17–2.27 (m, 2H); 6.88 (d, J=8.4 Hz, 1H); 7.77 (s, 1H); 7.81 (s, 1H); 7.90–7.99 (m, 1H); 8.82 (s, 1H), 9.86 (s, 1H); (m, 5H); 12.66 (brs, 1H).

Example 48

4-[3-(1-Adamantyl)-4-hydroxy-phenyl]-5-chlorobenzylidene-2,4thiazolidinedione, which may hereinafter be referred to as "Compound 48"

mp>280° C. (dec). $^1$H NMR (300 MHz, DMSO-d6): δ 1.73 (brs, 6H), 2.03 (brs, 3H), 2.10 (brs, 6H), 6.87 (d, 1H, J=7.8 Hz), 7.19 (m, 2H), 7.55 (s, 2H), 7.80 (d, 2H), 9.65 (s, 1H), 12.70 (brs, 1H).

Example 48

4-[3-(1-Adamantyl)-4-hydroxy-phenyl]-5-methyl-benzylidene-2,4-thiazolidinedione, which may hereinafter be referred to as "Compound 48"

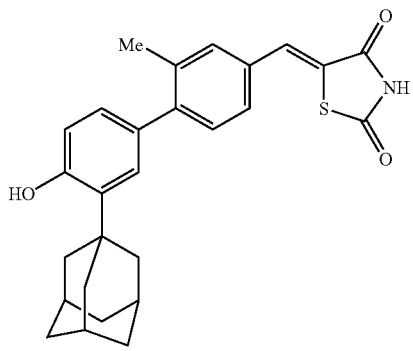

mp>305° C. (dec.). $^1$H NMR (300 MHz, DMSO-d6): δ 1.73 (brs, 6H), 2.03 (brs, 3H), 2.10 (brs, 6H), 2.31 (s, 3H), 6.85 (d, 1H, J=9.0 Hz), 7.05 (m, 2H), 7.35 (d, 1H, J=7.8 Hz), 7.44 (brd, 1H, J=8.4 Hz), 7.49 (brs, 1H), 7.77 (s, 1H), 9.50 (s, 1H), 12.61 (brs, 1H).

Example 49

4-[3-(1-Adamantyl)-4-hydroxy-phenyl]-5-ethoxy-benzylidene-2,4-thiazolidinedione, which may hereinafter be referred to as "Compound 49"

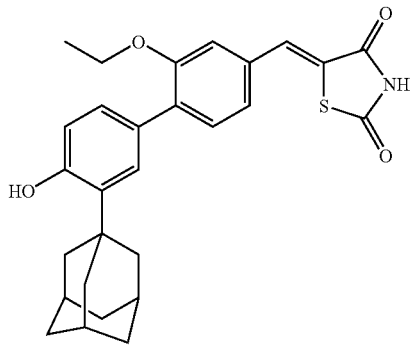

mp 298–302° C. $^1$H NMR (300 MHz, DMSO-d6): δ 1.34 (t, J=6.9 Hz, 3H), 1.73 (brs, 6H), [2.04 (brs), 2.10 (brs), 9 H], 4.08 (q, J=6.9 Hz, 2H), 6.81 (d, J=6.9 Hz, 1H), 7.15–7.30 (m, 3H), 7.38 (d, J=2.1 Hz, 1H), 7.44 (d, J=8.1 Hz, 1H), 7.81 (s, 1H), 9.47 (s, 1H), 12.61 (brs, 1H).

Example 50

4-[3-(1-Adamantyl)-4-hydroxy-phenyl]-5-nitrobenzylidene-2,4-thiazolidinedione, which may hereinafter be referred to as "Compound 50"

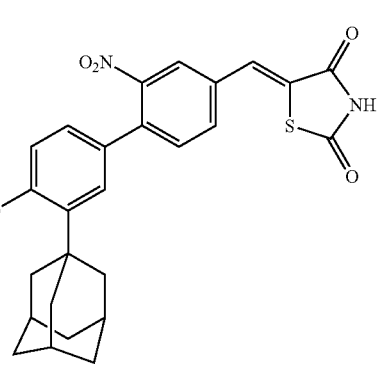

mp 262–264° C. $^1$H NMR (300 MHz, DMSO-d6): δ 1.73 (s, 6H); 2.04 (s, 3H); 2.06 (s, 6H); 6.87 (d, J=7.5 Hz, 1H); 7.03–7.10 (m, 2H); 7.71 (d, J=8.1 Hz, 1H); 7.82–7.90 (m, 2H); 8.12 (d, J=1.5 Hz, 1H); 9.78 (s, 1H); 12.78 (brs, 1H).

Example 51

4-[3-(1-Adamantyl)-4-hydroxy-phenyl]-5-aminobenzylidene-2,4-thiazolidinedione, which may hereinafter be referred to as "Compound 51"

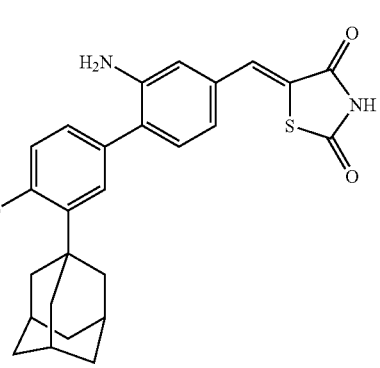

mp 167–169° C. $^1$H NMR (300 MHz, DMSO-d6): δ 1.73 (s, 6H); 2.03 (s, 3H); 2.10 (s, 6H); 5.03 (brs, 2H); 6.85 (d, J=8.1 Hz, 2H); 6.92 (d, J=1.5 Hz, 1H); 7.07–7.16 (m, 3H); 7.60 (s, 1H); 12.53 (brs, 1H).

Example 52

{1-[6-(3-Adamantan-1-yl-4-hydroxy-phenyl)-pyridin-3-yl]-ethyl}-thiazolidine-2,4-dione, which may hereinafter be referred to as "Compound 52"

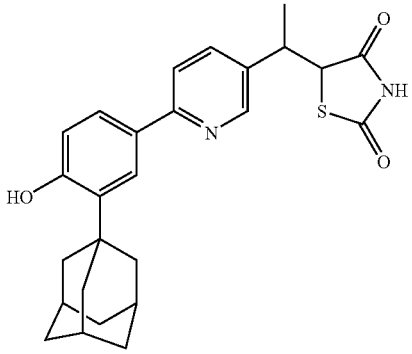

mp 169–171° C. $^1$H NMR (300 MHz, DMSO-d6): δ (2 diastereomers): 1.36 (d, J=6.6 Hz, 1.5H), 1.42 (d, J=7.2 Hz, 1.5H), 1.75 (brs, 6H), 2.06 (brs, 3H), 2.13 (brs, 6H), 3.74 (m, 1H), 5.02 (d, J=7.2 Hz, 0.5H), 5.04 (d, J=6.6 Hz, 0.5H), 6.86 (d, J=8.4 Hz, 0.5H), 6.87 (d, J=8.4 Hz, 0.5H), 7.69 (d, J=8.4 Hz, 0.5H), 7.69 (d, J=8.4 Hz, 7.75–7.86 (m, 3H), 8.44 (d, J=2.1 Hz, 0.5H), 8.55 (d, J=1.5 Hz, 0.5H), 9.71 (s, 0.5H), 9.73 (s, 0.5H), 11.92 (s, 0.5H), 12.18 (s, 0.5H).

Example 53

6-[3-(1-Adamantyl)-4-hydroxy-5-nitro-phenyl]-pyridin-3-ylmethylene]-thiazolidine-2,4-dione, which may hereinafter be referred to as "Compound 53"

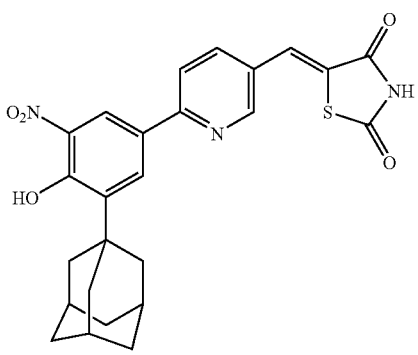

mp 291–293° C. $^1$H NMR (300 MHz, DMSO-d6): δ 1.78 (brs, 6H), 2.11 (brs, 3H), 2.19 (brs, 6H), 7.87 (s, 1H), 8.02 (d, J=10.2 Hz, 1H), 8.22 (d, J=8.4 Hz, 1H), 8.34 (s, 1H), 8.64 (s, 1H), 8.92 (s, 1H).

Example 54

(Z)-{1-[6-(3-Adamantan-1-yl-4-hydroxy-phenyl)-pyridin-3-yl]-ethylidene}-thiazolidine-2,4-dione, which may hereinafter be referred to as "Compound 54"

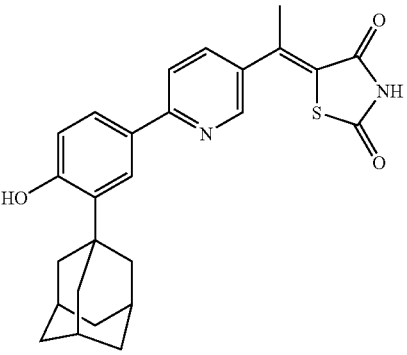

mp 181–182° C. $^1$H NMR (300 MHz, DMSO-d6): δ 1.75 (brs, 6H), 2.06 (brs, 3H), 2.13 (brs, 6H), 2.69 (s, 3H), 6.80 (d, J=8.4 Hz, 1H), 7.78 (dd, J=2.1, 8.4 Hz, 1H), 7.8–8.0 (m, 3H), 8.66 (d, J=2.4 Hz, 1H), 9.78 (s, 1H), 12.40 (s, 1H).

Example 55

(E)-{1-[6-(3-Adamantan-1-yl-4-hydroxy-phenyl)-pyridin-3-yl]-ethylidene}-thiazolidine-2,4-dione, which may hereinafter be referred to as "Compound 55"

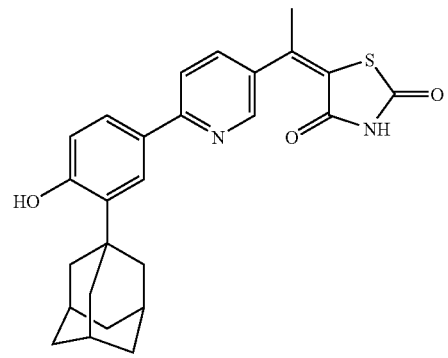

mp 224–225° C. $^1$H NMR (300 MHz, DMSO-d6): δ 1.75 (brs, 6H), 2.06 (brs, 3H), 2.13 (brs, 6H), 2.25 (s, 3H), 6.87 (d, J=8.4 Hz, 1H), 7.75 (dd, J=2.1, 8.4 Hz, 1H), 7.82 (s, 2H), 7.92 (d, J=2.1 Hz, 1H), 8.57 (d, J=2.4 Hz, 1H), 9.73 (s, 1H), 12.23 (s, 1H).

Example 56

In vitro Screening of Cancer Drug Candidates

Materials and Methods:

The human cell lines were screened for potential anti-cancer drug candidates:
One breast cancer cell lines, T-47D
One prostate cancer cell line (PC-3)
One lung cancer cell line (A549).
All cell lines were purchased from American Type Culture Collection (ATCC).

Culture Conditions:

A549 cells were grown in DME Dulbecco's modified Eagle's medium containing 4500 mg/L glucose; 4 mM L-glutamine; 10 U/ml Pen-G; 10 mcg/ml medium and 10% fetal calf serum (FCS).

PC-3 and T-47D cells were grown in RPMI medium 1640 containing 2 mM L-glutamine; 10 U/ml Pen-G; 10 mcg/ml Streptomycin and 10% FCS. For T-47D, 10 µg/mL of insulin was added to the culture medium.

Cells were kept at 6% $CO_2$ and 37° C.

Cell Density:

T-47D cells were seeded at 4,000 cell/well for both high and low serum conditions; PC-3 and A549 cells were seeded at 1,500 and 1,000 cell/well for 0.5% and 10% FCS, respectively.

Cells were seeded in 96-well format tissue culture plates the day before starting treatment, in the media indicated above.

Treatment:

Media were changed before each treatment, and fresh ones containing either 10% or 0.5% FCS were added, depending on the particular experiment.

The different compounds were tested at six concentrations: $1\times10^{-9}$, $1\times10^{-8}$, $5\times10^{-8}$, $1\times10^{-7}$, $1\times10^{-7}$, $1\times10^{-6}$.

DMSO was used as vehicle control, and never exceeded 0.1% final concentration. Treatment was repeated every other day, for a total of 5 days. As an end point, the percentage of surviving cells was measured using a standard colorimetric assay (MTT based).

MTT Assay:

The assay is based on the cleavage of the yellow tetrazolium salt MTT to purple formazan crystals by dehydrogenase activity in active mitochondria. Therefore, this conversion only occurs in living cells with intact/functional mitochondria. The formazan crystals formed are solubilized and the resulting colored solution is quantified using a scanning multiwell spectrophotometer.

Procedure:

10 µl of 5 mg/ml MTT dye are added to each well. Cells are incubated for additional 4 hours at 6% $CO_2$ and 37° C. Reaction is then stopped by adding 100 µl/well of the solubilization solution, consisting of 10% Sodium Dodecyl Sulfate (SDS) and 10 mM HCl.

Figure 2:
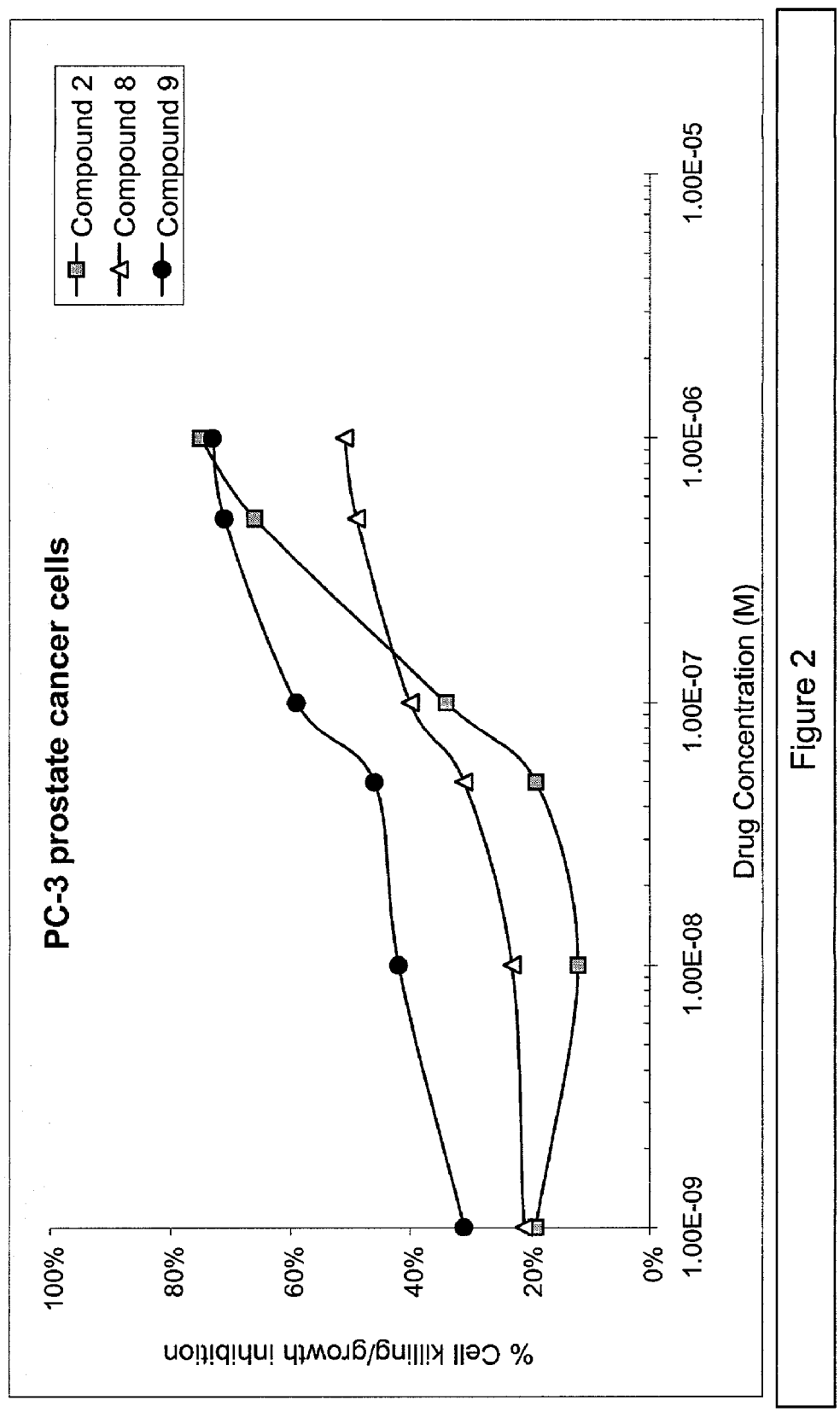
FIG. 2 shows the treatment of prostate cancer cells (PC-3) with compounds of the invention.
Figure 3:
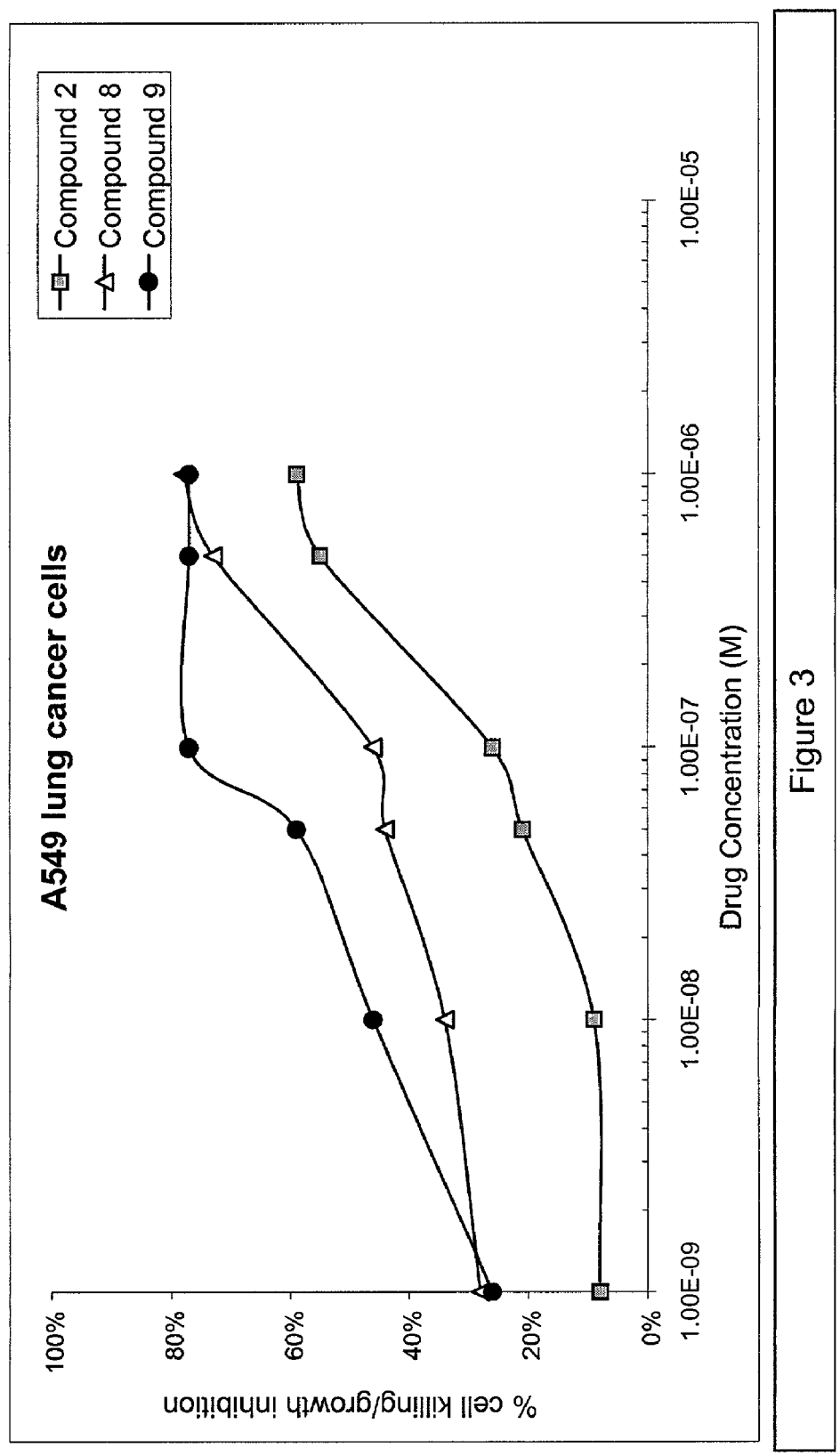
FIG. 3 shows the treatment of the lung cancer cells (A549) with the compounds of the invention.

Results:

See FIGS. 1, 2 and 3.

Example 57

In vivo Testing of Drug Candidates for the Treatment of Non-Small Cell Lung Cancer Methods:

Following in vitro evaluation, promising compounds were tested in an in vivo animal model for human cancer. Immunosuppressed, athymic nude mice inoculated with cells from a human tumor cell line were used to test the in vivo efficacy of selected anti-cancer compounds. The compounds tested include MX7001 (100 mg/Kg), MX7003 (150 mg/Kg), and MX7015 (50 mg/Kg). These compounds were suspended in sesame oil (Sigma #S3547) at different concentrations to provide a final treatment volume of 5 ml/kg administered by intraperitoneal injection 3 times per week.

Animals: Adult, male, athymic (Nude-nu/nu; Harlan Sprague Dawley) mice, 4–5 weeks of age were housed under standard conditions (OPRR/NIH approved facility).

Cells: Human non-small-cell lung cancer cells (A549) were grown in culture media supplemented with 10% fetal calf serum at 37° C. in a humid atmosphere containing 5% $CO_2$.

Animal Procedures: Exponentially growing A549 cells were harvested and washed three times with phosphate buffered saline (PBS). Animals were inoculated subcutaneously with three million cells suspended in sterile, 50% matrigel in PBS on the right flank. One week after inoculation, when average tumor volume is approximately 30 $mm^3$, the animals were divided into equal size treatment groups with equal average tumor volume. Tumors were measured with a caliper twice weekly for 5 weeks. Tumor volume is measured by calculating the product of tumor length, width, and width/2. Length and width represent the largest and smallest diameter of the tumor.

Figure 4:
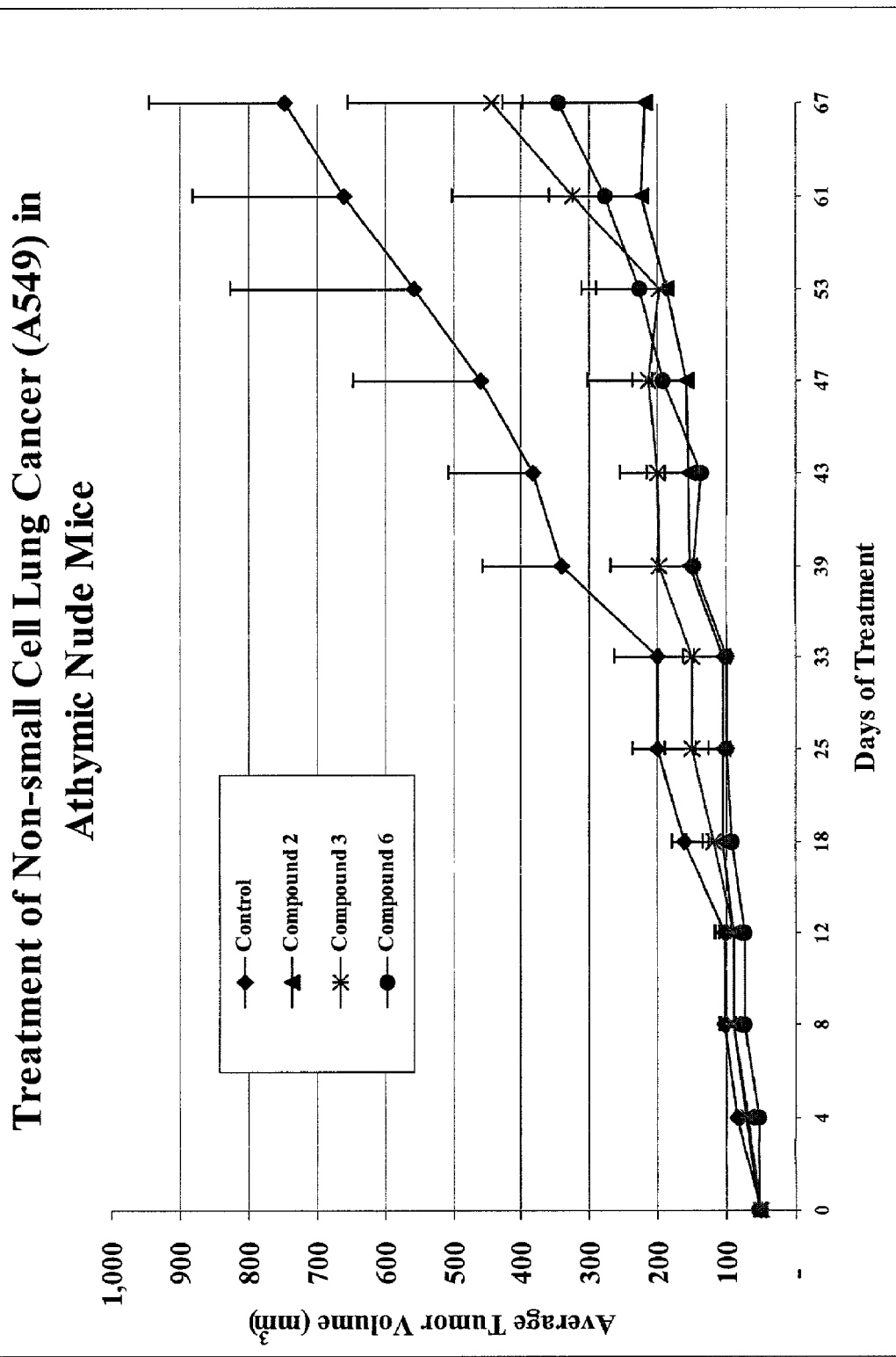
FIG. 4 shows the treatment of non-small cell lung cancer cells (A549) with the compounds of the invention.

Results:

All of the doses administered were well tolerated with no overt signs of toxicity. The compounds tested varied in efficacy, nevertheless, all of the compounds slowed tumor progression compared to control. Results for the non-small-cell lung cancer cell line A549 are shown in FIG. 4.

Example 58

In vivo Testing of Drug Candidates for the Treatment of Pancreatic Cancer

Methods:

Following in vitro evaluation, promising compounds were tested in an in vivo animal model for human pancreatic cancer. Immunosuppressed, athymic nude mice inoculated with cells from a human tumor cell line and are used to test the in vivo efficacy of selected anti-cancer compounds. Compound 33 was suspended in sesame oil (Sigma #S3547) and administered at 20 mg/kg in a volume of 5 ml/kg once daily.

Animals: Adult, male, athymic (Nude-nu/nu; Harlan Sprague Dawley) mice, 4–5 weeks of age were housed under standard conditions (OPRR/NIH approved facility).

Cells: Human Pancreatic cancer cells (BxPC-3) were grown in culture media supplemented with 10% fetal calf serum at 37° C. in a humid atmosphere containing 5% $CO_2$.

Animal Procedures: Exponentially growing BxPC-3 cells were harvested and washed three times with phosphate buffered saline (PBS). Animals were inoculated subcutaneously with three million cells suspended in sterile, 50% matrigel in PBS on the right flank. One week after inoculation, when average tumor volume is approximately 30 $mm^3$, the animals were divided into equal size treatment groups with equal average tumor volume. Tumors were measured with a caliper once weekly for 4–5 weeks. Tumor volume is measured by calculating the product of tumor length, width, and width/2. Length and width represent the largest and smallest diameter of the tumor.

Figure 11:
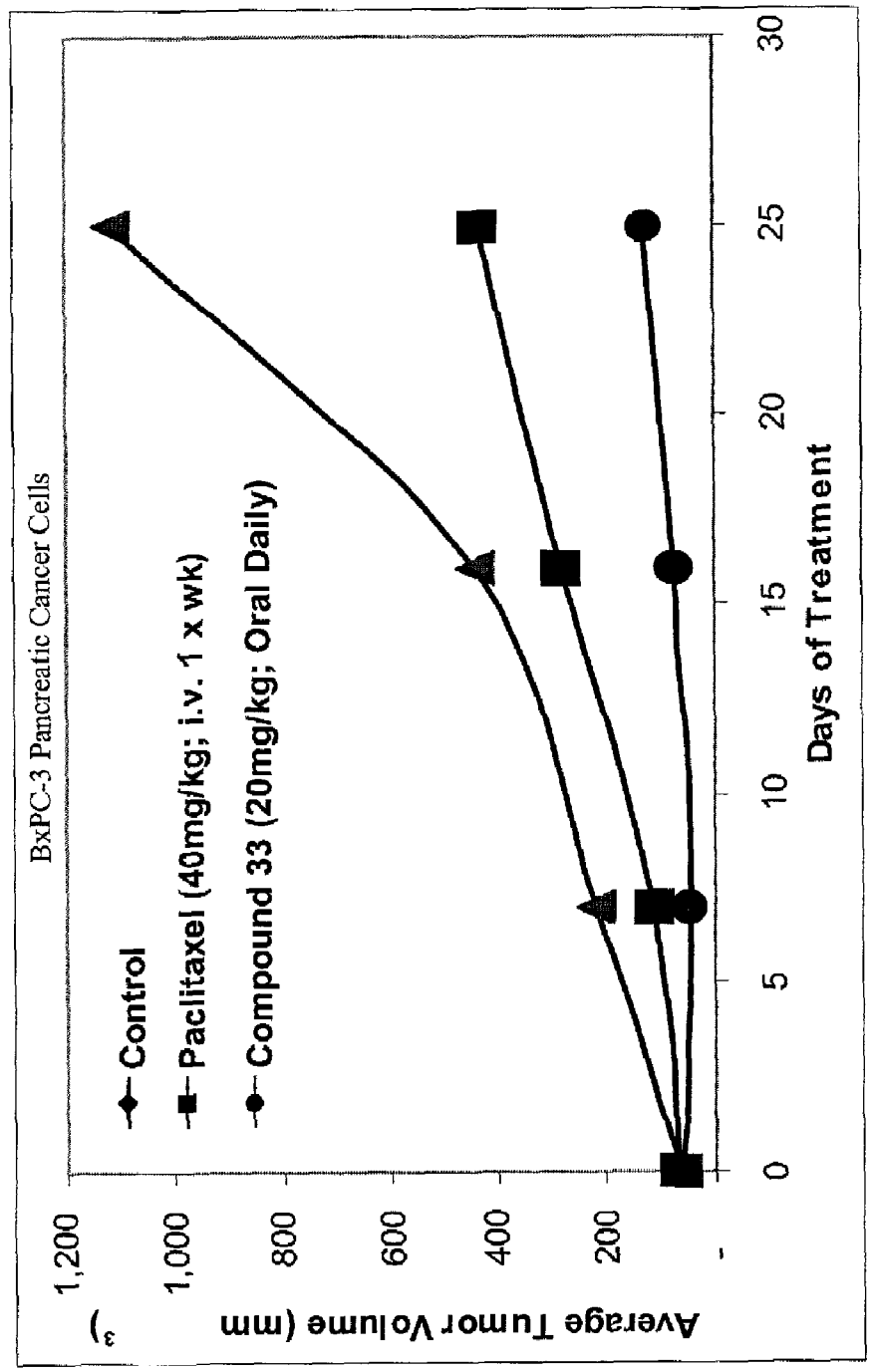
FIG. 11 shows the treatment of pancreatic cancer cells (BxPC-3) with the compounds of the invention.

Results:

All of the doses administered were well tolerated with no overt signs of toxicity. The compounds tested varied in efficacy, nevertheless, all of the compounds slowed tumor progression compared to control. Results for the pancreatic cell lines BXPC-3 are shown in FIG. 11.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A compound of the formula 6-[3-(1-Adamantyl)-4-hydroxy-phenyl]-pyridin-3-ylmethylene]-thiazolidine-2,4-dione, or a pharmaceutically acceptable salt thereof.

2. A pharmaceutical composition comprising the compound of claim 1 or a pharmaceutically acceptable salt thereof, and a pharmaceutically acceptable carrier.

3. A method of treating a disease of uncontrolled cellular proliferation, comprising administering one or more of the compounds of claim 1, or a pharmaceutically acceptable salt thereof, to a mammal diagnosed as having a disease selected from the group consisting of breast cancer, prostate cancer, colon cancer, lung cancer, or pancreatic cancer.

4. The method of claim 3, wherein the mammal is a human.

5. The method of claim 3, wherein the disease is breast cancer.

6. The method of claim 3, wherein the disease is prostate cancer.

7. The method of claim 3, wherein the disease is colon cancer.

8. The method of claim 3, wherein the disease is lung cancer.

9. The method of claim 3, wherein the disease is pancreatic cancer.

* * * * *